(12) United States Patent
Lang et al.

(10) Patent No.: US 8,479,738 B2
(45) Date of Patent: *Jul. 9, 2013

(54) BREATHING MASK ARRANGEMENT AS WELL AS AN APPLICATION DEVICE AND A FOREHEAD SUPPORT DEVICE FOR SAME

(75) Inventors: Bernd Christoph Lang, Gräfelfing (DE); Achim Biener, Munich (DE); Dieter Heidmann, Castle Hill (AU); Stefan Rolf Madaus, Gräfelfing (DE); Harald Wolfgang Vögele, Gauting (DE)

(73) Assignee: ResMed R&D Germany GmbH, Martinsried (DE)

( * ) Notice: Subject to any disclaimer, the term of this patent is extended or adjusted under 35 U.S.C. 154(b) by 0 days.

This patent is subject to a terminal disclaimer.

(21) Appl. No.: 13/067,282

(22) Filed: May 20, 2011

(65) Prior Publication Data

US 2011/0226254 A1  Sep. 22, 2011

Related U.S. Application Data

(63) Continuation of application No. 11/987,164, filed on Nov. 28, 2007, now Pat. No. 7,992,559, which is a continuation of application No. 10/493,424, filed as application No. PCT/EP02/11798 on Oct. 22, 2002, now Pat. No. 7,320,323.

(30) Foreign Application Priority Data

Oct. 22, 2001 (DE) .................................... 10151984
Jan. 17, 2002 (DE) .................................... 10201682
Mar. 14, 2002 (EP) ......................... PCT/EP02/02877

(51) Int. Cl.
*A62B 18/02* (2006.01)
*A62B 18/08* (2006.01)

(52) U.S. Cl.
USPC ............. 128/206.24; 128/205.25; 128/206.21

(58) Field of Classification Search
USPC ............. 128/205.25, 206.21, 206.18, 206.12, 128/206.23, 206.24, 206.26, 206.28, 207.11, 128/207.13
See application file for complete search history.

(56) References Cited

U.S. PATENT DOCUMENTS

| 4,429 A | 3/1846 | Cooke et al. |
| 35,724 A | 6/1862 | Wilcox |

(Continued)

FOREIGN PATENT DOCUMENTS

| AU | 91/77110 | 11/1991 |
| AU | 94/64816 | 12/1994 |

(Continued)

OTHER PUBLICATIONS

European Search Report issued in Appln. No. EP 02714190.2 (Jul. 11, 2006).

(Continued)

*Primary Examiner* — Kristen Matter
(74) *Attorney, Agent, or Firm* — Nixon & Vanderhye P.C.

(57) ABSTRACT

A forehead support device for a breathing mask includes a forehead support portion adapted to contact a forehead region of a user, a conduit element adapted to couple a respiratory gas conduit to the breathing mask, and a coupling structure provided between the forehead support portion and the conduit element and structured to support the conduit element at a predetermined spacing from the forehead support portion. The forehead support portion is displaceably engaged with the coupling structure such that the forehead portion can be selectively displaced relative to the coupling structure.

16 Claims, 27 Drawing Sheets

U.S. PATENT DOCUMENTS

| | | | |
|---|---|---|---|
| 364,394 A | 6/1887 | Bright | |
| 428,592 A | 5/1890 | Chapman | |
| 463,351 A | 11/1891 | Elliott | |
| 715,611 A | 12/1902 | Schnenker et al. | |
| 716,530 A | 12/1902 | Giddens | |
| 781,516 A | 1/1905 | Guthrie | |
| 812,706 A | 2/1906 | Warbasse | |
| 1,070,986 A | 8/1913 | Richter | |
| 1,081,745 A | 12/1913 | Johnston et al. | |
| 1,176,886 A | 3/1916 | Ermold | |
| 1,192,186 A | 7/1916 | Greene | |
| 1,206,045 A | 11/1916 | Smith | |
| 1,333,075 A | 3/1920 | Hill et al. | |
| 1,381,826 A | 6/1921 | Hansen | |
| 1,502,450 A | 7/1924 | Wood | |
| 1,610,793 A | 12/1926 | Kaufman | |
| 1,632,449 A | 6/1927 | McKesson | |
| 1,653,572 A | 12/1927 | Jackson | |
| 1,672,165 A | 6/1928 | Lewis | |
| 1,733,020 A | 10/1929 | Jones | |
| 1,837,591 A | 12/1931 | Shindel | |
| 1,926,027 A | 9/1933 | Biggs | |
| 2,029,129 A | 1/1936 | Schwartz | |
| 2,033,448 A | 3/1936 | James | |
| 2,123,353 A | 7/1938 | Catt | |
| 2,130,555 A | 9/1938 | Malcom | |
| 2,133,699 A | 10/1938 | Heidbrink | |
| 2,141,222 A | 12/1938 | Pioch | |
| 2,149,067 A | 2/1939 | Otero | |
| 2,245,658 A | 6/1941 | Erickson | |
| 2,245,969 A | 6/1941 | Francisco et al. | |
| 2,248,477 A | 7/1941 | Lombard | |
| 2,254,854 A | 9/1941 | O'Connell | |
| 2,287,353 A | 6/1942 | Minnick | |
| 2,317,608 A | 4/1943 | Heidbrink | |
| 2,359,506 A | 10/1944 | Battley et al. | |
| 2,371,965 A | 3/1945 | Lehmberg | |
| 2,376,871 A | 5/1945 | Fink | |
| 2,382,364 A | 8/1945 | Yant | |
| 2,415,846 A | 2/1947 | Randall | |
| 2,428,451 A | 10/1947 | Emerson | |
| 2,438,058 A | 3/1948 | Kincheloe | |
| 2,454,103 A | 11/1948 | Swidersky | |
| 2,473,518 A | 6/1949 | Garrard et al. | |
| D156,060 S | 11/1949 | Wade | |
| D161,337 S | 12/1950 | Hill | |
| 2,540,567 A | 2/1951 | Bennett | |
| 2,578,621 A | 12/1951 | Yant | |
| 2,590,006 A | 3/1952 | Gordon | |
| 2,617,751 A | 11/1952 | Bickett | |
| 2,625,155 A | 1/1953 | Engelder | |
| 2,638,161 A | 5/1953 | Jones | |
| 2,664,084 A | 12/1953 | Hammermann | |
| 2,693,178 A | 11/1954 | Gilroy | |
| 2,706,983 A | 4/1955 | Matheson et al. | |
| 2,747,464 A | 5/1956 | Bowerman | |
| 2,820,651 A | 1/1958 | Phillips | |
| 2,823,671 A | 2/1958 | Garelick | |
| 2,832,015 A | 4/1958 | Ortega | |
| 2,837,090 A | 6/1958 | Bloom et al. | |
| 2,868,196 A | 1/1959 | Stampe | |
| 2,875,757 A | 3/1959 | Galleher, Jr. | |
| 2,893,387 A | 7/1959 | Gongoll et al. | |
| 2,902,033 A | 9/1959 | Galleher, Jr. | |
| 2,917,045 A | 12/1959 | Schildknecht et al. | |
| 2,931,356 A | 4/1960 | Schwarz | |
| D188,084 S | 5/1960 | Garelick | |
| 2,939,458 A | 6/1960 | Lundquist | |
| 3,013,556 A | 12/1961 | Galleher | |
| 3,042,035 A | 7/1962 | Coanda | |
| 3,117,574 A | 1/1964 | Replogle | |
| 3,141,213 A | 7/1964 | Nicholas | |
| 3,182,659 A | 5/1965 | Blount et al. | |
| 3,189,027 A | 6/1965 | Bartlett | |
| 3,193,624 A | 7/1965 | Webb et al. | |
| 3,238,943 A | 3/1966 | Holley | |
| 3,288,138 A | 11/1966 | Sachs | |
| 3,315,672 A | 4/1967 | Cunningham et al. | |
| 3,315,674 A | 4/1967 | Bloom et al. | |
| 3,330,273 A | 7/1967 | Bennett | |
| 3,362,420 A | 1/1968 | Blackburn et al. | |
| 3,363,833 A | 1/1968 | Laerdal | |
| 3,474,783 A | 10/1969 | Ulmann | |
| 3,494,072 A | 2/1970 | Olson | |
| 3,523,534 A | 8/1970 | Nolan | |
| 3,535,810 A | 10/1970 | Baehrle | |
| 3,555,752 A | 1/1971 | Bogaert | |
| 3,556,122 A | 1/1971 | Laerdal | |
| 3,580,051 A | 5/1971 | Blevins | |
| 3,700,000 A | 10/1972 | Hesse et al. | |
| 3,720,235 A | 3/1973 | Schrock | |
| 3,725,953 A | 4/1973 | Johnson et al. | |
| 3,726,275 A | 4/1973 | Jackson et al. | |
| 3,750,333 A | 8/1973 | Vance | |
| 3,752,157 A | 8/1973 | Malmin | |
| 3,796,216 A | 3/1974 | Schwarz | |
| 3,799,164 A | 3/1974 | Rollins | |
| D231,803 S | 6/1974 | Huddy | |
| 3,824,999 A | 7/1974 | King | |
| 3,830,230 A | 8/1974 | Chester | |
| 3,978,854 A | 9/1976 | Mills, Jr. | |
| 4,034,426 A | 7/1977 | Hardwick et al. | |
| 4,049,357 A | 9/1977 | Hamisch, Jr. | |
| 4,062,357 A | 12/1977 | Laerdal | |
| 4,064,875 A | 12/1977 | Cramer et al. | |
| 4,069,516 A | 1/1978 | Watkins, Jr. | |
| 4,077,404 A | 3/1978 | Elam | |
| 4,111,197 A | 9/1978 | Warncke et al. | |
| D250,131 S | 10/1978 | Lewis et al. | |
| 4,120,302 A | 10/1978 | Ziegler | |
| 4,121,580 A | 10/1978 | Fabish | |
| 4,156,426 A | 5/1979 | Gold | |
| 4,161,946 A | 7/1979 | Zuesse | |
| 4,164,942 A | 8/1979 | Beard et al. | |
| 4,167,185 A | 9/1979 | Lewis | |
| 4,201,205 A | 5/1980 | Bartholomew | |
| 4,226,234 A | 10/1980 | Gunderson | |
| 4,231,363 A | 11/1980 | Grimes | |
| 4,233,972 A | 11/1980 | Hauff et al. | |
| 4,245,632 A | 1/1981 | Houston | |
| 4,248,218 A | 2/1981 | Fischer | |
| 4,265,239 A | 5/1981 | Fischer, Jr. et al. | |
| 4,266,540 A | 5/1981 | Panzik et al. | |
| 4,274,404 A | 6/1981 | Molzan et al. | |
| 4,275,908 A | 6/1981 | Elkins et al. | |
| D262,322 S | 12/1981 | Mizerak | |
| 4,304,229 A | 12/1981 | Curtin | |
| 4,328,797 A | 5/1982 | Rollins et al. | |
| 4,337,767 A | 7/1982 | Yahata | |
| 4,347,205 A | 8/1982 | Stewart | |
| 4,354,488 A | 10/1982 | Bartos | |
| 4,369,284 A | 1/1983 | Chen | |
| 4,380,102 A | 4/1983 | Hansson | |
| 4,402,316 A | 9/1983 | Gadberry | |
| 4,412,537 A | 11/1983 | Tiger | |
| 4,414,973 A | 11/1983 | Matheson et al. | |
| 4,417,575 A | 11/1983 | Hilton et al. | |
| 4,446,576 A | 5/1984 | Hisataka | |
| 4,454,880 A | 6/1984 | Muto et al. | |
| 4,454,881 A | 6/1984 | Huber et al. | |
| 4,458,679 A | 7/1984 | Ward | |
| 4,467,799 A | 8/1984 | Steinberg | |
| 4,494,538 A | 1/1985 | Ansite | |
| 4,506,665 A | 3/1985 | Andrews et al. | |
| 4,522,639 A | 6/1985 | Ansite et al. | |
| 4,549,334 A | 10/1985 | Miller | |
| 4,558,710 A | 12/1985 | Eichler | |
| 4,572,323 A | 2/1986 | Randall | |
| 4,579,113 A | 4/1986 | McCreadie et al. | |
| 4,580,556 A | 4/1986 | Kondur | |
| 4,593,688 A | 6/1986 | Payton | |
| 4,606,340 A | 8/1986 | Ansite | |
| D285,496 S | 9/1986 | Berman | |
| 4,616,647 A | 10/1986 | McCreadie | |
| 4,622,964 A | 11/1986 | Flynn | |
| 4,633,972 A | 1/1987 | DeRocher | |
| 4,655,213 A | 4/1987 | Rapoport et al. | |

| | | | | | |
|---|---|---|---|---|---|
| 4,657,010 A | 4/1987 | Wright | 5,109,840 A | 5/1992 | Daleiden |
| 4,665,570 A | 5/1987 | Davis | 5,121,745 A | 6/1992 | Israel |
| 4,671,271 A | 6/1987 | Bishop et al. | 5,133,347 A | 7/1992 | Huennebeck |
| 4,674,134 A | 6/1987 | Lundin | 5,136,760 A | 8/1992 | Sano et al. |
| 4,676,241 A | 6/1987 | Webb et al. | 5,138,722 A | 8/1992 | Urella et al. |
| 4,677,975 A | 7/1987 | Edgar et al. | 5,140,980 A | 8/1992 | Haughey et al. |
| 4,677,977 A | 7/1987 | Wilcox | 5,140,982 A | 8/1992 | Bauman |
| 4,686,977 A | 8/1987 | Cosma | 5,146,914 A | 9/1992 | Sturrock |
| 4,707,863 A | 11/1987 | McNeal | 5,156,146 A | 10/1992 | Corces et al. |
| 4,713,844 A | 12/1987 | Westgate | 5,159,938 A | 11/1992 | Laughlin |
| H397 H | 1/1988 | Stark | 5,178,138 A | 1/1993 | Walstrom et al. |
| D293,613 S | 1/1988 | Wingler | 5,181,506 A | 1/1993 | Tardiff, Jr. et al. |
| 4,732,147 A | 3/1988 | Fuller | D333,015 S | 2/1993 | Farmer |
| 4,739,755 A | 4/1988 | White et al. | D334,633 S | 4/1993 | Rudolph |
| 4,770,169 A | 9/1988 | Schmoegner et al. | 5,199,424 A | 4/1993 | Sullivan et al. |
| 4,772,760 A | 9/1988 | Graham | D335,322 S | 5/1993 | Jones |
| 4,774,941 A | 10/1988 | Cook | 5,215,336 A | 6/1993 | Worthing |
| 4,782,832 A | 11/1988 | Trimble et al. | 5,220,699 A | 6/1993 | Farris |
| 4,783,029 A | 11/1988 | Geppert et al. | 5,231,983 A | 8/1993 | Matson et al. |
| 4,794,921 A | 1/1989 | Lindkvist | 5,233,978 A | 8/1993 | Callaway |
| 4,799,477 A | 1/1989 | Lewis | 5,243,971 A | 9/1993 | Sullivan et al. |
| 4,807,617 A | 2/1989 | Nesti | 5,245,995 A | 9/1993 | Sullivan et al. |
| 4,809,692 A | 3/1989 | Nowacki et al. | 5,253,641 A | 10/1993 | Choate |
| 4,811,730 A | 3/1989 | Milano | 5,265,595 A | 11/1993 | Rudolph |
| 4,819,629 A | 4/1989 | Jonson | 5,269,296 A | 12/1993 | Landis |
| 4,821,713 A | 4/1989 | Bauman | 5,279,289 A | 1/1994 | Kirk |
| 4,827,924 A | 5/1989 | Japuntich | 5,280,784 A | 1/1994 | Kohler |
| 4,832,017 A | 5/1989 | Schnoor | 5,291,880 A | 3/1994 | Almovist et al. |
| 4,835,820 A | 6/1989 | Robbins, III | 5,301,689 A | 4/1994 | Wennerholm |
| 4,841,953 A | 6/1989 | Dodrill | 5,311,862 A | 5/1994 | Blasdell et al. |
| 4,848,334 A | 7/1989 | Bellm | 5,322,057 A | 6/1994 | Raabe et al. |
| 4,848,366 A | 7/1989 | Aita et al. | 5,322,059 A | 6/1994 | Walther |
| 4,850,346 A | 7/1989 | Michel et al. | 5,331,691 A | 7/1994 | Runckel |
| 4,856,118 A | 8/1989 | Sapiejewski | 5,334,646 A | 8/1994 | Chen |
| D304,384 S | 10/1989 | Derobert | 5,343,878 A | 9/1994 | Scarberry et al. |
| 4,870,963 A | 10/1989 | Carter | 5,357,945 A | 10/1994 | Messina |
| 4,875,714 A | 10/1989 | Lee | 5,357,951 A | 10/1994 | Ratner |
| 4,875,718 A | 10/1989 | Marken | 5,372,130 A | 12/1994 | Stern et al. |
| 4,886,058 A | 12/1989 | Brostrom et al. | 5,388,273 A | 2/1995 | Sydor et al. |
| 4,898,174 A | 2/1990 | Fangrow, Jr. | 5,388,571 A | 2/1995 | Roberts et al. |
| 4,899,614 A | 2/1990 | Katamui | 5,390,373 A | 2/1995 | Flory |
| 4,905,683 A | 3/1990 | Cronjaeger | 5,391,248 A | 2/1995 | Brain |
| 4,905,686 A | 3/1990 | Adams | 5,398,673 A | 3/1995 | Lambert |
| 4,907,584 A | 3/1990 | McGinnis | 5,400,781 A | 3/1995 | Davenport |
| 4,910,806 A | 3/1990 | Baker et al. | 5,404,871 A | 4/1995 | Goodman et al. |
| 4,915,105 A | 4/1990 | Lee | 5,411,021 A | 5/1995 | Gdulla et al. |
| 4,915,106 A | 4/1990 | Aulgur et al. | 5,419,317 A | 5/1995 | Blasdell et al. |
| 4,919,128 A | 4/1990 | Kopala et al. | 5,419,318 A | 5/1995 | Tayebi |
| 4,938,210 A | 7/1990 | Shene | 5,429,126 A | 7/1995 | Bracken |
| 4,938,212 A | 7/1990 | Snook et al. | 5,429,683 A | 7/1995 | Le Mitouard |
| 4,944,310 A | 7/1990 | Sullivan | 5,431,158 A | 7/1995 | Tirotta |
| 4,946,202 A | 8/1990 | Perricone | 5,438,981 A | 8/1995 | Starr et al. |
| D310,431 S | 9/1990 | Bellm | 5,441,046 A | 8/1995 | Starr et al. |
| 4,960,121 A | 10/1990 | Nelson et al. | D362,061 S | 9/1995 | McGinnis et al. |
| 4,971,051 A | 11/1990 | Toffolon | 5,477,852 A | 12/1995 | Landis et al. |
| 4,974,586 A | 12/1990 | Wandel et al. | 5,479,920 A | 1/1996 | Piper et al. |
| 4,986,269 A | 1/1991 | Hakkinen | 5,481,763 A | 1/1996 | Brostrom et al. |
| 4,989,271 A | 2/1991 | Sapiejewski et al. | 5,485,837 A | 1/1996 | Soles Bee et al. |
| 4,989,596 A | 2/1991 | Macris et al. | 5,488,948 A | 2/1996 | Dubruille et al. |
| 4,989,599 A | 2/1991 | Carter | 5,492,116 A | 2/1996 | Scarberry et al. |
| 4,997,217 A | 3/1991 | Kunze | 5,501,214 A | 3/1996 | Sabo |
| 5,003,631 A | 4/1991 | Richardson | 5,509,404 A | 4/1996 | Lloyd et al. |
| 5,003,633 A | 4/1991 | Itoh | 5,511,541 A | 4/1996 | Dearstine |
| 5,005,568 A | 4/1991 | Loescher et al. | 5,517,986 A | 5/1996 | Starr et al. |
| 5,005,571 A | 4/1991 | Dietz | 5,522,382 A | 6/1996 | Sullivan et al. |
| 5,018,519 A | 5/1991 | Brown | 5,538,000 A | 7/1996 | Rudolph |
| 5,027,809 A | 7/1991 | Robinson | 5,538,001 A | 7/1996 | Bridges |
| 5,038,776 A | 8/1991 | Harrison et al. | 5,540,223 A | 7/1996 | Starr et al. |
| 5,042,473 A | 8/1991 | Lewis | 5,542,128 A | 8/1996 | Lomas |
| 5,042,478 A | 8/1991 | Kopala et al. | 5,546,936 A | 8/1996 | Virag et al. |
| 5,046,200 A | 9/1991 | Feder | 5,558,090 A | 9/1996 | James |
| 5,054,482 A | 10/1991 | Bales | RE35,339 E | 10/1996 | Rapoport |
| 5,062,421 A | 11/1991 | Burns et al. | 5,560,354 A | 10/1996 | Berthon-Jones et al. |
| 5,063,922 A | 11/1991 | Hakkinen | 5,570,682 A | 11/1996 | Johnson |
| 5,069,205 A | 12/1991 | Urso | 5,570,684 A | 11/1996 | Behr |
| 5,074,297 A | 12/1991 | Venegas | 5,570,689 A | 11/1996 | Starr et al. |
| D323,908 S | 2/1992 | Hollister et al. | 5,575,278 A | 11/1996 | Bonhomme et al. |
| 5,093,940 A | 3/1992 | Nishiyama | D377,089 S | 12/1996 | Starr et al. |
| 5,109,839 A | 5/1992 | Blasdell et al. | 5,592,937 A | 1/1997 | Freund |

| Patent No. | Date | Inventor |
|---|---|---|
| 5,592,938 A | 1/1997 | Scarberry et al. |
| 5,608,647 A | 3/1997 | Rubsmen et al. |
| 5,617,849 A | 4/1997 | Springett et al. |
| 5,642,730 A | 7/1997 | Baran |
| 5,645,049 A | 7/1997 | Foley et al. |
| 5,645,054 A | 7/1997 | Cotner et al. |
| 5,647,355 A | 7/1997 | Starr et al. |
| 5,647,357 A | 7/1997 | Barnett et al. |
| 5,649,532 A | 7/1997 | Griffiths |
| 5,649,533 A | 7/1997 | Oren |
| 5,655,520 A | 8/1997 | Howe et al. |
| 5,655,527 A | 8/1997 | Scarberry et al. |
| 5,657,493 A | 8/1997 | Ferrero et al. |
| 5,657,752 A | 8/1997 | Landis et al. |
| 5,660,174 A | 8/1997 | Jacobelli |
| 5,662,101 A | 9/1997 | Ogden et al. |
| 5,666,946 A | 9/1997 | Langenback |
| 5,676,133 A | 10/1997 | Hickle et al. |
| D385,960 S | 11/1997 | Rudolph |
| 5,685,296 A | 11/1997 | Zdrojkowski et al. |
| 5,687,715 A | 11/1997 | Landis et al. |
| 5,704,345 A | 1/1998 | Berthon-Jones |
| 5,709,204 A | 1/1998 | Lester |
| 5,715,814 A | 2/1998 | Ebers |
| 5,724,964 A | 3/1998 | Brunson et al. |
| 5,724,965 A | 3/1998 | Handke et al. |
| 5,740,795 A | 4/1998 | Brydon |
| 5,743,414 A | 4/1998 | Baudino |
| 5,746,201 A | 5/1998 | Kidd |
| 5,794,617 A | 8/1998 | Brunell et al. |
| D398,987 S | 9/1998 | Cotner et al. |
| 5,813,423 A | 9/1998 | Kirchgeorg |
| 5,832,918 A | 11/1998 | Pantino |
| 5,839,436 A | 11/1998 | Fangrow et al. |
| D402,755 S | 12/1998 | Kwok |
| 5,860,677 A | 1/1999 | Martins et al. |
| RE36,165 E | 3/1999 | Behr |
| 5,884,624 A | 3/1999 | Barnett et al. |
| 5,896,857 A | 4/1999 | Hely et al. |
| 5,906,199 A | 5/1999 | Budzinski |
| 5,909,732 A | 6/1999 | Diesel et al. |
| 5,921,239 A | 7/1999 | McCall et al. |
| 5,935,136 A | 8/1999 | Hulse et al. |
| 5,937,851 A | 8/1999 | Serowski et al. |
| 5,966,745 A | 10/1999 | Schwartz et al. |
| 5,975,079 A | 11/1999 | Hellings et al. |
| 5,979,025 A | 11/1999 | Horng |
| 6,006,748 A | 12/1999 | Hollis |
| D419,658 S | 1/2000 | Matchett et al. |
| 6,016,804 A | 1/2000 | Gleason et al. |
| D421,298 S | 2/2000 | Kenyon et al. |
| 6,019,101 A | 2/2000 | Cotner et al. |
| 6,029,660 A | 2/2000 | Calluaud et al. |
| 6,029,665 A | 2/2000 | Berthon-Jones |
| 6,029,668 A | 2/2000 | Freed |
| 6,039,044 A | 3/2000 | Sullivan |
| D423,096 S | 4/2000 | Kwok |
| 6,044,844 A | 4/2000 | Kwok et al. |
| 6,062,148 A | 5/2000 | Hodge et al. |
| 6,062,221 A | 5/2000 | Brostrom et al. |
| 6,082,360 A | 7/2000 | Rudolph et al. |
| 6,091,973 A | 7/2000 | Colla et al. |
| D428,987 S | 8/2000 | Kwok |
| 6,098,205 A | 8/2000 | Schwartz et al. |
| 6,112,746 A | 9/2000 | Kwok et al. |
| 6,119,693 A | 9/2000 | Kwok et al. |
| 6,123,071 A | 9/2000 | Berthon-Jones et al. |
| 6,152,137 A | 11/2000 | Schwartz et al. |
| 6,189,532 B1 | 2/2001 | Hely et al. |
| 6,192,886 B1 | 2/2001 | Rudolph |
| D439,326 S | 3/2001 | Hecker et al. |
| 6,196,223 B1 | 3/2001 | Belfer et al. |
| D443,355 S | 6/2001 | Gunaratnam et al. |
| 6,240,605 B1 | 6/2001 | Stevens et al. |
| 6,250,375 B1 | 6/2001 | Lee et al. |
| 6,256,846 B1 | 7/2001 | Lee |
| 6,257,237 B1 | 7/2001 | Suzuki |
| 6,272,722 B1 | 8/2001 | Lai |
| 6,321,421 B1 | 11/2001 | Lim |
| 6,341,606 B1 | 1/2002 | Bordewick et al. |
| 6,347,631 B1 | 2/2002 | Hansen et al. |
| 6,357,441 B1 | 3/2002 | Kwok et al. |
| 6,374,826 B1 | 4/2002 | Gunaratnam et al. |
| 6,381,813 B1 | 5/2002 | Lai |
| 6,388,640 B1 | 5/2002 | Chigira et al. |
| 6,397,847 B1 | 6/2002 | Scarberry et al. |
| 6,412,487 B1 | 7/2002 | Gunaratnam et al. |
| 6,418,928 B1 | 7/2002 | Bordewick et al. |
| 6,422,238 B1 | 7/2002 | Lithgow |
| 6,427,694 B1 | 8/2002 | Hecker et al. |
| 6,431,172 B1 | 8/2002 | Bordewick |
| 6,435,181 B1 | 8/2002 | Jones, Jr. et al. |
| 6,439,230 B1 | 8/2002 | Gunaratnam et al. |
| 6,449,817 B1 | 9/2002 | Hsu |
| 6,463,931 B1 | 10/2002 | Kwok et al. |
| 6,467,483 B1 | 10/2002 | Kopacko et al. |
| 6,491,034 B1 | 12/2002 | Gunaratnam |
| 6,494,207 B1 | 12/2002 | Kwok |
| D468,823 S | 1/2003 | Smart |
| 6,513,206 B1 | 2/2003 | Banitt et al. |
| 6,513,526 B2 | 2/2003 | Kwok et al. |
| 6,520,182 B1 | 2/2003 | Gunaratnam |
| 6,530,373 B1 | 3/2003 | Patron et al. |
| 6,532,961 B1 | 3/2003 | Kwok et al. |
| 6,536,435 B1 | 3/2003 | Fecteau et al. |
| 6,557,556 B2 | 5/2003 | Kwok |
| 6,561,190 B1 | 5/2003 | Kwok |
| 6,561,191 B1 | 5/2003 | Kwok |
| 6,581,601 B2 | 6/2003 | Ziaee |
| 6,595,214 B1 | 7/2003 | Hecker |
| 6,615,830 B1 | 9/2003 | Serowski et al. |
| 6,615,832 B1 | 9/2003 | Chen |
| 6,615,834 B2 | 9/2003 | Gradon et al. |
| 6,626,177 B1 | 9/2003 | Ziaee |
| 6,631,718 B1 | 10/2003 | Lovell |
| D484,237 S | 12/2003 | Lang et al. |
| 6,679,260 B2 | 1/2004 | Her |
| 6,679,261 B2 | 1/2004 | Lithgow |
| 6,691,707 B1 | 2/2004 | Gunaratnam et al. |
| 6,691,708 B2 | 2/2004 | Kwok et al. |
| 6,701,535 B2 | 3/2004 | Dobbie et al. |
| 6,701,927 B2 | 3/2004 | Kwok et al. |
| 6,705,647 B1 | 3/2004 | Palmer |
| 6,712,072 B1 | 3/2004 | Lang |
| 6,729,333 B2 | 5/2004 | Barnett et al. |
| D492,992 S | 7/2004 | Guney et al. |
| D493,521 S | 7/2004 | Guney |
| 6,789,543 B2 | 9/2004 | Cannon |
| 6,796,308 B2 | 9/2004 | Gunaratnam et al. |
| 6,805,117 B1 | 10/2004 | Ho et al. |
| 6,823,869 B2 | 11/2004 | Raje et al. |
| 6,832,615 B2 | 12/2004 | Hensel |
| D502,260 S | 2/2005 | Lang et al. |
| 6,851,425 B2 | 2/2005 | Jaffre |
| 6,851,428 B2 | 2/2005 | Dennis |
| 6,907,882 B2 | 6/2005 | Ging |
| 6,918,390 B2 | 7/2005 | Lithgow et al. |
| 6,926,004 B2 | 8/2005 | Schumacher |
| 6,968,844 B2 | 11/2005 | Liland et al. |
| 6,973,929 B2 | 12/2005 | Gunaratnam |
| 6,986,352 B2 | 1/2006 | Frater et al. |
| D515,698 S | 2/2006 | Lang et al. |
| 6,997,188 B2 | 2/2006 | Kwok et al. |
| 7,000,614 B2 | 2/2006 | Lang et al. |
| 7,005,414 B2 | 2/2006 | Barnikol et al. |
| 7,007,696 B2 | 3/2006 | Palkon et al. |
| 7,011,090 B2 | 3/2006 | Drew et al. |
| 7,021,311 B2 | 4/2006 | Gunaratnam et al. |
| 7,036,508 B2 | 5/2006 | Kwok |
| 7,047,965 B1 | 5/2006 | Ball |
| 7,047,972 B2 | 5/2006 | Ging et al. |
| 7,059,326 B2 | 6/2006 | Heidmann et al. |
| 7,066,379 B2 | 6/2006 | Eaton et al. |
| 7,089,939 B2 | 8/2006 | Walker et al. |
| 7,095,938 B2 | 8/2006 | Tolstikhin |
| 7,100,610 B2 | 9/2006 | Biener et al. |
| 7,107,989 B2 | 9/2006 | Frater et al. |
| 7,112,179 B2 | 9/2006 | Bonutti et al. |

| | | |
|---|---|---|
| 7,178,525 B2 | 2/2007 | Matula, Jr. et al. |
| 7,185,652 B2 | 3/2007 | Gunaratnam et al. |
| 7,207,334 B2 | 4/2007 | Smart |
| 7,207,335 B2 | 4/2007 | Kwok et al. |
| 7,216,647 B2 | 5/2007 | Lang et al. |
| 7,219,670 B2 | 5/2007 | Jones et al. |
| 7,234,466 B2 | 6/2007 | Kwok et al. |
| 7,234,773 B2 | 6/2007 | Raftery et al. |
| 7,290,546 B2 | 11/2007 | Ho et al. |
| 7,296,574 B2 | 11/2007 | Sprinkle et al. |
| 7,318,437 B2 | 1/2008 | Gunaratnam et al. |
| 7,318,439 B2 | 1/2008 | Raje et al. |
| 7,320,323 B2 | 1/2008 | Lang et al. |
| 7,353,826 B2 | 4/2008 | Sleeper et al. |
| 7,353,827 B2 | 4/2008 | Geist |
| 7,406,965 B2 | 8/2008 | Kwok et al. |
| 7,461,656 B2 | 12/2008 | Gunaratnam et al. |
| 7,472,704 B2 | 1/2009 | Gunaratnam |
| 7,487,772 B2 | 2/2009 | Ging et al. |
| 7,487,777 B2 | 2/2009 | Gunaratnam et al. |
| 7,503,327 B2 | 3/2009 | Gunaratnam |
| 7,509,958 B2 | 3/2009 | Amarasinghe et al. |
| 7,523,754 B2 | 4/2009 | Lithgow |
| 7,610,916 B2 | 11/2009 | Kwok et al. |
| 7,614,400 B2 | 11/2009 | Lithgow et al. |
| 7,621,274 B2 | 11/2009 | Sprinkle et al. |
| 7,654,263 B2 | 2/2010 | Lang et al. |
| 7,743,767 B2 | 6/2010 | Ging et al. |
| 7,762,259 B2 | 7/2010 | Gunaratnam |
| 7,775,209 B2 | 8/2010 | Biener et al. |
| 7,779,832 B1 | 8/2010 | Ho |
| 7,814,911 B2 | 10/2010 | Bordewick et al. |
| 7,819,119 B2 | 10/2010 | Ho |
| 7,827,987 B2 | 11/2010 | Woodard et al. |
| 7,827,990 B1 | 11/2010 | Melidis et al. |
| 7,841,345 B2 | 11/2010 | Guney et al. |
| 7,856,698 B2 | 12/2010 | Hays |
| 7,856,980 B2 | 12/2010 | Lang et al. |
| 7,856,982 B2 | 12/2010 | Matula, Jr. et al. |
| 7,861,715 B2 | 1/2011 | Jones et al. |
| 7,874,293 B2 | 1/2011 | Gunaratnam et al. |
| 7,878,199 B2 | 2/2011 | Ging et al. |
| 7,882,837 B2 | 2/2011 | Kwok et al. |
| 7,900,635 B2 | 3/2011 | Gunaratnam et al. |
| 7,942,148 B2 | 5/2011 | Davidson et al. |
| 7,942,149 B2 | 5/2011 | Gunaratnam |
| 7,967,013 B2 | 6/2011 | Ging et al. |
| 7,967,014 B2 | 6/2011 | Heidmann et al. |
| 7,992,559 B2 | 8/2011 | Lang et al. |
| 8,042,538 B2 | 10/2011 | Ging et al. |
| 8,042,546 B2 | 10/2011 | Gunaratnam et al. |
| 8,051,850 B2 | 11/2011 | Kwok et al. |
| 8,091,553 B2 | 1/2012 | Bordewick et al. |
| 8,113,203 B2 | 2/2012 | Lithgow et al. |
| 8,136,524 B2 | 3/2012 | Ging et al. |
| 8,186,348 B2 | 5/2012 | Kwok et al. |
| 8,186,352 B2 | 5/2012 | Gunaratnam et al. |
| 8,210,180 B2 | 7/2012 | Gunaratnam |
| 8,220,459 B2 | 7/2012 | Davidson et al. |
| 8,230,855 B2 | 7/2012 | Raje et al. |
| 2003/0019496 A1 | 1/2003 | Kopacko et al. |
| 2003/0034034 A1 | 2/2003 | Kwok et al. |
| 2003/0062048 A1 | 4/2003 | Gradon |
| 2003/0075180 A1 | 4/2003 | Raje et al. |
| 2003/0084904 A1 | 5/2003 | Gunaratnam |
| 2003/0089373 A1 | 5/2003 | Gradon |
| 2003/0196656 A1 | 10/2003 | Moore et al. |
| 2003/0221691 A1 | 12/2003 | Biener et al. |
| 2004/0045550 A1 | 3/2004 | Lang et al. |
| 2004/0045551 A1 | 3/2004 | Eaton |
| 2004/0094157 A1 | 5/2004 | Dantanarayana et al. |
| 2004/0112385 A1 | 6/2004 | Drew |
| 2004/0112387 A1 | 6/2004 | Lang et al. |
| 2004/0118406 A1 | 6/2004 | Lithgow et al. |
| 2004/0144386 A1 | 7/2004 | Frater et al. |
| 2004/0177850 A1 | 9/2004 | Gradon |
| 2004/0211428 A1 | 10/2004 | Jones, Jr. et al. |
| 2004/0216747 A1 | 11/2004 | Jones et al. |
| 2004/0226566 A1 | 11/2004 | Gunaratnam et al. |
| 2004/0255949 A1 | 12/2004 | Heidmann et al. |
| 2005/0098183 A1 | 5/2005 | Nash et al. |
| 2005/0199239 A1 | 9/2005 | Lang et al. |
| 2005/0211252 A1 | 9/2005 | Lang et al. |
| 2006/0081250 A1 | 4/2006 | Bordewick et al. |
| 2006/0118117 A1 | 6/2006 | Berthon-Jones et al. |
| 2006/0169286 A1 | 8/2006 | Eifler et al. |
| 2006/0191538 A1 | 8/2006 | Lang et al. |
| 2006/0201514 A1 | 9/2006 | Jones et al. |
| 2006/0219246 A1 | 10/2006 | Dennis |
| 2006/0254593 A1 | 11/2006 | Chang |
| 2006/0283461 A1 | 12/2006 | Lubke et al. |
| 2007/0044804 A1 | 3/2007 | Matula et al. |
| 2007/0137653 A1 | 6/2007 | Wood |
| 2007/0144525 A1 | 6/2007 | Davidson et al. |
| 2008/0072908 A1 | 3/2008 | Lang et al. |
| 2008/0178885 A1 | 7/2008 | Raje et al. |
| 2008/0257354 A1 | 10/2008 | Davidson et al. |
| 2008/0264421 A1 | 10/2008 | Kwok et al. |
| 2008/0314389 A1 | 12/2008 | Thomas et al. |
| 2009/0044808 A1 | 2/2009 | Guney |
| 2009/0050156 A1 | 2/2009 | Ng et al. |
| 2009/0126739 A1 | 5/2009 | Ng et al. |
| 2009/0139526 A1 | 6/2009 | Melidis et al. |
| 2009/0173343 A1 | 7/2009 | Omura et al. |
| 2009/0223521 A1 | 9/2009 | Howard et al. |
| 2010/0000543 A1 | 1/2010 | Berthon-Jones et al. |
| 2010/0071700 A2 | 3/2010 | Hitchcock et al. |
| 2010/0089401 A1 | 4/2010 | Lang et al. |
| 2010/0282265 A1 | 11/2010 | Melidis et al. |
| 2010/0300447 A1 | 12/2010 | Biener et al. |
| 2011/0030692 A1 | 2/2011 | Jones et al. |
| 2011/0056498 A1 | 3/2011 | Lang et al. |
| 2011/0094516 A1 | 4/2011 | Chang |
| 2011/0174311 A1 | 7/2011 | Gunaratnam |
| 2011/0259337 A1 | 10/2011 | Hitchcock et al. |
| 2012/0174928 A1 | 7/2012 | Raje et al. |

FOREIGN PATENT DOCUMENTS

| | | |
|---|---|---|
| AU | 95/16178 B | 7/1995 |
| AU | 9459430 | 2/1996 |
| AU | A 32914/95 | 2/1996 |
| AU | A 41018/97 | 4/1998 |
| AU | A 89312/98 | 1/1999 |
| AU | 200071882 | 6/2001 |
| CA | 1039144 | 9/1928 |
| CA | 618807 | 4/1961 |
| CA | 623129 | 7/1961 |
| CA | 88122 | 11/1999 |
| CN | 1326371 | 12/2001 |
| CN | 2464353 | 12/2001 |
| CN | 1408453 | 4/2003 |
| DE | 284 800 C | 11/1913 |
| DE | 294 800 C | 11/1913 |
| DE | 459104 | 4/1928 |
| DE | 701 690 | 1/1941 |
| DE | 923 500 | 2/1955 |
| DE | 159396 | 6/1981 |
| DE | 3015279 | 10/1981 |
| DE | 3345067 | 6/1984 |
| DE | 37 07 952 | 3/1987 |
| DE | 3537507 | 4/1987 |
| DE | 3539073 | 5/1987 |
| DE | 4004157 | 4/1991 |
| DE | 42 12 259 | 1/1993 |
| DE | 42 33 448 | 4/1993 |
| DE | 4343205 | 6/1995 |
| DE | 195 48 380 | 7/1996 |
| DE | 196 03 949 | 8/1997 |
| DE | 29715718 | 10/1997 |
| DE | 19735359 | 1/1998 |
| DE | 297 21 766 | 3/1998 |
| DE | 29723101 | 7/1998 |
| DE | 29810846 U1 | 8/1998 |
| DE | 198 17 332 A1 | 1/1999 |
| DE | 49900269 | 1/1999 |
| DE | 198 07 961 | 8/1999 |
| DE | 198 08 105 A1 | 9/1999 |
| DE | 299 23 126 | 3/2000 |

| | | | | | | |
|---|---|---|---|---|---|---|
| DE | 299 23 141 | 3/2000 | | JP | 2002-543943 | 12/2002 |
| DE | 20005346 | 5/2000 | | JP | 2003-502119 | 2/2003 |
| DE | 29923141 U | 5/2000 | | JP | 2003-175106 | 6/2003 |
| DE | 200 17 940 | 12/2000 | | JP | 2003-190308 | 7/2003 |
| DE | 199 54 517 A1 | 6/2001 | | JP | 2004-32994 I | 11/2004 |
| DE | 199 62 515 | 7/2001 | | JP | 2005-506156 | 3/2005 |
| DE | 100 51 891 | 5/2002 | | JP | 3686609 | 8/2005 |
| DE | 10045183 | 5/2002 | | SE | 65 481 | 8/2000 |
| DE | 198 40 760 | 3/2003 | | WO | WO 80/01044 | 5/1980 |
| DE | 103 31 837 | 1/2005 | | WO | WO 80/01645 | 8/1980 |
| DE | 103 38 169 | 3/2005 | | WO | WO 82/03548 | 10/1982 |
| EP | 0 054 154 | 10/1981 | | WO | WO 86/06969 | 12/1986 |
| EP | 0 0252 052 | 1/1988 | | WO | WO 87/01950 | 4/1987 |
| EP | 0 264 772 | 4/1988 | | WO | WO 91/03277 | 3/1991 |
| EP | 0 334 555 | 9/1989 | | WO | WO 92/15353 | 9/1992 |
| EP | 0 386 605 | 2/1990 | | WO | WO 92/20395 | 11/1992 |
| EP | 0427474 | 5/1991 | | WO | WO 93/01854 | 2/1993 |
| EP | 0 462 701 | 12/1991 | | WO | WO 93/24169 | 12/1993 |
| EP | 0 303 090 B1 | 4/1992 | | WO | WO 94/02190 | 2/1994 |
| EP | 0 549 299 | 6/1993 | | WO | WO 94/16759 | 8/1994 |
| EP | 0 602 424 | 11/1993 | | WO | WO 94/20051 | 9/1994 |
| EP | 0 608 684 | 8/1994 | | WO | WO 95/02428 | 1/1995 |
| EP | 00697225 | 7/1995 | | WO | WO 95/04566 | 2/1995 |
| EP | 178925 A2 | 4/1996 | | WO | WO 96/17643 | 6/1996 |
| EP | 0 747 078 | 12/1996 | | WO | WO 96/25983 | 8/1996 |
| EP | 0821978 | 2/1998 | | WO | WO 96/39206 | 12/1996 |
| EP | 0 853 962 | 7/1998 | | WO | WO 97/00092 | 1/1997 |
| EP | 0 911 050 | 4/1999 | | WO | WO 97/07847 | 3/1997 |
| EP | 0 958 841 | 11/1999 | | WO | WO 97/09090 | 3/1997 |
| EP | 1027905 A2 | 8/2000 | | WO | WO 97/41911 | 11/1997 |
| EP | 1 057 494 | 12/2000 | | WO | WO 98/04310 | 2/1998 |
| EP | 1057494 A2 | 12/2000 | | WO | WO 98/11930 | 3/1998 |
| EP | 1099452 | 5/2001 | | WO | WO 9812965 | 4/1998 |
| EP | 1205205 | 11/2001 | | WO | WO 98/18514 | 5/1998 |
| EP | 1 163 923 | 12/2001 | | WO | WO/98/24499 | 6/1998 |
| EP | 1 334 742 | 8/2003 | | WO | WO 98/26829 | 6/1998 |
| EP | 1 356 843 | 10/2003 | | WO | WO 98/26830 | 6/1998 |
| EP | 1 555 039 | 7/2005 | | WO | WO 98/30123 | 7/1998 |
| ES | 145309 | 1/2000 | | WO | WO 9834665 | 8/1998 |
| FR | 780018 | 4/1935 | | WO | WO 98/48878 | 11/1998 |
| FR | 2 574 657 | 6/1986 | | WO | WO 99/21618 | 5/1999 |
| FR | 2 658 725 | 8/1991 | | WO | WO 99/30760 | 6/1999 |
| FR | 2 691 906 | 12/1993 | | WO | WO 9943375 | 9/1999 |
| FR | 2 720 280 | 12/1995 | | WO | WO 99/58181 | 11/1999 |
| FR | 2749176 | 12/1997 | | WO | WO99/58181 | 11/1999 |
| FR | 99/16 | 8/1999 | | WO | WO 99/61088 | 12/1999 |
| GB | 649 689 | 1/1951 | | WO | WO 99/65554 | 12/1999 |
| GB | 823 887 | 11/1959 | | WO | WO 00/21600 | 4/2000 |
| GB | 1395391 | 5/1975 | | WO | WO 00/35525 | 6/2000 |
| GB | 1467828 | 3/1977 | | WO | WO 00/38772 | 7/2000 |
| GB | 2145335 | 3/1985 | | WO | WO 00/50121 | 8/2000 |
| GB | 2147506 | 5/1985 | | WO | WO 00/57942 | 10/2000 |
| GB | 2 164 569 | 3/1986 | | WO | WO 00/69521 | 11/2000 |
| GB | 2 186 801 | 8/1987 | | WO | WO 00/78384 | 12/2000 |
| GB | 2 267 648 | 12/1993 | | WO | WO 0078381 | 12/2000 |
| GB | 2080119 | 12/1998 | | WO | WO 0078384 | 12/2000 |
| GB | 2080120 | 12/1998 | | WO | WO 01/62326 | 8/2001 |
| GB | 2080121 | 12/1998 | | WO | WO 01/97892 | 12/2001 |
| JP | S39-13991 | 7/1964 | | WO | WO 01/97893 | 12/2001 |
| JP | S48-55696 | 10/1971 | | WO | WO 02/07806 | 1/2002 |
| JP | S52-76695 | 6/1977 | | WO | WO 02/11804 | 2/2002 |
| JP | S52-164619 | 12/1977 | | WO | WO 02/32491 | 4/2002 |
| JP | S59-55535 | 4/1984 | | WO | WO 02/45784 | 6/2002 |
| JP | S61-67747 | 5/1986 | | WO | WO 02/47749 | 6/2002 |
| JP | H07-21058 | 4/1995 | | WO | WO 03/005931 | 1/2003 |
| JP | H07-308381 | 11/1995 | | WO | WO 03/035156 | 5/2003 |
| JP | H09-501084 | 2/1997 | | WO | WO 03/059427 | 7/2003 |
| JP | 09/216240 | 8/1997 | | WO | WO 03/082406 | 10/2003 |
| JP | H09-292588 | 11/1997 | | WO | WO 03/105921 | 12/2003 |
| JP | 11-000397 | 1/1999 | | WO | WO 2004/012803 | 2/2004 |
| JP | 1105649 | 2/1999 | | WO | WO 2004/021960 | 3/2004 |
| JP | H11-104256 | 4/1999 | | WO | WO 2004/022145 | 3/2004 |
| JP | H11-508159 | 7/1999 | | WO | WO 2004/022146 | 3/2004 |
| JP | H11-381522 | 11/1999 | | WO | WO 2004/022147 | 3/2004 |
| JP | 2000-135103 | 5/2000 | | WO | WO 2004022144 | 3/2004 |
| JP | 2000-279520 | 10/2000 | | WO | WO 2004022145 | 3/2004 |
| JP | 2000-325481 | 11/2000 | | WO | WO 2004/041342 | 5/2004 |
| JP | 2000-515784 | 11/2000 | | WO | WO 2004/073778 | 9/2004 |
| JP | 2002-028240 | 1/2002 | | WO | WO 2004/078228 | 9/2004 |

| | | |
|---|---|---|
| WO | WO 2004/096332 | 11/2004 |
| WO | WO 2005/002656 | 1/2005 |
| WO | WO 2005/018523 | 3/2005 |
| WO | WO 2005/028010 | 3/2005 |
| WO | WO 2005/063326 | 7/2005 |
| WO | WO 2005/063328 | 7/2005 |
| WO | WO 2005/068002 | 7/2005 |
| WO | WO 2005/094928 | 10/2005 |
| WO | WO 2005/123166 | 12/2005 |
| WO | WO 2006/000046 | 1/2006 |
| WO | WO 2006/074513 | 7/2006 |
| WO | WO 2006/074515 | 7/2006 |
| WO | WO 2006/074516 | 7/2006 |
| WO | WO 2006/138416 | 12/2006 |
| WO | WO 2007/045008 | 4/2007 |
| WO | WO 2007/048174 | 5/2007 |
| WO | WO 2009/026627 | 3/2009 |
| WO | WO 2009/052560 | 4/2009 |
| WO | WO 2009/062265 | 5/2009 |
| WO | WO 2009/108995 | 9/2009 |
| WO | WO 2010/066004 | 6/2010 |

OTHER PUBLICATIONS

Search Report issued in EP Application No. 09178736.6, Apr. 19, 2010.
U.S. Appl. No. 11/491,964, filed Jul. 25, 2006.
U.S. Appl. No. 11/128,399, filed Aug. 27, 2009.
U.S. Appln. No. 10/555,301, filed Feb. 1, 2006.
Supplementary Search Report cited in EP Appln. No. 04730413, mailed Sep. 29, 2009, 3 pages.
International Search Report of PCT/AU2004/000563, mailed Jun. 23, 2004.
Office Action dated Oct. 7, 2008, filed in Japanese Appln. No. 2003-537718 (English translation); 11 pages.
Decision Dated Dec. 6, 2007 (Received on Feb. 4, 2008;) Opposition hearing by Weinmann . . . against German Patent 101 51 984 (including English Translation of the Decision).
Various invoices relating to the "Somnomask," as well as a copy of a brochure of the model "Somnomask" of 1999.
Mask 1 Photographs, Respironics Inc., Reusable Full Mask (small), Part #452033, Lot #951108.
Mask 2 Photographs, Puritan—Bennett, Adam Circuit, Shell Part #231700, Swivel Part #616329-00, Pillows (medium), art #616324.
Mask 3 Photographs, DeVilbiss Healthcare Inc., Devilbiss Seal-Ring and CPAP Mask Kit (medium), Part #73510-669.
Mask 4 Photographs, Respironics Inc., Monarch Mini Mask with Pressure Port, Part #572004, Monarch Headgear, Part #572011.
Mask 5 Photographs, Healthdyne Technologies, Nasal CPAP Mask (medium narrow), Part #702510.
Mask 6 Photographs, Healthdyne Technologies, Soft Series Nasal CPAP Mask, Part #702020.
Mask 7 Photographs, DeVilbiss Healthcare Inc., Small Mask and Seal Rings, Part #73510-668.
Mask 8 Photographs, Respironics Inc., Reusable Contour Mask (medium), Part #302180.
Mask 9 Photographs, Healthdyne Technologies, Healthdyne Large Headgear.
Mask 10 Photographs, Respironics Inc., Soft Cap (medium), Part #302142.
Mask 11 Photographs, Weinmann: Hamburg, Nasalmaskensystem mit Schalldämpfer (medium), Part #WN 23105.
Mask 12 Photographs, Life Care.
Mask 13 Photographs, Healthdyne Technologies.
Mask 14 Photographs, King System.
Mask 15 Photographs, Respironics Inc., Pediatric Mask.
Mask 16 Photographs, Hans Rudolph Inc., Hans Rudolph Silicone Rubber Face Mask/8900.
Photograph of Weinmann Mask, acquired prior to 1998.
Somotron CPAP-Great WM 2300 Instruction Manual, Weinmann Hamburg, 11 pgs, 1991.
9 photographs of Weinmann mask, WM 23122 !991.
The ResMed Range of Mask Systems, product brochure, Nov. 1995, 4 pgs.
Product Brochure for ResMed "Sullivan® Mirage™—The Mirage is Real. A Perfect Fit—First Time," ©1997 ResMed Limited, 4 pages.
Product Brochure for ResMed "Sullivan® Mirage™—The Mirage is Real. A Perfect Fit—First Time," ©1998 ResMed Limited, 4 pages.
Nine (9) Photographs of Weinmann Mask, WM 23122, 1991.
4 additional photographs of "Weinmann Mask," before applicants' filing date.
Australian Appln. No. 2005253641—Examiner's First Report, dated Apr. 20, 2010.
Australian Appln. No. 2005253641—Examiner's Report, dated Aug. 18, 2011.
Australian Appln. No. 2005256167—Examiner's First Report, dated Apr. 29, 2010.
Australian Appln. No. 2006206044—Examiner's First Report, dated Dec. 1, 2010.
Australian Appln. No. 2010201443—Examiner's First Report, dated Jun. 22, 2011.
Australian Appln. No. 2010251884—Examination Report, dated Jul. 27, 2012.
Chinese Appln. No. 200410038106.7—Office Action (w/English translation), dated Jun. 15, 2007.
Chinese Appln. No. 200480011911.9—Office Action (w/English translation), dated Jun. 24, 2010.
Chinese Appln. No. 200480040220.1—Office Action English translation, before applicants' filing date.
Chinese Appln. No. 200580020203.6—Office Action (w/English translation), dated Jun. 1, 2010.
Chinese Appln. No. 200580020203.6—Office Action (w/English translation), dated Jul. 6, 2011.
Chinese Appln. No. 200580020203.6—Office Action (w/English translation), dated Dec. 23, 2011.
Chinese Appln. No. 200580020203.6—Office Action (w/English translation), dated Apr. 18, 2012.
Chinese Appln. No. 200580021230.5—Office Action (w/English translation), dated Jul. 3, 2009.
Chinese Appln. No. 200910223650.1—Office Action (w/English translation), dated Mar. 29, 2012.
Chinese Appln. No. 201010508994.X—Office Action (w/ English translation), dated Jun. 15, 2011.
Chinese Appln. No. 201010517066.X—Office Action (w/English translation), dated Nov. 10, 2011.
Chinese Appln. No. 201010620187.7—Office Action (w/English translation), dated Oct. 26, 2011.
Chinese Appln. No. 201010620187.7—Office Action (w/English translation), dated Jul. 10, 2012.
DeVilbiss Serenity Mask—Instruction Guide 9352 Series, before applicants' filing date.
DeVilbiss Serenity Mask—Mask Accessories, before applicants' filing date.
European Appln. No. EP 02445110.6—Search Report, dated Nov. 6, 2003.
European Appln. No. EP 03793491.6—Supplementary Search Report, dated Jun. 15, 2010.
European Appln. No. EP 04802114.1—Supplementary Search Report, dated Apr. 27, 2009.
European Appln. No. EP 05749447.8—Supplementary Search Report, dated Dec. 2, 2009.
European Appln. No. EP 05753870.4—Supplementary Search Report, dated Dec. 15, 2009.
European Appln. No. EP 05753870.4—Office Action, dated Jul. 19, 2010.
European Appln. No. EP 06704773.8—Supplementary Search Report, dated Mar. 29, 2011.
European Appln. No. EP 08161868.8—Search Report, dated Sep. 23, 2008.
European Appln. No. EP 09003544.5—Search Report, dated Jun. 2, 2009.
European Appln. No. EP 09178736.6—Search Report, dated Apr. 19, 2010.
European Appln. No. EP 10166255.9—Search Report, dated Oct. 25, 2010.
European Appln. No. EP 10181516.5—Search Report, dated Jun. 13, 2012.

European Appln. No. EP 10182015.7—Search Report, dated Jun. 15, 2012.
European Appln. No. EP 10185071.7—Search Report, dated Dec. 6, 2010.
European Appln. No. EP 10185072.5—Search Report, dated Dec. 6, 2010.
European Appln. No. EP 10185073.3—Search Report, dated Dec. 6, 2010.
European Appln. No. EP 12165749.8—Extended Search Report, dated Oct. 10, 2012.
European Appln. No. EP 12165751.4—Extended Search Report, dated Oct. 8, 2012.
Japanese Appln. No. S52-164619—English translation of Figure 1, Dec. 1977.
Japanese Appln. No. 2000-029094—Office Action (w/English translation), before applicants' filing date.
Japanese Appln. No. 2001-504444—Office Action (w/English translation), dated Oct. 26, 2004.
Japanese Appln. No. 2003-559587—Office Action (w/English translation), dated Mar. 17, 2009.
Japanese Appln. No. 2004-137431—Office Action (w/English translation), dated Dec. 8, 2009.
Japanese Appln. No. 2004-569777—Office Action (w/English translation), dated Mar. 3, 2009.
Japanese Appln. No. 2005-004072—Office Action (w/English translation), dated Sep. 24, 2009.
Japanese Appln. No. 2006-504029—Office A545843ction (w/English translation), dated Nov. 10, 2009.
Japanese Appln. No. 2006-545843—Notice of Reasons for Rejection (w/English translation), dated Jun. 7, 2011.
Japanese Appln. No. 2007-515732—Office Action (w/English translation), dated Aug. 24, 2010.
Japanese Appln. No. 2007-515732—Office Action (w/English translation), dated Aug. 16, 2011.
Japanese Appln. No. 2007-515732—Office Action (w/English translation), dated Jun. 12, 2012.
Japanese Appln. No. 2007-516895—Office Action (w/English translation), dated Aug. 24, 2010.
Japanese Appln. No. 2007-550640—Office Action (w/English translation), dated Mar. 29, 2011.
Japanese Appln. No. 2007-550640—Office Action (w/English translation), dated Mar. 27, 2012.
Japanese Appln. No. 2008-318985—Office Action (w/English translation), dated Jun. 14, 2011.
Japanese Appln. No. 2010-268127—Notice of Reasons for Rejection (w/English translation), dated Jul. 10, 2012.
Japanese Appln. No. 2011-038110—Office Action (w/English translation), dated Aug. 14, 2012.
New Zealand Appln. No. 556041—Examination Report, dated May 6, 2011.
New Zealand Appln. No. 564877—Examination Report, dated Dec. 2, 2009.
New Zealand Appln. No. 567375—Examination Report, dated Nov. 17, 2009.
New Zealand Appln. No. 587820—Examination Report, dated Sep. 13, 2010.
New Zealand Appln. No. 592219—Examination Report, dated Apr. 11, 2011.
New Zealand Appln. No. 597689—Examination Report, dated Jan. 25, 2012.
PCT/AU03/01160—International Search Report, dated Oct. 8, 2003.
PCT/AU2004/001760—International Search Report, dated Jan. 12, 2005.
PCT/AU2004/001760—International Preliminary Report on Patentability, dated Jul. 3, 2006.
PCT/AU2004/001813—International Search Report, dated Mar. 7, 2005.
PCT/AU2004/001813—International Preliminary Report on Patentability, dated Jul. 3, 2006.
PCT/AU2005/000850—International Search Report, dated Aug. 12, 2005.
PCT/AU2005/000850—International Preliminary Report on Patentability, dated Dec. 20, 2006.
PCT/AU2005/000931—International Search Report, dated Jul. 19, 2005.
PCT/AU2005/000931—International Preliminary Report on Patentability, dated Dec. 28, 2006.
PCT/AU2006/000037—International Search Report, dated Mar. 17, 2006.
PCT/AU2006/001570—International Search Report, dated Jan. 5, 2007.
PCT/AU2009/000241—International Search Report, dated May 18, 2009.
PCT/AU2009/001102—International Search Report, dated Dec. 11, 2009.
PCT/AU2010/000657—International Search Report, dated Sep. 9, 2010.
PCT/EP2004/012811—International Search Report, dated Apr. 12, 2005.
ResCare Limited, "Sullivan™ Nasal CPAP System, Nose Mask Clip—User Instructions" 5/90, 1 p., before applicants' filing date.
ResMed Ltd., "Improving patient compliance with the ResMed Range of Mask Systems the Ultimate Interface for CPAP treatment," before applicants' filing date, 4 pages.
ResMed, Mask Systems Product Brochure, Sep. 1992, 2 pages.
Respironics, Inc., "Nasal Mask System Silicone Contour Mask," Product Instructions, Jun. 1997, 2 pages.
U.S. Appl. No. 12/083,779—Office Action, dated Feb. 17, 2012.
U.S. Appl. No. 12/083,779—Office Action, dated Sep. 28, 2012.
U.S. Appl. No. 60/227,472, filed Aug. 2000 (expired).
U.S. Appl. No. 60/424,696, filed Nov. 8, 2002 (expired).
U.S. Appl. No. 60/467,572, filed May 2003 (expired).
U.S. Appl. No. 60/643,121, filed Jan. 12, 2005 (expired).

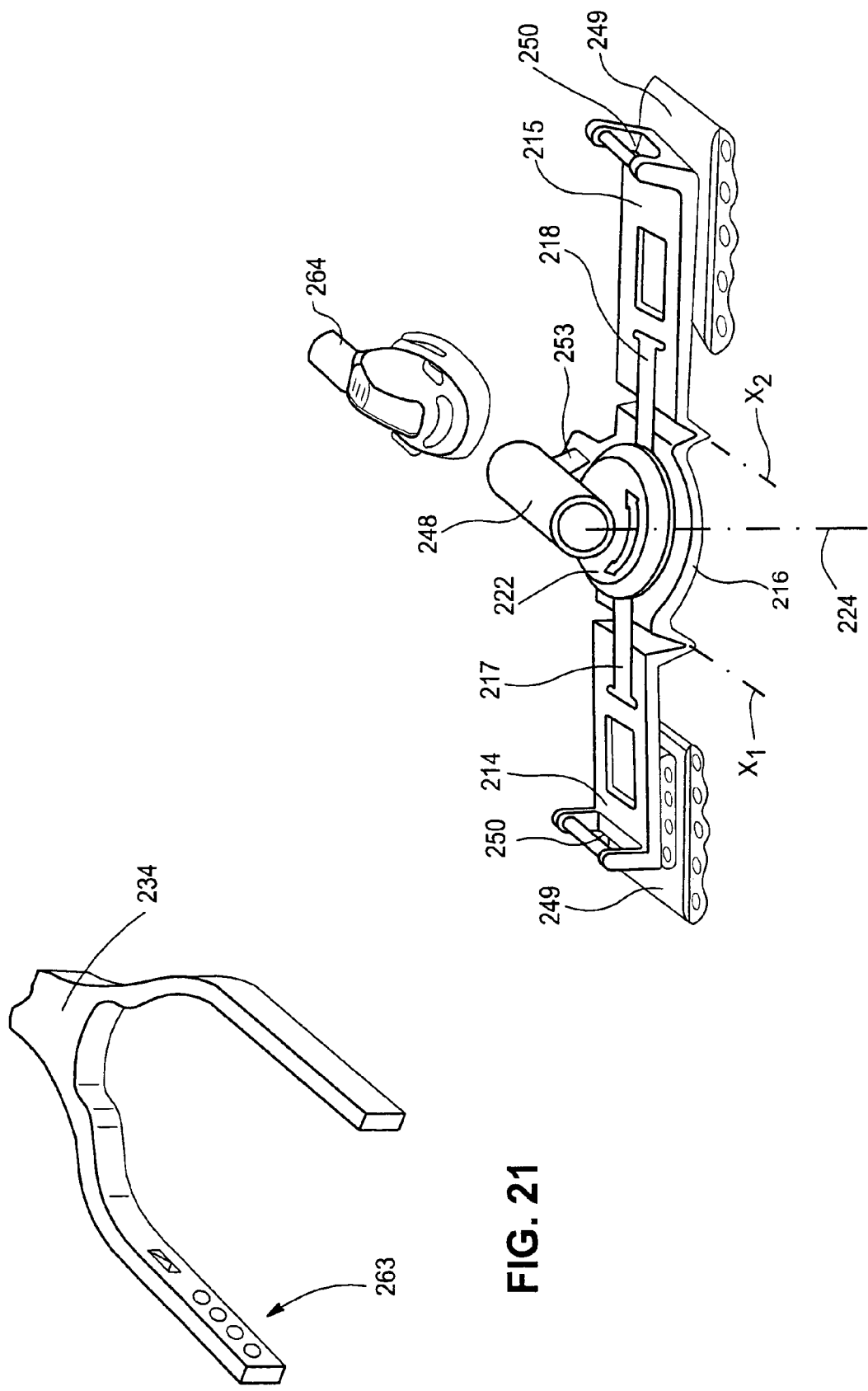

BREATHING MASK ARRANGEMENT AS WELL AS AN APPLICATION DEVICE AND A FOREHEAD SUPPORT DEVICE FOR SAME

CROSS-REFERENCES TO RELATED APPLICATIONS

This application is a continuation of U.S. application Ser. No. 11/987,164, filed Nov. 28, 2007, U.S. Pat. No. 7,992,559, which is a continuation of U.S. application Ser. No. 10/493,424, filed Apr. 22, 2004, now U.S. Pat. No. 7,320,323, which is the US national phase of international application PCT/EP02/11798, filed in Deutsch on 22 Oct. 2002, which designated the US. PCT/EP02/11798 claims priority to DE Application No. 101 51 984.2 filed 22 Oct. 2001, DE Application No. 102 01 682.8 filed 17 Jan. 2002 and WO Application No. PCT/EP02/02877 filed 14 Mar. 2002. The entire contents of these applications are incorporated herein by reference.

FIELD OF THE INVENTION

The invention concerns a breathing mask arrangement as can be used for example in the context of CPAP-therapy for treating sleep-related breathing disorders. The invention further concerns a forehead support device for a breathing mask arrangement.

BACKGROUND OF THE INVENTION

In the context of what is referred to as CPAP-therapy a patient can be supplied by way of a breathing mask arrangement with a breathable gas, in particular ambient air at a pressure level which is above the ambient pressure level. The respiratory gas which is under pressure makes it possible to provide for pneumatic splinting of the upper respiratory tracts and thus to obviate any obstructions. In the course of implementing pressure respiration or CPAP-therapy the breathing mask arrangements which are required to supply the respiratory gas are usually worn by the patient over the entire sleep or rest phase of the patient. The breathing mask arrangement is usually supported by way of a sealing lip zone in the region around the nose of the person using the mask and by way of a forehead support device in the forehead region of the mask user. The holding forces required to apply the breathing mask arrangement can be afforded by a fixing device which for example has a headband which is passed around the back of the head of the mask user. Under some circumstances, in the region in which the sealing lip device is applied and in the contact region of the forehead support device, surface pressures can occur, which result in the level of comfort involved in wearing the breathing mask arrangement being seriously adversely affected. In dependence on the individual architecture of the face of the person wearing the mask, considerable mask-pressing forces are in part required in order to achieve the desired sealing integrity. In that situation, in the region of the zones where the breathing mask bears against the face of the patient, unacceptably clearly visible pressure points may also be caused in the forehead region.

OBJECT OF THE INVENTION

The object of the invention is to provide a structure by which a breathing mask arrangement can be fixed in a correct application position and a high level of wearing comfort can be achieved. Attainment of the object in accordance with the invention In accordance with the invention that object is attained by a breathing mask arrangement comprising an arch body, a sealing lip means for bearing against the surface of the face of a mask user, a respiratory gas conduit means for feeding respiratory gas to a mask internal space which is defined by the arch body and which is in communication with the nose and/or mouth opening of the user of the mask, and an application structure for application of the sealing lip means jointly with the arch body, wherein the application structure has a carrier portion on which a respiratory gas conduit member is mounted.

In that way it is advantageously possible to provide a breathing mask arrangement which is of a robust structure and which can be cleaned in an advantageous manner and which is distinguished by a high level of sealing integrity.

In accordance with a particularly preferred embodiment of the invention the respiratory gas conduit member is in the form of a tube connection. Such a tube connection is preferably made from dishwasher-resistant plastic material so that the respiratory gas conduit member can be cleaned at comparatively high temperatures and in the process sterilised. The tube connection is preferably of such a configuration that its inside diameter is in the range of 12 to 34 mm. The tube connection can be of a substantially circular or preferably polygonal cross-section. The tube connection can be in the form of a conduit bend which provides for a slight change in direction of the flow of respiratory gas through an angle in the range of from 0 to 45°.

The conduit member which in particular is in the form of a tube connection is preferably releasably mountable to the carrier portion. A latching device is preferably provided for coupling the respiratory gas conduit member to the carrier portion. In accordance with a particular aspect of the present invention that latching device is advantageously in the form of a bayonet or rotational latching device.

The application structure of the breathing mask arrangement advantageously includes a frame portion which can be releasably coupled to the sealing lip means and/or to the arch body. Preferably the frame portion is designed in such a way that it embraces the arch body in a ring or loop configuration. The carrier portion is advantageously made from a plastic material and is provided with holding members, by way of which the carrier portion can be coupled for example to a lower web band arrangement of a headband. Advantageously those holding members are in the form of holding loops or clips, through which an end portion of the above-mentioned lower web band arrangement can be passed. The holding loops are preferably formed integrally with the carrier portion. The internal peripheral wall of a through opening formed by the holding loops is preferably of a configuration which, in regard to the moulding tool, permits removal of the holding loops from the mould without involving the use of a sliding pusher member.

The carrier portion provided for fixing the respiration gas conduit member is advantageously formed integrally with the frame portion. In that respect the carrier portion is advantageously designed in such a way that it has an insert opening into which the respiratory gas conduit member can be releasably inserted. The carrier portion is preferably arranged in such a way that it extends substantially perpendicularly to a frame surface defined by the frame portion.

In the region of the insert opening, the carrier portion preferably forms those coupling structures which can be brought into engagement with the respiratory gas conduit member which is in the form of the tube connection.

The arch body preferably comprises a coupling portion, by way of which the arch body can be sealingly connected to the respiratory gas conduit member. Preferably the arch body is produced from an elastomer material and fitted with elastic expansion thereof on to a portion of the tube connection, which is passed through the insert opening and which penetrates to the sealing lip means. Preferably, a peripheral bead or ridge is provided on that portion of the tube connection, which extends as far as the sealing lip means, by means of which peripheral bead the arch body and the tube connection are reliably held in the joined condition.

In accordance with a particularly preferred embodiment of the invention the arch body is formed integrally with the sealing lip means. In that way it is advantageously possible to avoid gaps or joints in the transitional region between the sealing lip means and the arch body. In addition it is advantageously possible for the sealing lip means and the arch body to be inserted in the form of an integral elastomer component into the frame portion.

In accordance with a particularly preferred embodiment, particularly reliable discharge of respiratory gas loaded with $CO_2$ to the ambient atmosphere is attained in that the arch body is provided with openings through which the respiratory gas which is under pressure in the internal region of the arch body can escape to the ambient atmosphere. The openings are preferably such that the cross-section thereof enlarges in the outlet direction. Those outlet openings are preferably arranged in such a way that they are disposed as closely as possible to the region which, in the position of application of the breathing mask arrangement, is adjacent to the nasal openings of a user of the mask.

In accordance with a particular aspect of the present invention the application structure includes a forehead support device for supporting the breathing mask arrangement in the forehead region of the user of the mask. The forehead support device is advantageously connected by way of a pivot device to the frame portion which embraces the arch body. By virtue of that configuration it is advantageously possible for the position of the forehead support device to be adapted to the individual facial architecture or structure of the user of the mask. Preferably the pivot device includes an arcuate track guide means by which the forehead support device can be variably positioned.

The respiratory gas conduit member which is preferably releasably couplable to the carrier portion advantageously forms a docking port which for example can also form part of a rotary coupling structure. It is possible to provide on the docking port further connecting devices, in particular small tube connections, by way of which for example a pressure measuring hose can be coupled to the breathing mask arrangement or possibly an additional supply of oxygen can be effected.

The forehead support device is preferably made from a thermoplastic material and provided with a forehead cushion means. The forehead cushion means is preferably formed by elastomer elements which are of a pad-like configuration and which can be coupled by way of a plug connecting structure to the receiving portion of the forehead support device, said receiving portion preferably being of a loop-like configuration. In that case the forehead support device is preferably designed in such a way that the elastomer elements can be fitted to the forehead support device at different locations. Preferably the elastomer elements are also of such a configuration that, by virtue of the way in which they are fixed to the loop portion, it is also possible to achieve different positions of the contact regions of the elastomer elements on the forehead of the user of the mask. The elastomer elements are preferably made from a silicone rubber material and in the region of their contact surface are so shaped that transmission of the contact forces to the surface of the forehead of the user of the mask takes place under a physiologically well compatible surface pressure. That can be achieved in particular by the elastomer elements being provided, on a rear side remote from their contact side, with an eccentrically arranged support foot which permits a tilting movement of the contact portion which bears against the user of the mask.

Preferably, also provided on the loop portion are coupling portions which permit coupling of the forehead support device to an upper forehead band arrangement of a headband. Those coupling portions can be in the form of a band strip. It is also possible for the forehead support device to be fixed for example by way of a hook-and-loop fastener to a preferably cushioned forehead band arrangement.

In accordance with a further aspect of the invention, another object of the invention is to prevent the occurrence of any pressure points in the forehead region in connection with the use of breathing masks.

In accordance with the invention that object is attained by a forehead support device for a breathing mask comprising a contact element which is provided in the application position for bearing against the forehead region of a user of the mask, wherein there is provided a holding device for holding the contact element movably.

By virtue thereof it is advantageously possible to ensure that a breathing mask arrangement is supported in the forehead region of a patient under a markedly reduced surface pressure against the tissue of the patient. The mobility of the contact element, which is provided in accordance with the invention, means that it can automatically adapt to the individual curvature of the forehead region of the user of the mask. In that way it is further advantageously possible for the contact element to afford a large surface area, whereby it is advantageously possible to achieve a marked reduction in the surface pressure.

An embodiment of the forehead support device, which is preferred in accordance with a particular aspect of the present invention, is afforded in that the holder is in the form of a pivotal holder. That pivotal holder advantageously permits a tilting movement of the contact element about at least one axis substantially parallel to the usual contact orientation. That pivotal holder can preferably be formed by a pivot or hinge device which in accordance with a particularly preferred embodiment includes a ball joint. As an alternative thereto or also in combination with that configuration, it is possible for the pivot device to be formed by an elastomer structure. The range of movement of the holder of the contact element is preferably in the range of 10-30°. It is possible to take sufficient account of all possible forehead architectures within that angular range.

In accordance with a particular aspect of the present invention the contact element is formed from an elastomer material, for example a fully transparent or coloured silicone rubber material. Particularly in this embodiment the contact element is of a preferably pad-like or plate-like configuration. In that case, the contact element is preferably concavely inwardly curved in such a way that a defined distribution in terms of surface pressure is afforded when the contact element is applied to the surface of the forehead. In accordance with a particularly preferred embodiment of the invention that surface pressure is so selected that, within a predetermined spacing from the edge of the contact element, there is a substantially uniform surface pressure, with the surface pressure gradually decreasing outwardly in the edge region of the contact element.

In accordance with a particularly preferred embodiment of the invention the forehead support device includes a plurality of and preferably two mutually adjacently arranged contact elements. The contact elements are preferably arranged in such a way that in the application position of a breathing mask arrangement, they are positioned above the left and right eyebrows of the user of the mask. The two contact elements are preferably connected together by way of a flexible bridge or strap device. In that way, it is possible on the one hand to achieve a greater increase in the contact area while at the same time the possibility of the contact elements twisting relative to each other can be limited in a defined manner. Particularly in this embodiment the two contact elements are preferably formed integrally with each other. The configuration of the contact elements in a plan view is not limited to substantially circular external contours. For example it is also possible to adopt elliptical or other polygonal external contours.

The pivot device for pivotably movably mounting the respective contact element is preferably also formed integrally with the contact element. A defined pivot character can be achieved by virtue of suitable geometrical configuration of the pivot device.

The pivot device is preferably arranged in such a way that it is disposed on or at least near the line of action of a force which extends through a centre point in terms of surface pressure of the respective contact element. That still further promotes rendering the distribution of surface pressure uniform.

The contact elements are preferably profiled in such a way that the contact element is prevented from being applied by suction to the surface of the forehead of the patient. Suction of the forehead support device on the surface of the forehead of the patient can further also be obviated by the contact element being provided with through bores or also with passages, through which air can pass into an intermediate region between the contact element and the forehead of the user of the mask.

The ball joint structures advantageously provide for good adaptability to the horizontal and vertical configuration of the forehead of the user of the mask. The pivot device—in particular the ball joint means—can also be designed to be lockable. The pivot device can also preferably be tiltable in a particularly advantageous manner about given axes—in particular about a horizontal axis. The curvature of the contact element can be so selected that different radii of curvature are afforded in the horizontal and vertical directions. The radii of curvature are preferably smaller than the usual radii of curvature of a forehead.

As an alternative to ball joint structures it is also possible to adopt cardanic suspension means, for example by means of a pivot pin. The angle of pivotal movement of the pivot device is preferably limited to a predetermined abutment angle. The material properties of the contact element are preferably so selected that it has a substantially anti-bacterial action and possibly acts to promote the healing of wounds.

Advantageously, a cushion means, in particular a gel body cushion means, or also an air or liquid cushion means, can be provided in the region of the contact surface. In that case, by varying the amount of liquid, air or gel used, it is advantageously possible to adjust the position of the breathing mask relative to the user.

Advantageously the mounting position of the contact element is adjustably variable. As an alternative thereto—or also in combination with this feature—it is also possible to provide a plurality of coupling options so that it is possible to achieve varying spacings on the forehead, by suitable selective coupling. It is possible to implement coarse adjustment by for example two, preferably three or also more coupling options, and to implement preferably stepless fine adjustment within a limited fine adjustment range. It is possible to permit a plurality of permutation options, in which case the individual coupling permutations result in respectively different settings in terms of the spacing relative to the forehead. It is also possible to provide clamping structures, by means of which stepless adjustment of the spacing relative to the forehead is possible. The coupling means can be so designed that a defined adhesive location is achieved, so that a setting which is individually steplessly adapted is durably maintained by adhesive means.

In accordance with a particularly preferred embodiment of the invention a particularly high level of wearing comfort is achieved in that the surface portions of the contact element, which come into contact with the surface of the skin of the user of the mask, have a surface which is velvety matt. In accordance with a particularly preferred embodiment of the invention, at least in the region of the contact surface of the contact element, there is provided a surface structure for affording a self-cleaning effect. Such a surface structure may have for example lotus leaf surface structures. The contact element may also be provided with a gel body, at least in the region of the contact surface.

In accordance with a further aspect of the invention In accordance with the invention the object specified in the opening part of this specification is attained by an application device for a breathing mask arrangement comprising a forehead support device, wherein the forehead support device has a right arm element and a left arm element and the arm elements are provided with a contact portion provided for bearing against a left and right forehead zone respectively and each of the arm elements is arranged pivotably movably about a pivot axis.

That advantageously makes it possible for the breathing mask arrangement to be supported in the forehead region of the mask user by way of a forehead support device which can advantageously be adapted to different facial architectures.

In accordance with a particularly preferred embodiment of the invention there is provided an adjusting drive device for deflection of the arm elements into a predetermined pivotal position. The adjusting drive device is preferably designed in such a way that both arm elements are pivotable by way of the adjusting drive device simultaneously, that is to say at the same time. The adjusting drive device may include for example an adjusting wheel which, by way of a screw or spiral drive means, is in engagement with actuating members which are displaceable radially with respect to an axis of rotation of the pivot wheel.

Preferably the pivot axes of each of arm elements are directed in such a way that viewed in the application position in a front view, they extend transversely and in particular perpendicularly with respect to a transverse line joining the eyebrows. That advantageously makes it possible for the forehead support device to be precisely adapted to the curvature of the forehead of the user of the mask and thereby to precisely set the breathing mask which is held by the application device in the region of the contact zone of the sealing lip device, which contact zone crosses over the bridge of the nose.

In accordance with a particular aspect of the present invention each of the arm elements is pivotable about its own pivot axis associated therewith, wherein the pivot axes of the two arm members are spaced from each other at the level of a transverse line joining the eyebrows. The spacing of two pivot axes of the arm members is preferably between 10 and 50 mm at the level of the transverse line joining the eyebrows. The length of the arm members is between about 25 and 75 mm depending on the respective spacing of the pivot axes.

In accordance with a further aspect of the present invention, adaptability, which is still further increased in comparison with the above-described embodiment, of the forehead support device to the individual curvature of the forehead of the user of the mask, is achieved if the pivot axes of the arm members are inclined relative to each other through an angle α in the range of between 8 and 45° relative to each other. It is advantageously possible for the structure defining the pivot axes to be designed in such a way that the angle α of the pivot axes relative to each other is adjustably variable.

Preferably the pivot axes are established in such a way that, in relation to a front view of a user of the mask, they intersect in the region between the transverse line joining the eyebrows and the chin of the user of the mask. That affords particularly good compatibility in relation to the facial architectures which statistically predominantly prevail.

The pivot axes are preferably each defined by a respective hinge device. The hinge devices can be in the form of multi-part pivot arrangements or, in accordance with a particularly preferred embodiment of the invention, they can be in the form of film hinges. With that embodiment it is possible for the arm members and the hinge basic structures provided for pivotably mounting the arm members to be produced in one piece, that is to say integrally from a plastic material.

In accordance with a particular aspect of the present invention the adjusting drive device includes an adjusting wheel which is coupled by way of a spiral structure to actuating members by means of which the arm elements can be deflected into defined pivotal positions. The adjusting wheel is preferably mounted rotatably about an axis which in the application position of the application device is oriented substantially perpendicularly to the surface of the forehead of the patient. The adjusting wheel is preferably of a diameter in the range of between 20 and 50 mm and in the outside peripheral region it is provided with a profiling, preferably a fluted or grooved structure, which permits the reliable transmission of the finger forces required for rotating the adjusting wheel. The adjusting wheel is preferably arranged in an intermediate region between a respiratory gas conduit portion of the breathing mask arrangement and a base portion of the forehead support device. In that case it is possible for the finger forces which are required to rotate the adjusting wheel to be applied by way of the thumb and the index finger, in which case the respiratory gas conduit associated with the breathing mask arrangement is embraced by the fingers, by using the thumb and the index finger.

In accordance with a further aspect of the invention, in accordance with the invention the object thereof as set forth in the opening part of this specification is also attained by an application device for a breathing mask arrangement having a forehead support device, wherein the forehead support device has a right arm element and a left arm element and both arm elements are pivotably movably coupled to a breathing mask by way of a pivot axis, wherein the pivot axes extend substantially parallel to a transverse line which in the application position of the breathing mask arrangement joins the eyebrows of a user of the mask and there is provided an adjusting drive device for establishing the pivotal position of the arm elements.

In that way it is advantageously possible, by way of the forehead support device, to adjust the contact pressure of a zone of the sealing lip device, which passes across the bridge of the nose of a user of the mask.

BRIEF DESCRIPTION OF THE DRAWINGS

Further details and features of the invention will be apparent from the description hereinafter with reference to the drawings in which:

FIG. 21 shows a detail view of a holding portion of an application device, which is provided for coupling to a breathing mask arrangement, FIG. 22 shows a perspective view of an application device for a breathing mask arrangement as can be fitted for example onto a respiratory gas conduit portion of a breathing mask.

DETAILED DESCRIPTION OF THE DRAWINGS

Figure 1:
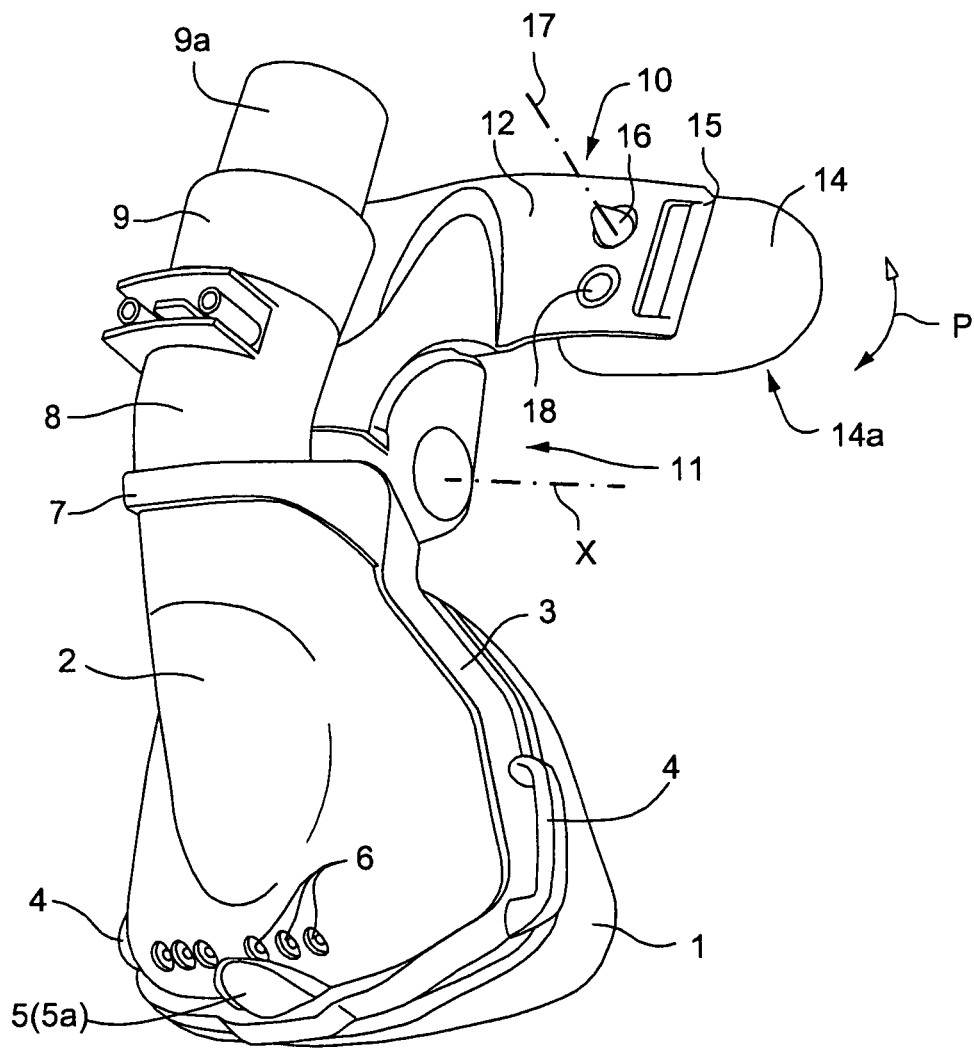
FIG. 1 shows a perspective view of a breathing mask arrangement according to the invention.

The breathing mask arrangement shown in FIG. 1 includes a sealing lip means 1 made from an elastomer material, in particular silicone rubber, and an arch body 2. The sealing lip means 1 is designed in such a way that it lines a receiving opening provided to receive the nose region of a user of the mask, and in that situation preferably passes across the bridge of the nose and the upper lip region of the user of the mask. In this case the sealing lip means 1 is of a substantially saddle-shaped silhouette. In this embodiment, the sealing lip means 1 and the arch body 2 are made in one piece from an elastomer material and are accommodated in a frame portion 3.

The frame portion 3 is made from a plastic material and has holding clips or loops 4 which are produced integrally therewith. In the application position of the breathing mask arrangement the holding loops 4 are disposed at cheek level or at the level of the sides of the nose of the user of the mask and permit coupling of a lower web band arrangement. For reliably coupling the arch body 2 to the frame portion 3, there is a retaining structure 5, by way of which the arch body 2 can be fixed to the frame portion 3 in the joining position by latching engagement therein. The retaining structure 5 includes a retaining nose 5a which engages over a top side of the frame portion 3.

Provided on the arch body 2 are a plurality of outlet openings 6 for the discharge of used respiratory gas to the ambient atmosphere.

The breathing mask arrangement further includes a carrier portion 7 which in this embodiment is formed integrally with the frame portion 3.

A respiratory gas conduit member which here is in the form of a docking port 8 is releasably fixed to the carrier portion 7. The docking port 8 includes an annular flange (not visible here) on to which a hose connecting sleeve 9 is rotatably movably fitted. The hose connecting sleeve 9 includes a hose connecting portion 9a on to which an end portion of a respiratory gas hose can be fitted.

The breathing mask arrangement according to the invention further includes a forehead support device 10 which is coupled movably to the frame portion 3 by way of an adjusting device 11.

The adjusting device 11 is of such a configuration that it permits a pivotal movement of the forehead support device 10 with respect to the frame portion 3 about the pivot axis X which is shown here. The adjusting device 11 includes a fixing mechanism, by which the forehead support device 10 and the frame portion 3 can be fixed in the selected relative position.

The forehead support device 10 includes a loop portion 12 to which forehead cushion elements 14 can be mounted. Provided on the loop portion 12, similarly to the frame portion 3, are holding loops or clips 15, for coupling the loop portion 12 to an upper web band arrangement of a headband provided for fixing the breathing mask arrangement in place.

The forehead cushion elements 14 are made from an elastomer material and, on their underside 14a which in the application position faces towards the user of the mask, form a contact surface involving a predetermined distribution in terms of surface pressure. The forehead cushion elements 14 are each coupled to the loop portion 12 by way of a respective push-in foot 16. The push-in foot 16 is provided eccentrically on the respective forehead cushion element 14 in such a way that pivoting the forehead cushion elements 14 about the axis 17 of the push-in foot, as indicated by the arrow P, makes it possible to achieve different contact positions for the underside 14a of the forehead cushion elements 14 on the surface of the forehead of the user of the mask. Different contact positions can be achieved by virtue of selection of the pivotal position of the forehead cushion element 14 and by virtue of selection of the receiving opening 18 provided to receive the push-in foot 16. In the embodiment illustrated here, two mutually spaced receiving openings 18 are provided in the loop portion 12, for each of the left and the right forehead cushion elements 14.

Figure 2:
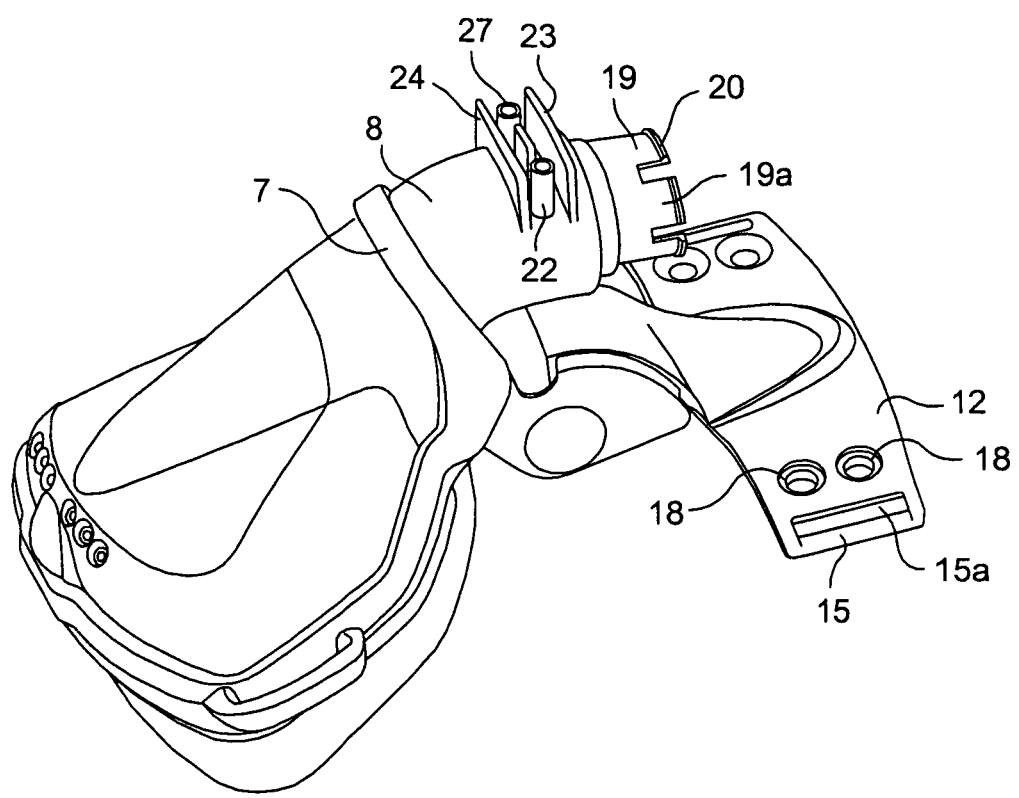
FIG. 2 shows a further perspective view of the breathing mask arrangement according to the invention without hose connecting sleeve.

The forehead cushion elements 14 can be removed from the loop portion 12 by pulling the push-in feet 16 out of the receiving openings 18, as is shown in FIG. 2. In this embodiment, the centre lines of the receiving openings 18 are spaced from each other by approximately 10 mm. The eccentricity of the push-in foot 16 on the respective forehead cushion element 14 (see in that respect FIG. 1) is also about 10 mm. As a result of the eccentric arrangement of the push-in foot 16 and the spaced arrangement of the receiving opening 18, heightwise variability of the forehead cushion elements in a range of about 30 mm is achieved substantially perpendicularly to a line joining the eyebrows of the user of the mask. A variation in the contact position over a range of 20 mm is also possible in a lateral direction, that is to say in the direction of the above-mentioned line which joins the eyebrows. The holding loop 15 provided for coupling an upper web band arrangement is arranged in the proximity of the receiving openings 18 in such a way that the through opening 15a defined by the holding loop is covered over towards the user of the mask by the forehead cushion element 14.

In the view shown in FIG. 2 the hose connecting sleeve 9 shown in FIG. 1 has been removed from the docking port 8. It is possible in this view to see an annular flange 19 which is formed integrally with the docking port 8 and which has a plurality of tongue elements 19a which are elastically deflectable towards the centre of the through passage formed by the docking port 8. Provided on the tongue elements 19a is a retaining bead or ridge 20 which can be brought into engagement with an internal peripheral groove provided in complementary relationship on the hose connecting sleeve 9. The geometry of the retaining bead 20, the internal peripheral groove in the rotational sleeve 9 and the elasticity of the tongue elements 19a are so matched that the hose connecting sleeve 9 can be withdrawn from the annular flange 19 without involving the use of a tool, when a given pulling force is exceeded. The annular flange 19 and the hose connecting sleeve 9 are also designed to fit in such a way that the hose connecting sleeve 9 is easily rotatably carried on the annular flange 19.

In this embodiment the docking port 8 is provided with hose connecting portions 21, 22, on to which a plug or hose element can be fitted. The hose connecting portions 21, 22 each form a respective through passage which opens into the respiratory gas passage formed in the docking port 8. When not in use, the hose connecting portions 21, 22 can be closed by a plug or cap element (not shown) which is preferably fitted in frictionally locking relationship on the hose connecting portions 21, 22. In this embodiment the hose connecting portions 21, 22 are arranged recessed in a groove which is delimited by two upstanding groove walls 23, 24. The docking port 8 is coupled to the carrier portion 7 by way of a plug-in connecting structure.

Figure 3:
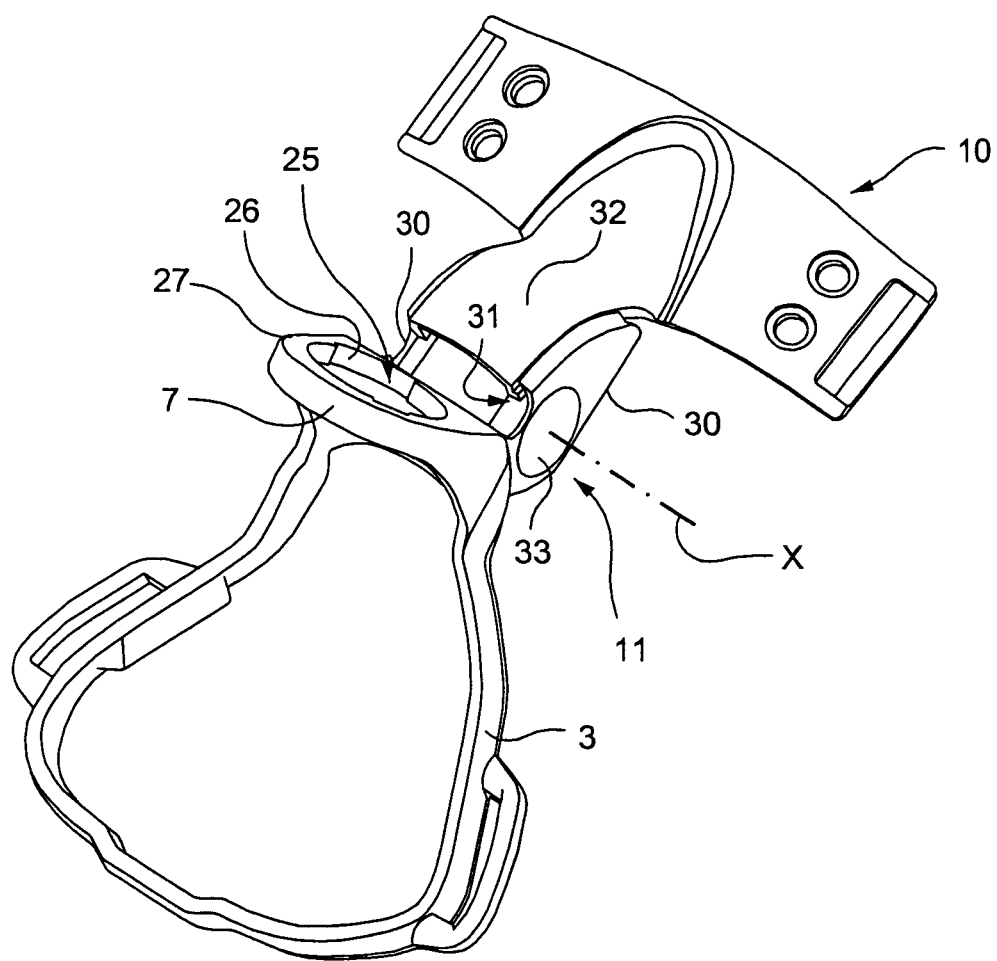
FIG. 3 shows a perspective view of the application structure of the previously illustrated breathing mask arrangement.

The retaining connecting structure for coupling the docking port 8 to the carrier portion 7, as can be seen from the view in FIG. 3, in this embodiment, is in the form of a rotary latching or bayonet connecting structure 25. The bayonet connecting structure 25 includes two mutually diametrally opposite retaining bridges 27 which are separated from each other by insertion recesses 26. In the locking position the retaining bridges 27 come into engagement with two retaining projections which are provided on a push-in flange portion 28 (FIG. 4) of the docking port.

The carrier portion 7 is formed integrally with the frame portion 3 and in that respect forms the insert opening which is provided to receive the insert connection 28 and which is partially lined by the retaining bridges 27. Provided in the transitional region between the carrier portion 7 and the frame portion 3 are two guide flanks 30 which are also provided integrally with the frame portion 3 and form part of the adjusting means 11. The guide flanks 30 form an arcuate guide means 31 in which a coupling portion 32 of the forehead support device 10 is displaceably guided. The arcuate guide means 31 and the region of the coupling portion 32, which is guided therein, are such that the forehead support device 10 and the frame portion 3 are movable relative to each other about the pivot axis X already shown in FIG. 1. Provided at the guide flanks 30 is an actuating zone 33, for applying a release force for moving the adjusting means 11 into a release position. The release force can be applied to the actuating zone in particular when gripping around the docking port 8 with the thumb and the index finger and applying the corresponding fingertips. As an alternative to the arcuate guide means 31 provided here, it is also possible for the adjusting means 11 to be of such a configuration that relative movement is made possible between the forehead support device 10 and the frame portion 3 along a path of movement which differs from an arcuate path. It is also possible to mount to the forehead support device 10 forehead cushion devices which in their structure differ from the forehead cushion elements 14 shown in FIG. 1.

Figure 4:
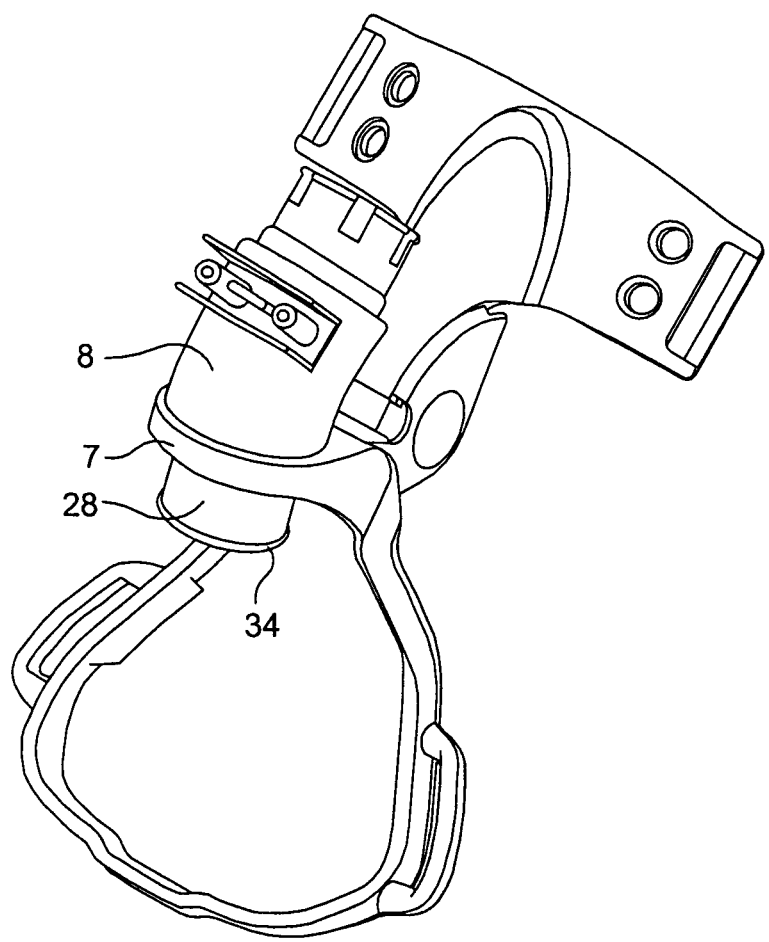
FIG. 4 shows a perspective view of the application structure with a docking port connected thereto.

FIG. 4 shows the application structure of the breathing mask arrangement according to the invention, in an assembly condition in which the docking port 8 according to the invention is inserted into the insert opening formed in the carrier portion 7 and correctly fixed in position by way of the bayonet closure device provided in the region of the insert opening. In this embodiment, the docking port 8 forms a conduit member which is in the nature of a pipe bend and by which the flow of respiratory gas flowing by way of the hose connecting sleeve 9 (FIG. 1) is diverted through an angle of about 30° towards the tip of the nose of the user of the mask. Feeding the respiratory gas in that way to the internal space in the mask, which is defined by the arch body 2 (FIG. 1), provides that the gas advantageously flows over the bridge of the nose of the user of the mask.

The modular structure of the breathing mask arrangement according to the invention makes it possible to implement a configuration of the breathing mask arrangement, which takes better account of the respective situation of use. The docking port 8 which is fitted into the carrier portion 7 has an insert connecting portion 28 which projects beyond the carrier portion 7 towards the frame portion 3. An insert opening portion of the arch body 2 can be fitted on to the insert connecting portion 28, with slight elastic expansion. Provided on the insert connecting portion 28 is a peripheral bead 34, by which the arch body 2 and the insert connecting portion 28 are held in a defined joint position. That peripheral bead 34 can come into engagement with an internal peripheral groove correspondingly provided in the arch body 2, or it can fit on an internal surface of the arch body 2. The carrier portion 7 and the docking port 8 are of such a configuration that the docking port 8 forms a respiratory gas conduit portion which bridges over the region of the bridge of the nose. That ensures that the field of vision is only slightly impaired.

Figure 5:
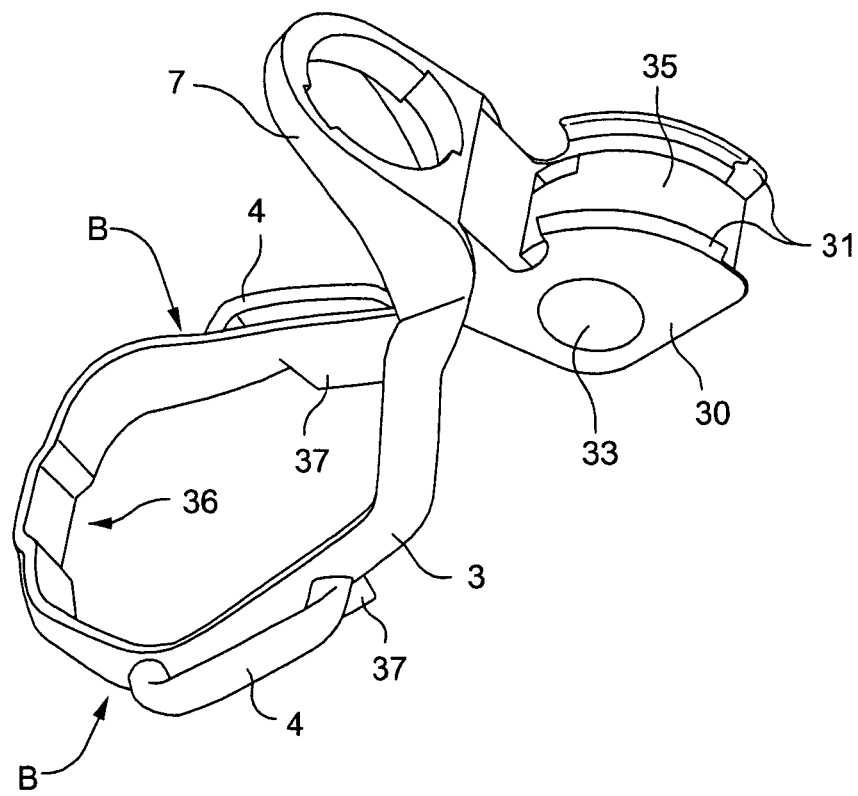
FIG. 5 shows a perspective view of an integral member formed from a carrier portion and a frame portion.

FIG. 5 shows a further perspective view of the integral member forming the frame portion 3. The guide flanks 30 which are made in one piece with the frame portion 3 are of such a configuration that application of a release force to the actuating zones 33 urges the guide flanks 30 away from each other in the region of the arcuate guide means 31. In the present embodiment, for that purpose, a lever/tilting effect is produced by an arcuate leg 35. The return movement of the guide flanks 30 in the region of the arcuate guide means 31 takes place as a consequence of the elasticity of the material involved. The fixing effect can be achieved by virtue of frictionally locking clamping of the contact zones of the coupling portion 32, which are guided between the guide flanks 30. As an alternative thereto or in combination therewith, it is also possible to achieve the fixing effect by coupling in positively locking engagement, for example by the adoption of a fine tooth arrangement.

Preferably, there is provided an abutment device which limits the maximum range of pivotal movement of the forehead support device 10 with respect to the frame portion 3. It is possible for that abutment device to be so designed that, for example by increasing the actuating forces applied to the actuating zone 33, the abutment device is moved into a condition in which the forehead support device 10 can be separated from the pivot structure connected to the frame portion 3.

The view illustrated in FIG. 5 also shows an outwardly recessed region 36 in the frame portion 3, which improves positioning and fixing of the arch body 2 in the frame portion 3. Positioning of the arch body 2 in the frame portion 3 is further promoted by two fixing plates 37 which are provided in the region of the holding loops 4 at the underside of the frame portion 3 and which engage into clamping pocket portions provided in the transitional region of the sealing lip means 1 in the arch body 2. The frame portion 3 is of a substantially saddle-shaped silhouette and attains its maximum width in a region of the frame portion 3, which in the application position of the breathing mask arrangement is approximately at the height of the sides of the nose of the user of the mask. The holding loops 4 extend upwardly from that zone B of maximum width to the region of the eyes of the user of the mask. The inward edges of the through openings which are bordered by the holding loops 4 are of a rounded configuration in order to prevent the band portions which are passed through those openings from possibly being chafed through. This view again shows the latching device adapted for fixing the docking port in the carrier portion 7.

Figure 6:
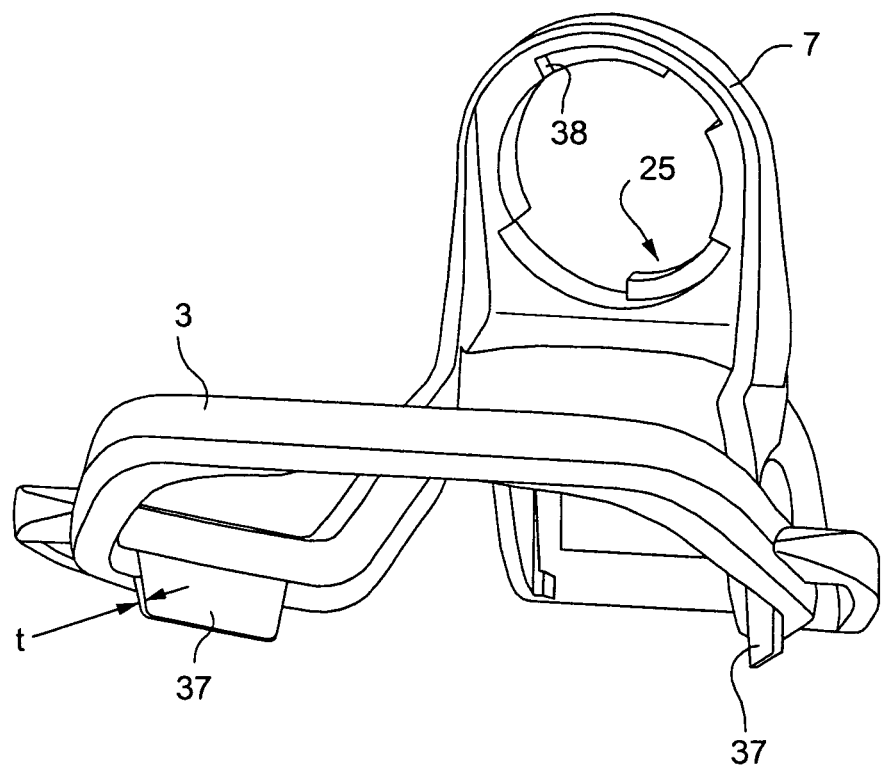
FIG. 6 shows a further perspective view of the integral member shown in FIG. 5 to describe the latching device provided for coupling the docking port.

FIG. 6 shows the fixing plates 37 which are provided at the underside of the frame portion 3, from another perspective. The fixing plates 37 are of a thickness t as measured transversely to the joining direction in the range of from 0.8 to 3 mm. The fixing plates are of a tapered configuration in the joining direction. The fixing plates 37 and in particular also the internal peripheral region of the frame portion 3, which region bears against the arch body 2, can be provided with a profiling which still further assists with coupling of the arch body. Preferably, fine profile grooves extending in the peripheral direction of the frame portion 3 are provided on the frame portion 3 and on the portion of the arch body 2, which bears there against.

The bayonet connecting structure 25 on the carrier portion 7 includes an end abutment 38 for defining the end position of the docking port 8 in the coupling position. In this embodiment the bayonet connecting structure 25 is designed in such a way that the maximum fixing force is achieved in the end position defined by the end abutment 38.

Figure 7:
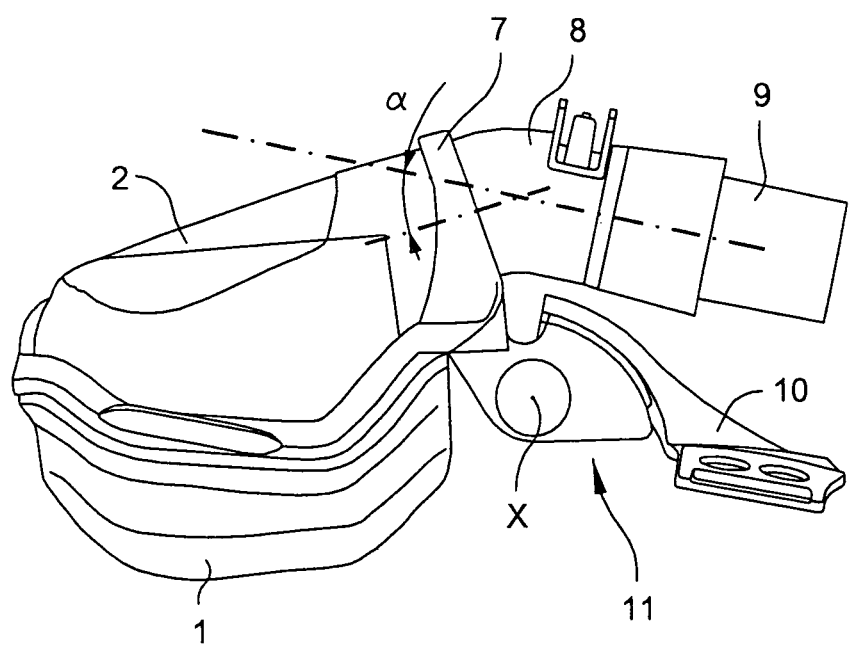
FIG. 7 shows a side view of the breathing mask arrangement according to the invention.

FIG. 7 shows the breathing mask arrangement according to the invention—with the exception of the forehead cushion elements 14 (FIG. 1)—in the completely assembled condition, from the direction of the pivot axis X. As can be seen in that view the docking port 8 which in accordance with the invention can be releasably inserted into the carrier portion 7 forms a coupling element for coupling the elastomer arch body 2 to a rotatably supported hose connecting sleeve 9, by which the feed flow of respiratory gas is deflected through an angle α which in this embodiment is 32°.

The docking port 8 can be selected from a set which includes a plurality of docking ports 8 and forms an interface member by which the arch body 2 can be coupled to different hose systems. Compatibility with different respiratory gas conduit systems can also be ensured by way of the hose connecting sleeve 9 which is fitted on to the docking port 8. It is possible to provide a plurality of sealing lip means which are respectively adapted to given types of faces and to achieve a configuration which is appropriate to the requirements involved, for the breathing mask arrangement according to the invention, in that an elastomer element which takes particularly good account of the individual facial architecture of the user of the mask and which comprises the sealing lip means 1 and the arch body 2 is integrated into the mask arrangement according to the invention. It is also possible to provide a plurality of variants of the forehead support device, which however are compatible with the adjusting means 11, and to fit the mask arrangement according to the invention with a variant of the forehead support device 10 which takes particularly good account of the individual facial architecture. As an alternative to the forehead cushion elements shown in FIG. 1, the forehead support device 10 may also be fitted with other kinds of forehead cushion devices for cushioned contact against the forehead of the user of the mask. It is possible to integrate cushion devices of that kind, for example into an upper forehead band arrangement, and to fit the forehead support device on to that cushioned forehead band arrangement, for example by way of a hook-and-loop fastener structure.

The invention is not limited to the preceding embodiment. By way of example, it is also possible to fit into the frame portion 3 which is designed in accordance with the invention, an arch body 2 which is not made from an elastomer material.

Figure 8:
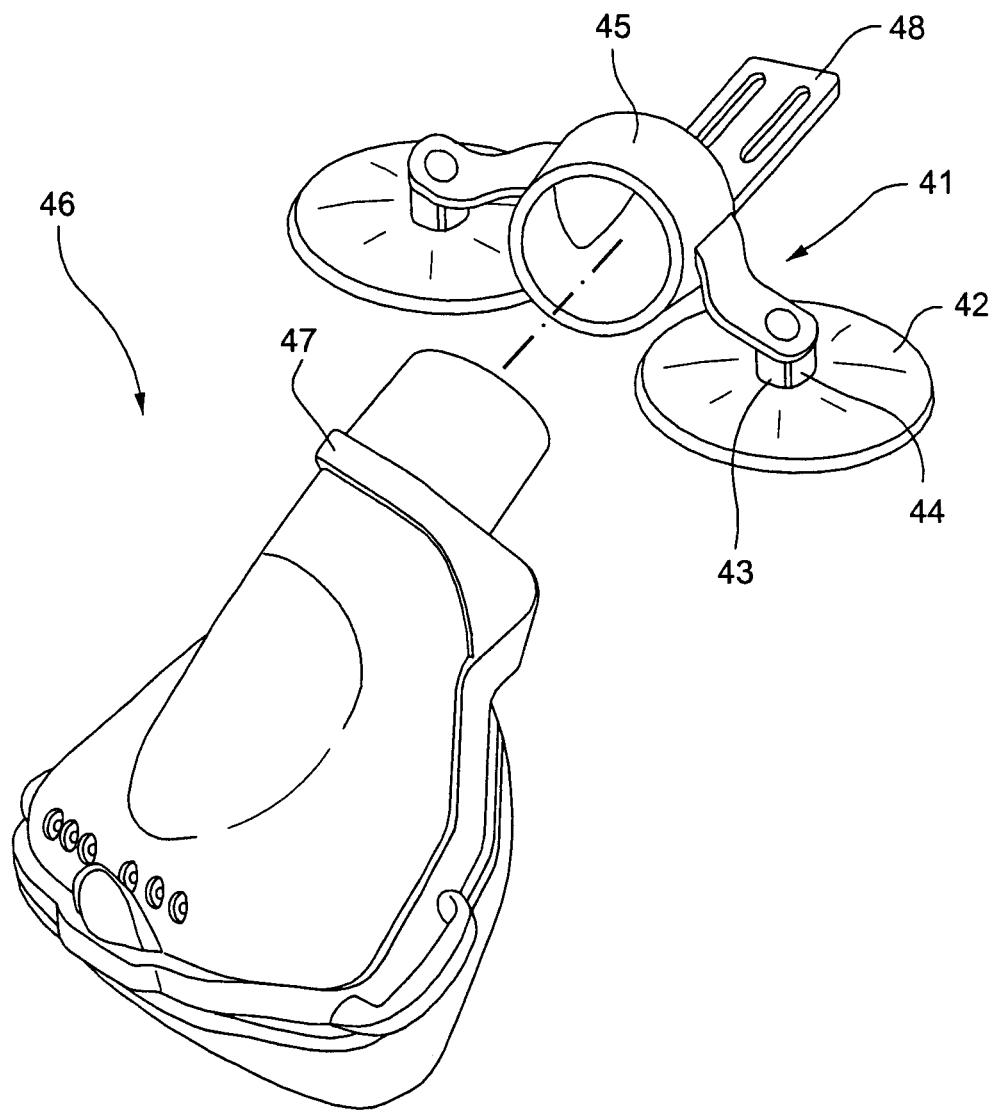
FIG. 8 shows a simplified perspective view of a forehead support device with two pivotably mounted pad-like contact elements and by way of indication a breathing mask.

The forehead support device shown in FIG. 8 has a holding device 41 for pivotably holding a contact element 42. The holding device 41 for that purpose includes a pivotable holder 43 which here has a plurality of fixing elements 44 which form part of a ball joint arrangement.

In the embodiment illustrated here, the contact element 42 is of a plate-like configuration and is formed from an elastomer material, here fully transparent silicone rubber. The contact element 42 is mounted tiltably about at least two axes in space by way of the fixing elements 44. In order to ensure as easy mobility as possible of the contact element 42, provided between the fixing elements 44 and a fixing shank portion (not visible) of the contact element 42 is a ring body which has a spherical external surface (details in relation thereto will be described more fully with reference to FIG. 9).

The holding device 41 further includes a coupling portion 45 for coupling the holding device 41 to a breathing mask 46.

In the embodiment illustrated here the coupling portion 55 is in the form of a ring-like element which can be fitted directly on to a connecting portion 47 of the breathing mask 46, the connecting portion 47 being of a correspondingly complementary configuration. In the embodiment illustrated here the holding device 41 is provided with a fixing portion 48 and can be connected by way thereof to a headband.

Figure 9:
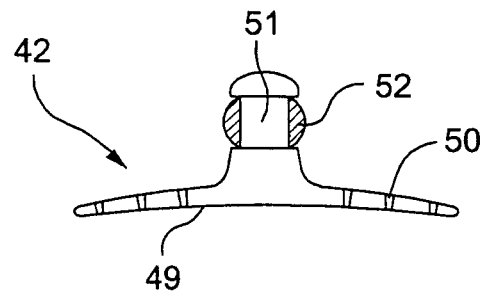
FIG. 9 shows a simplified sectional view to illustrate a preferred embodiment of a pivotably mounted contact element.

FIG. 9 shows a preferred embodiment of the contact element 42. The contact element 42 is formed from an elastomer material and has a contact surface 49 which is slightly concavely curved. The contact element 42 is provided with a plurality of fine through bores 50 through which pressure equalisation with the ambient atmosphere can be achieved in respect of the intermediate space possibly defined between the contact element 42 and the forehead of the patient. That advantageously prevents the contact element 42 from being sucked against the forehead region of the patient.

In the embodiment illustrated here the contact element 42 has a shank portion 51. Provided on the shank portion 51 is a ring element 52 which forms a spherical external surface. In conjunction with that ring element 52, this arrangement affords a comparatively easily movable ball joint device. As an alternative thereto it is also possible to forego the ring element and to provide the corresponding spherical portion directly on the shank portion 51 of the contact element 42.

Figure 10:
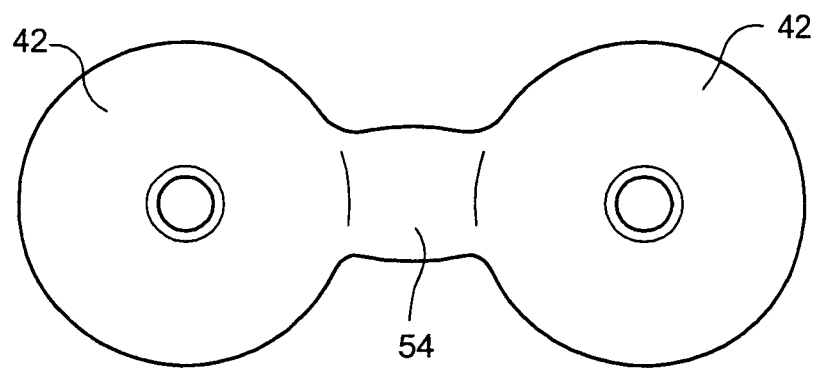
FIG. 10 shows a plan view of two contact elements which are formed integrally with each other, each of which is individually provided with a pivotal mounting means.

The embodiment of the invention shown in FIG. 10 has two contact elements 42 which are connected together by way of an integral central bridge or strap 54. The central strap 54 is so designed that it still permits pivotal movement and tilting movement of the two contact elements 42 relative to each other over a sufficient angular range. The spacing of the centres of the two contact elements 42 from each other preferably approximately corresponds to the distance between the eyes of the user of the mask.

Figure 11:
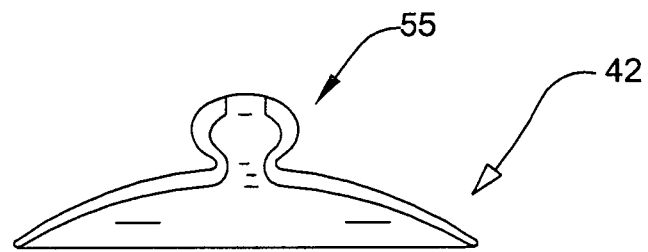
FIG. 11 shows a further embodiment of a contact element with a concavely curved contact surface and a part-spherical portion for pivotably mounting the contact element.

FIG. 11 shows a further embodiment of a contact element 42, in which case tiltability of the portion of the contact element, which forms the contact surface, is achieved by way of an elastomer structure 55 which here is formed integrally with the contact element 52. In the embodiment illustrated here the elastomer structure includes a substantially spherical internal space which can be fitted on to a spherical trunnion portion, with temporary elastic expansion. In the embodiment illustrated here the contact element also has a concavely curved base body which is flattened when the contact element is appropriately fitted in position.

Figure 12:
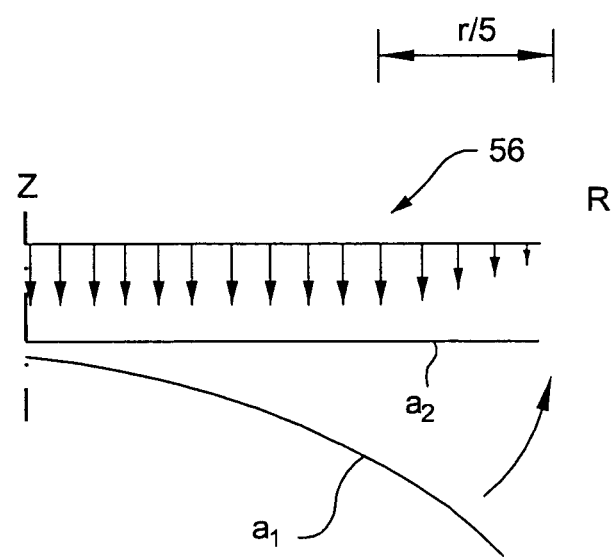
FIG. 12 shows a sketch to describe a preferred distribution of surface pressure from a central region of the contact element in its variation from a centre region of the contact element towards the edge region thereof.

The curvature of the base body of the contact element is preferably so selected that a defined distribution in terms of contact pressure is afforded when it is applied to a flat surface. That distribution in respect of contact pressure is shown by way of example in FIG. 12. The lower curved line a1 in this case symbolises the contact surface of the contact element in its initial position. The line a2 which is shown here as being straight symbolises the contact surface of the contact element 42, when appropriately deformed in the application position. The distribution in terms of surface pressure, which is indicated here in simplified form by an assembly of arrows 56, occurs in the context of deformation of the contact surface of the contact element. The distribution in terms of surface pressure is selected here in such a way that, starting from the centre Z towards the edge region, there is initially a substantially uniform distribution in terms of surface pressure, with the surface pressure gradually decreasing in the region of r/5 towards the edge R.

The invention is not limited to the embodiments described hereinbefore. For example, it is also possible, in a departure from the plate-shaped configuration selected here, for the forehead contact elements to be of a rectangular or polygonal configuration.

Figure 13:
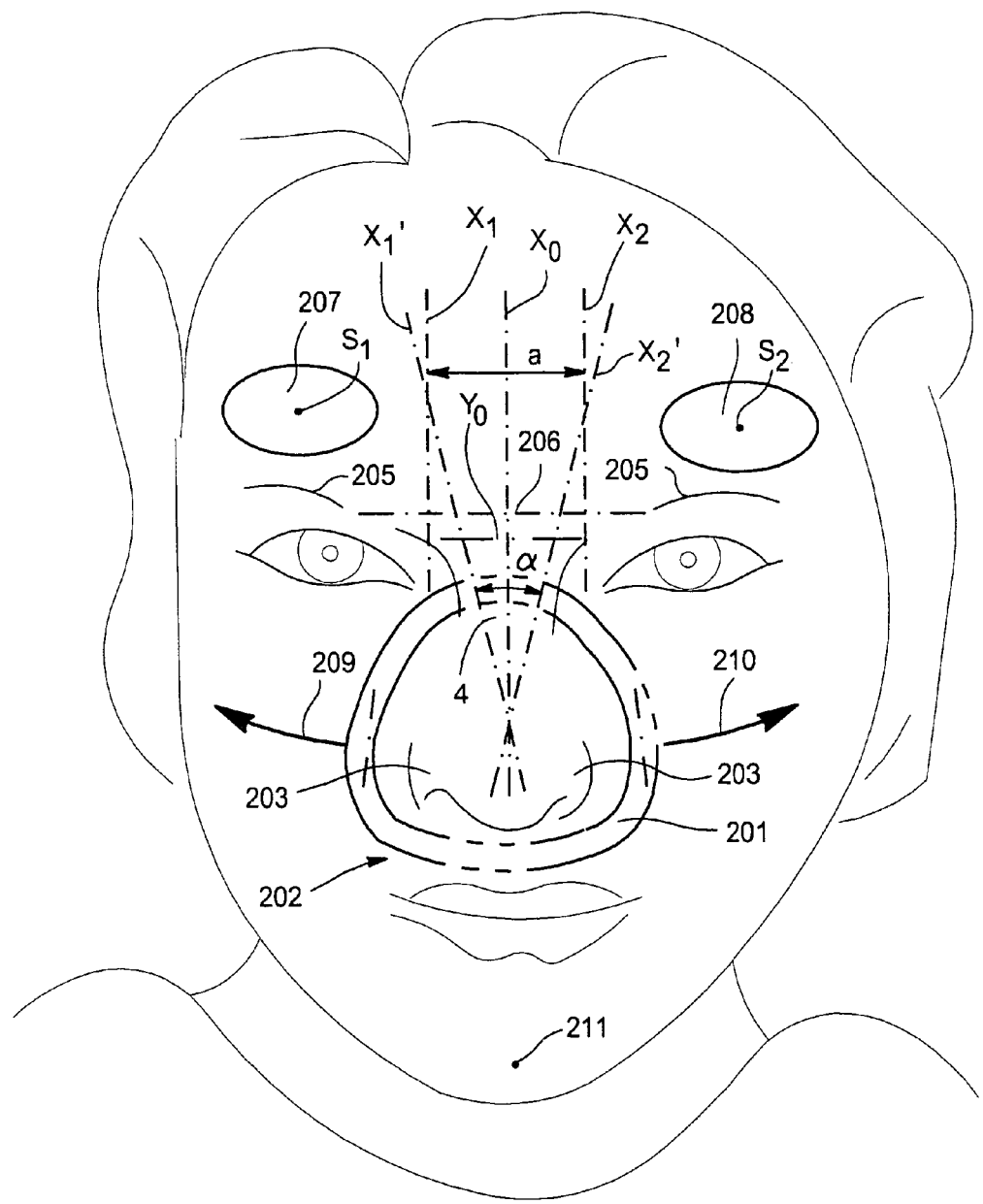
FIG. 13 shows a front view of the face region of a person to explain preferred contact zones of the forehead support device and preferred orientations of the pivot axes which are crucial in terms of pivotal mounting of the arm elements.

FIG. 13 shows a front view illustrating the surface of the face of a user of the mask. For application or fitting of a breathing mask arrangement it is applied for example to the face of the mask user in such a way that a sealing lip contact zone 201 defined by a sealing lip device of the breathing mask arrangement and the surface of the face of the mask user, starting from the upper lip region 202, extends around the nostrils 203 to the bridge of the nose 4 and preferably passes across same at the level of the eyes.

The breathing mask arrangement is supported on the forehead region of the mask user by way of a forehead support device which will be described in greater detail hereinafter. Preferably support on the forehead region is implemented by way of two contact zones 207, 208 which are disposed above a transverse line 206 which joins the eyebrows 205. In the view illustrated here support for the breathing mask arrangement in the forehead region is implemented at two contact zones 207, 208, wherein the spacing of the centroids S1, S2 of the contact zones 207, 208 preferably approximately corresponds to the spacing between the eyes of the mask user. The contact pressure of the sealing lip device of the breathing mask arrangement in the region of the sealing lip contact zone 201 is adjustably variable insofar as contact elements provided for affording contact in the contact zones 207, 208 are pivotable about pivot axes X0, X1, X1', X2, X2' and preferably also about a transverse axis Y0.

Support for the breathing mask arrangement on the face of the mask user can be implemented by the application device which is described in greater detail hereinafter, in such a way that the breathing mask arrangement and the forehead support device are supported on the face of the mask user substantially at three mutually spaced zones. In the forehead region in that case the forehead support device is supported at the contact zones 207, 208. The breathing mask arrangement is supported on the face of the mask user by way of the sealing lip contact zone 201. The fact that the application device and the breathing mask arrangement are supported on the face of the mask user at three main supporting zones advantageously provides that the breathing mask is supported in a statically defined manner. The holding forces required for holding the forehead support device in the forehead region are preferably applied by way of an upper headband arrangement. For fixing the breathing mask arrangement in the nose region, there is preferably a lower belt arrangement, by way of which the breathing mask arrangement is urged against the surface of the face of the mask user by pulling forces 209 and 210 which act thereon at both sides and which are directed laterally relative to the cheeks. The pulling forces 209, 210 are preferably applied by a lower belt arrangement which is passed around the region of the back of the head of the mask user.

The pivot axes X0, X1, X1', X2, X2' which permit adjustment of the support configuration of the forehead support device preferably extend directed away from the forehead region towards the upper lip region 202 of the user of the mask. The axes X1, X2 which are shown here are oriented in mutually parallel relationship and spaced from each other by a spacing a which substantially corresponds to the width of the bridge of the nose, in particular the width of the bridge of the nose in the region of the tear duct openings of the mask user.

The pivot axes X1', X2' which are inclined relative to each other here are also preferably spaced in the region of the width a of the bridge of the nose, at the level of the contact zones 207 and 208. The axes X1', X2' are inclined relative to each other at an angle α which is preferably so selected that the two axes intersect in the region between the base of the nose and the chin 211 of the mask user.

Figure 14:
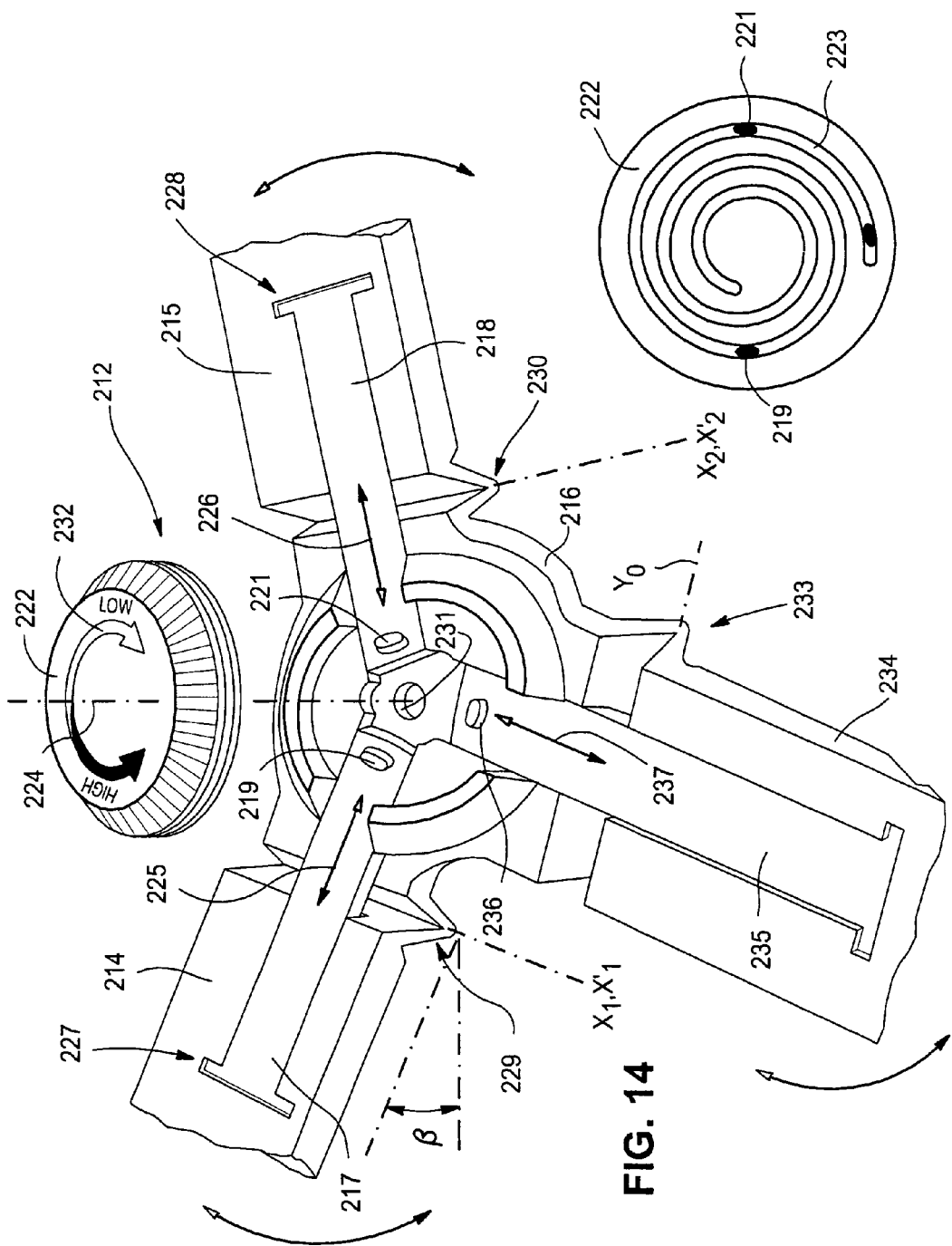
FIG. 14 is a perspective view to explain an adjusting drive device for adjustably pivoting the arm elements.

FIG. 14 as a perspective view shows an adjusting drive 212, by way of which the pivotal position of a left arm element 214 and a right arm element 215 can be altered adjustably with respect to a base portion 216.

In this case the adjusting drive 212 includes a coupling member 217 associated with the left arm element 214 and a coupling member 218 associated with the right arm element 215.

Each of the two coupling members 217, 218 is provided with at least one engagement portion 219, 221 which is in engagement with an adjusting wheel 222 which is shown here in a position of having been lifted off, by way of a spiral structure 223 provided at the underside of the adjusting wheel 222 (see the sketch at bottom right). By rotating the adjusting wheel 222 about its axis of rotation 224, the engagement portions 219, 221, as indicated by the arrow symbols 225, 226, are displaced in the radial direction jointly with the coupling members 217, 218.

In the illustrated embodiment the coupling members 217, 218 are coupled movably to the left and right arm elements 214, 215 respectively associated therewith. In the illustrated embodiment coupling of the coupling members 217, 218 to the arm elements 214, 215 associated therewith is effected in each case by way of a hinge portion 227 and 228 respectively which permits a pivotal movement of the coupling member 217, 218 with respect to the arm element 214, 215 associated therewith. The arm elements 214, 215 are coupled to the base portion 216 by way of a hinge connection 229, 230. The hinge connections 229, 230 are here in the form of film hinges. In this case the arm elements 214, 215 are formed integrally with the base portion 216. The hinge connections 229, 230 define the pivot axes X1, X1' and X2, X2' respectively referred to hereinbefore in connection with FIG. 1. As a consequence of the pair of forces applied to the respective arm element in the region of the hinge portions 227, 228 and the hinge connections 229, 230, the respective arm element can be moved with respect to the base portion 216 into a pivotal position which is defined by the radial spacing of the engagement portion 219, 221 from the axis of rotation 224. The maximum radial stroke movement of the engagement portions 219, 221 and the spatial position of the hinge portions and the hinge connections 227, 228, 229, 230 are so selected that, for example in a range of rotary movement of the adjusting wheel 222 through an angle of rotation of 540°, it is possible to adjust a pivot angle .beta. of the arm elements 214, 215 in the range of from 0 to 40°.

The adjusting wheel 222 is made from a plastic material and fitted by way of a central rotary trunnion or projection (not visible here) into a bore 231 provided in the base portion 216. Here the adjusting wheel 222 is of a diameter of 45 mm and on its outside it is provided with a marking 232 which indicates the adjusting effect achieved by rotating the adjusting wheel 222.

In the embodiment illustrated here the base portion 216 is coupled by way of a further hinge connection 233 to a holding portion 234. The hinge connection 233 illustrated here defines the pivot axis Y0 indicated in FIG. 13. The pivotal movement of the holding portion 234 with respect to the base portion 216 is effected in the same manner as described hereinbefore with respect to the left and right arm elements 214, 215 by way of a coupling member 235 which is in engagement with the adjusting wheel 222 by way of an engagement portion 236 and is movable in the radial direction with respect to the axis of rotation 224, as indicated by the arrow symbol 237. The holding portion 234 is connected to a mask base body portion of a breathing mask arrangement by way of an intermediate structure which is not shown in detail here.

Mounted to the left and right arm elements 214, 215 as will be described in greater detail hereinafter, are contact pads by way of which the arm elements 214, 215 bear against the contact zones 207, 208 (FIG. 13) of the mask user.

As will also be described in greater detail hereinafter, the arm elements 214, 215 can be pulled onto the forehead region of the mask user preferably by way of an upper headband arrangement.

Figure 15:
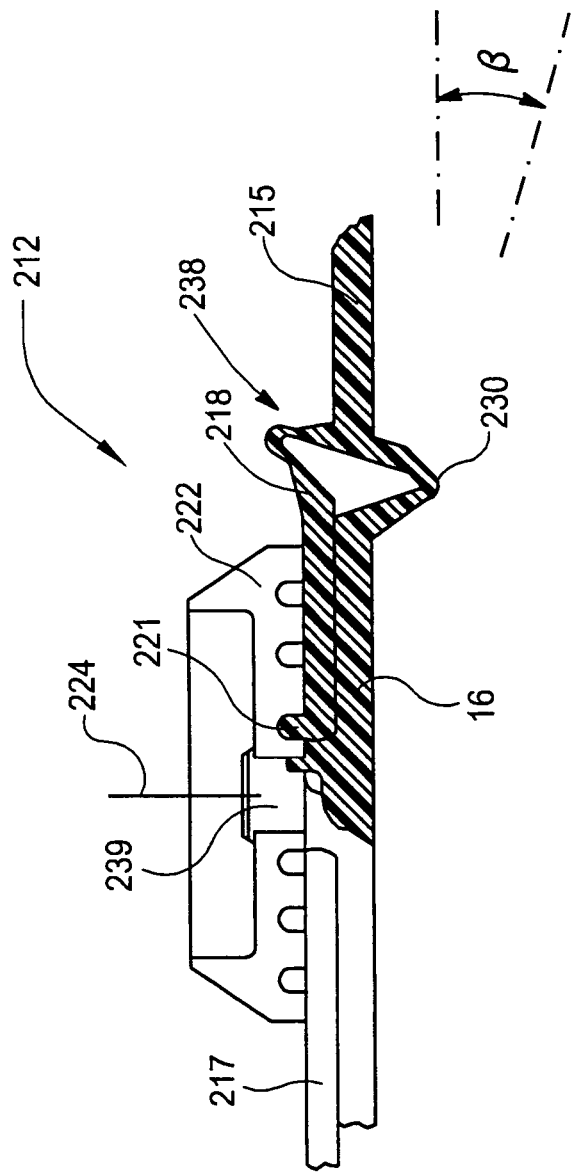
FIG. 15 shows a detail view to describe the structure of a variant of the adjusting drive, which is provided with film hinge structures.

FIG. 15 shows a further variant of the adjusting drive 212 in which a coupling member 218 which is movable radially relative to the axis of rotation 224 of the adjusting wheel 222 is formed in one piece with the arm element 215 associated therewith, in which case sufficient pivotal mobility is achieved by way of a film hinge structure 238. The base portion 216 is also formed in one piece with the arm element 215 and is coupled thereto similarly to the embodiment shown in FIG. 14 by way of a hinge connection 230 which is also in the form of a film hinge. The portions at which forces are applied, as defined by the film hinge structure 238 and the hinge connection 230, are spaced from each other in such a way that, as a consequence of the radial stroke movement of the coupling member 218 which can be adjusted by the adjusting wheel 222, it is possible to achieve an adequate pivotal angle .beta. of the arm element 215.

The adjusting wheel 222 is rotatably mounted on a rotary trunnion or projection 239 which stands up from the base portion 216. The underside of the adjusting wheel 222, which faces towards the base portion 216, has the spiral structures, like the above-described embodiment, which are in engagement with the engagement portion 221 provided integrally with the coupling member 218.

Figure 16:
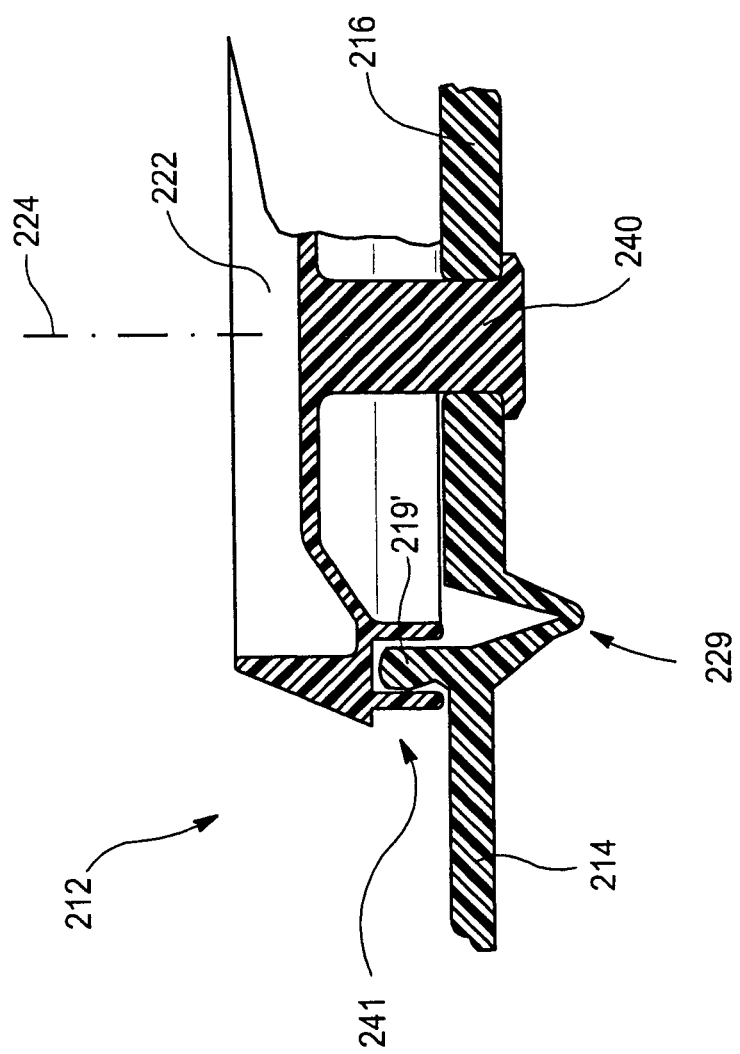
FIG. 16 shows a further detail view to describe an embodiment of the adjusting drive device also with a film hinge and a spiral groove region which is provided at an underside of the adjusting wheel and which is directly in engagement with an engagement portion of an arm element.

FIG. 16 sets out a further embodiment of the adjusting drive 212. In this case also the adjusting drive 212 includes an adjusting wheel 222 coupled rotatably to the base portion 216 by way of a rotary trunnion or projection 240. Provided on the underside of the adjusting wheel 222, which faces towards the base portion 216, is a spiral structure 241 which is directly in engagement with an engagement portion 219' provided on the arm element 214. The arm element 214 is pivotably movably coupled to the base portion 216 by way of a hinge connection 229 which in this case also is in the form of a film hinge. Rotation of the adjusting wheel 222 about the axis of rotation 224 defined by the rotary trunnion 214 makes it possible to set different spacings of the engagement portion 219' from the axis of rotation 224, whereby the arm element 214 is pivotable with respect to the base portion 216 into respectively desired pivotal positions.

Figure 17:
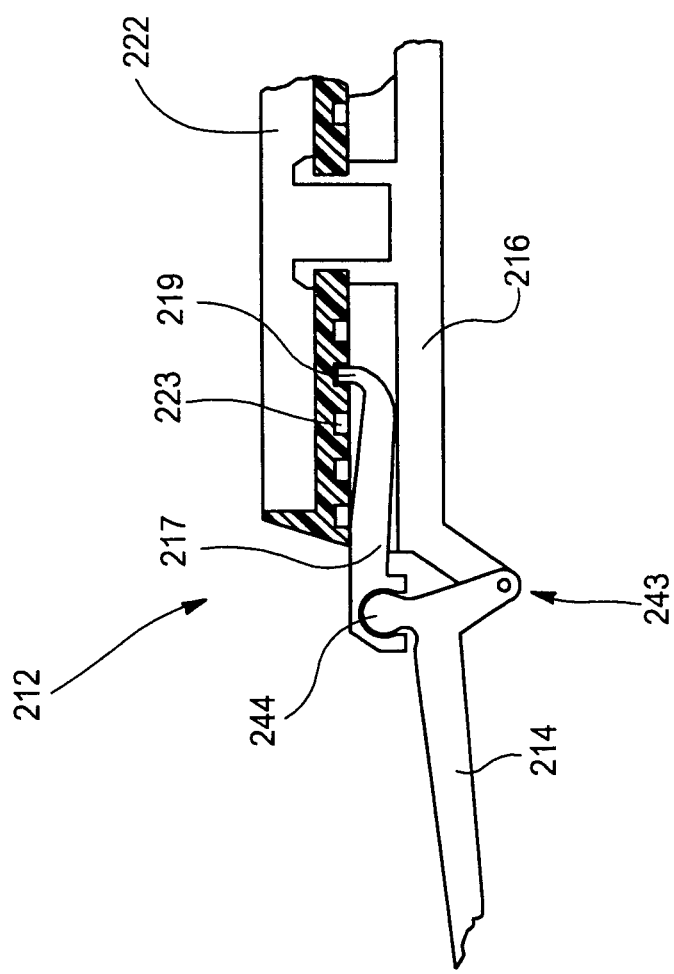
FIG. 17 shows a simplified view in section of a further embodiment of an adjusting drive device with an arm element which is mounted pivotably by way of a pivot pin zone.

FIG. 17 shows a further embodiment of an adjusting drive 212 according to the invention, in which the base portion 216 and the arm element 214 are in the form of separate parts which are coupled together by way of a hinge device 243. Provided on the arm element 214 is a knob 244 to which the coupling member 217 is pivotably mounted. Similarly to the embodiments described hereinbefore, the coupling member 217 has an engagement portion 219 which is in engagement with the adjusting wheel 222 by way of a spiral structure 223. By rotation of the adjusting wheel 222, the coupling member 217 can be displaced in a defined manner in the radial direction and, in so doing, pivots the arm element about the hinge device 243 into a defined angular position with respect to the base portion 216. It is possible to provide braking means, by which the adjusting wheel 222 is sufficiently firmly fixed in the desired rotational position. Braking devices of that kind can be embodied for example by fine latching or detent projections which come into and out of engagement respectively in the course of a relative movement of the components which are moved relative to each other, such movement being made possible by the inherent elasticity of the parts involved. It is also possible for the spiral structure to be designed in such a way that it is substantially self-locking.

Figure 18:
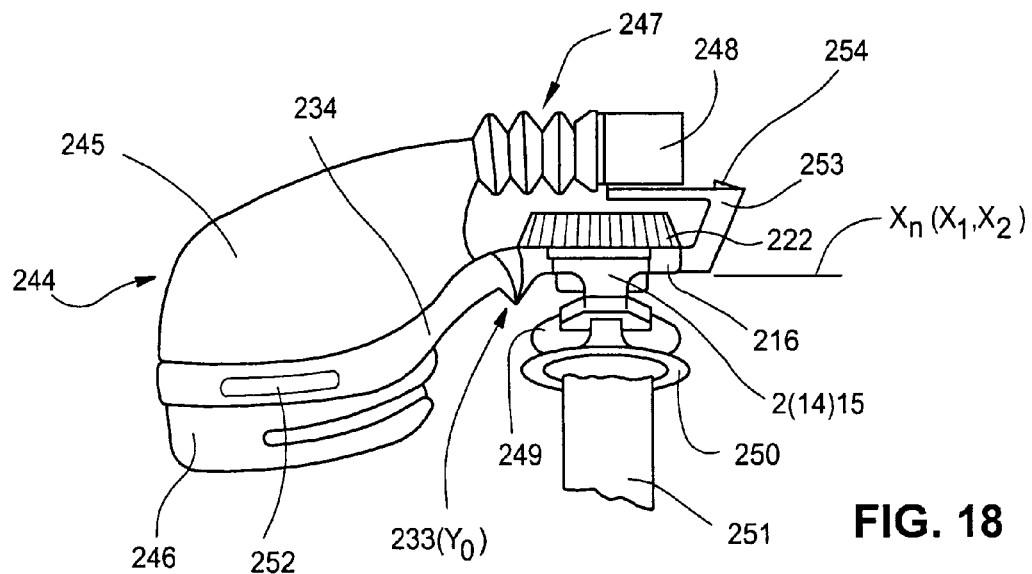
FIG. 18 shows a simplified side view of an application device provided with a breathing mask arrangement.

FIG. 18 shows an application device according to the invention with a breathing mask arrangement 244 accommodated therein. The breathing mask arrangement 244 includes a mask base body 245 and a sealing lip device 246 which is coupled thereto. The sealing lip device 246 is made from an elastomer material, preferably fully transparent silicone rubber, and in the application position sealingly contacts the sealing lip contact zone 201 of the mask user, as is shown in FIG. 13. The feed of the respiratory gas into the interior of the mask which is defined by the mask base body 245 is effected by way of a flexible conduit portion 247 which in the illustrated embodiment is also made from an elastomer material and is in the form of a bellows structure. Connected to the flexible conduit portion is a breathing hose connecting portion 248 which is of an inside diameter in the range of between 12 and 35 mm. The breathing hose connecting portion 248 is coupled to the base portion 216 of the forehead support device. The forehead support device 216 includes the adjusting wheel 222 which here is disposed in an intermediate region between the flexible conduit portion 247 or the breathing hose connecting portion 248 and the base portion 216. The adjusting wheel 222 can be turned by the user of the mask by gripping around the flexible conduit portion 247, by way of the fingertips of the thumb and the index finger of the user of the mask. Rotating the adjusting wheel 222 makes it possible for the arm elements 214 and 215 to be pivoted about the pivot axe Xn. In that way it is possible for a forehead pad 249 which is provided for making contact with the forehead region of the mask user to be adjustably positioned with respect to the base portion 216. Provided on the arm element 215 (214) is an eye portion 250, through which a portion of an upper headband arrangement 251 is passed.

In the embodiment illustrated here the base portion 216 is pivotably movably connected to a holding portion 234 by way of the hinge connection 233. The holding portion 234 is of a frame-like configuration and embraces the mask base body 245 at least in the side region thereof. Also provided on the holding portion 234 are eye portions 250 through which a portion of a lower headband arrangement (not shown) can be passed. As an alternative to the design configuration involving the eye portions 252 or also in combination therewith, it is possible to provide other coupling structures for coupling the holding portion 234 or the mask base body 245 to a headband arrangement.

Pivotal movement of the base portion 216 about the pivot axis Y0 which is defined by the hinge connection 233 is effected in this embodiment simultaneously with the pivotal movement of the arm members 214, 215 about the axes X1, X2.

The breathing hose connecting portion 248 is coupled to the base portion 216. In the present embodiment coupling is effected by way of a holding foot 253 which is guided past the adjusting wheel 222. The holding foot 253 is fitted onto a plug connecting portion of the base portion 216 and provided with a retaining device 254 by which an end portion of a respiratory gas conduit, which is coupled to the breathing hose connecting portion 248, is additionally fixed. The forehead pads 249 intended to bear against the forehead of the mask user are displaceably mounted to the respective arm element 214, 215.

Figure 19:
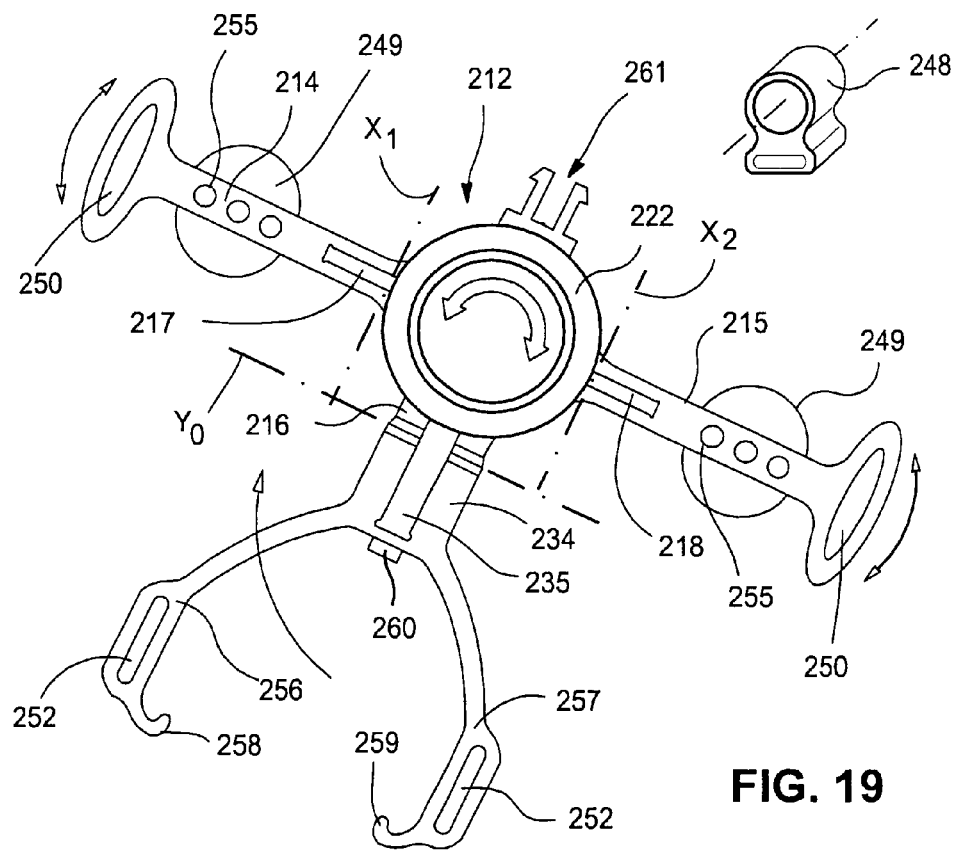
FIG. 19 shows a simplified perspective view of an application device with integrated forehead support device for the application of a breathing mask.

FIG. 19 shows an application device for a breathing mask, in which the left arm element 214, the right arm element 215 and the holding portion 234 can be tilted about the axes X1, X2 and Y0 respectively in a defined manner by way of the adjusting drive 212 which is actuable by an adjusting wheel 222. The tilting movement of those components is effected in each case by way of the coupling members 217, 218 and 235 which are associated with those parts. Support for the arm elements 214, 215 against the forehead region of a mask user is by way of the forehead pads 249 which have already been referred to with reference to FIG. 18 and which in this embodiment can be inserted into insert openings 255 provided on the respective arm elements 214 and 215.

In this case the holding portion 234 is made from a high-strength plastic material, preferably polyamide, and is of a frame-like configuration. The holding portion 234 includes two holding arms 256, 257 which are each provided with a respective eye portion 252 through which an end portion of a lower belt arrangement can be passed.

The holding arms 256, 257 are provided with an engagement structure 258, 259 by way of which the holding arms can be brought into engagement with a mask base body. Fixing of the mask base body in the holding portion 234 is further effected by a retaining or latching projection 260 which is formed integrally with the holding portion 234. Provided on a side of the base portion 216, which is remote from the holding portion 234, is a push-on portion 261, onto which a breathing hose connecting portion can be fitted. The breathing hose connecting portion 248, as indicated in FIG. 18, can serve to conduct the respiratory gas into the interior of the mask, as is defined by a mask base body.

Figure 20:
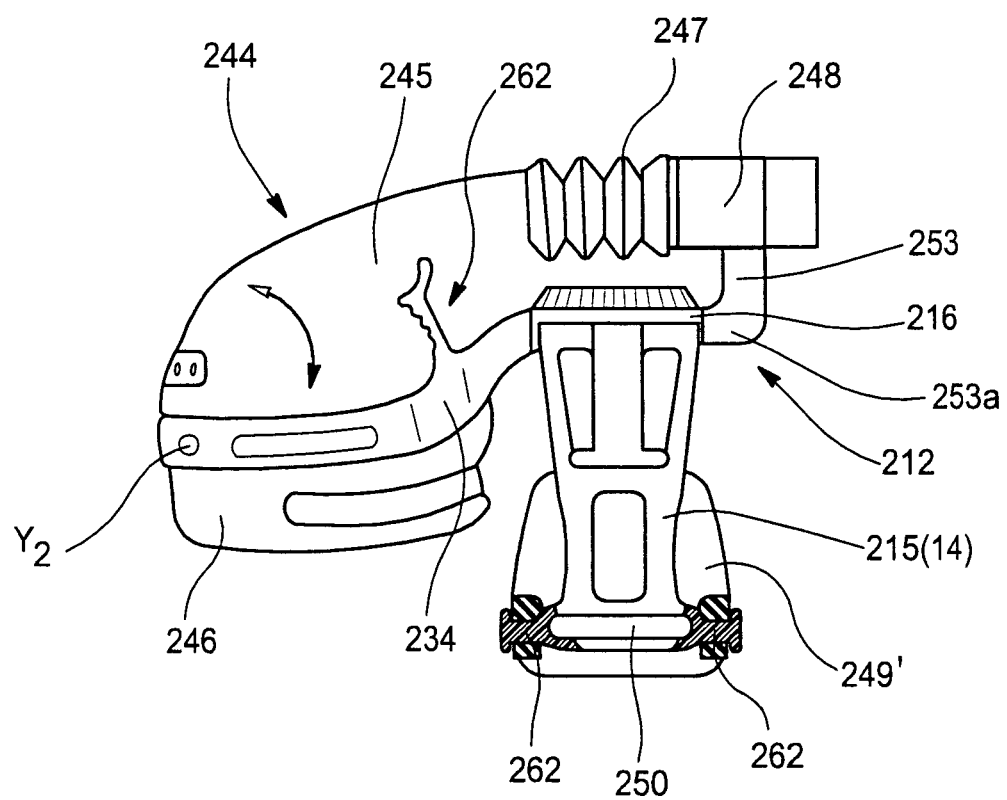
FIG. 20 shows a side view of a breathing mask application device with a breathing mask arrangement pivotably movably accommodated therein.

FIG. 20 shows an application device which is provided with a breathing mask arrangement 244 and which, similarly to the embodiments described hereinbefore, includes an adjusting drive 212, by way of which the arm elements 214, 215 which project on both sides from a base portion 216 of the adjusting drive 212, can be adjustably pivoted. In a departure from the embodiments described hereinbefore, in this case the mask base body 245 is tiltable, independently of the adjusting movement of the arm elements which is caused by the adjusting drive 212, about a pivot axis Y1 which extends approximately in the region of the zone of the sealing lip device, which is adjacent to the nostrils of a mask user, and which extends substantially parallel to a transverse line 206 joining the eyebrows. The pivotal position of the mask base body 245 with respect to the holding portion 234 can be fixed by an arresting device 262. A sufficient relative mobility of the mask base body 245 with respect to a breathing hose connecting portion 248 provided for the connection of a respiratory gas conduit is achieved by a flexible conduit portion 247, as is provided also in the embodiment shown in FIG. 18. In this embodiment the mask base body is preferably produced integrally with a sealing lip device 246 from a elastomer material, preferably silicone rubber. The breathing hose connecting portion 248 in this embodiment is rigidly coupled to the base portion 216 and is made from a hard thermoplastic material.

Mounted to the arm elements 214, 215 there are also forehead pads 249' which are provided to bear against the surface of the forehead of the mask user, the forehead pads 249' being suspended tiltably on trunnions or projections 262 which are formed integrally with the respective arm element 215, 214. Disposed between the trunnions 262 there is again an eye portion 250 for passing therethrough an end portion of an upper band arrangement. It is possible for the base portion 216 to be guided displaceably on an arm portion 253a which extends from the holding portion 234 to the holding foot 253. That makes it possible for the vertical spacing of the forehead support device from the sealing lip device 246 also to be variably altered.

FIG. 21 shows a further embodiment of the holding portion 234, as can be used for example in relation to the embodiments shown in FIGS. 19 and 20. The holding portion 234 is provided with a coupling structure which is provided for coupling a mask base body (not shown here) and by means of which the mask base body can be coupled to the holding portion 234 in different coupling positions.

FIG. 22 shows a forehead support device which can be fitted by way of a breathing hose connecting portion 248 onto a connecting part 264 of a breathing mask which is indicated here.

The breathing hose connecting portion 248 is coupled to a base portion 216 of the forehead support device by way of a holding foot 253. By way of an adjusting wheel 222 arranged between the breathing hose connecting portion 48 and the base portion 216 the coupling members 217, 218 are adjustably movable in a direction radially with respect to the axis of rotation 224 of the adjusting wheel 222. The arm elements 214, 215 are definedly pivoted about the axes X1, X2 by suitable positioning of the coupling members 217, 218.

Mounted to the arm elements 214, 215 are forehead contact pads 249 by way of which the arm elements 214, 215 are supported on the forehead region of a mask user. Provided in the region of the forehead pads 249 on the arm elements 214, 215 are eye portions 250 through which the respective end portion of an upper belt arrangement can be passed.

Figure 23:
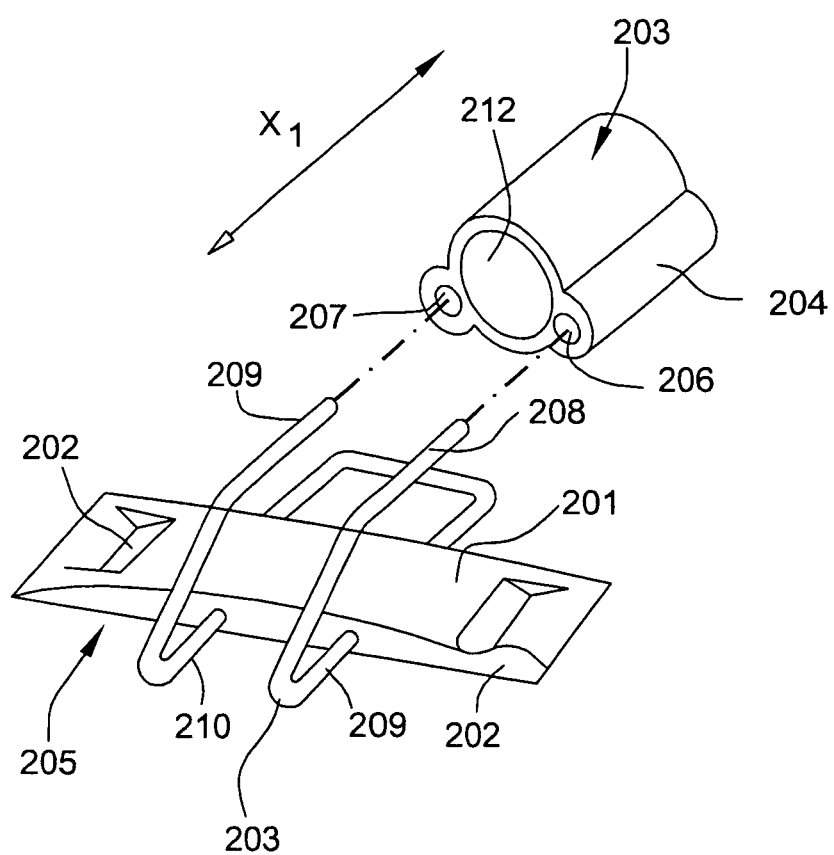
FIG. 23 is a perspective view of a forehead support device with a headband portion and a coupling structure connected thereto for supporting a conduit portion.
Figure 35:
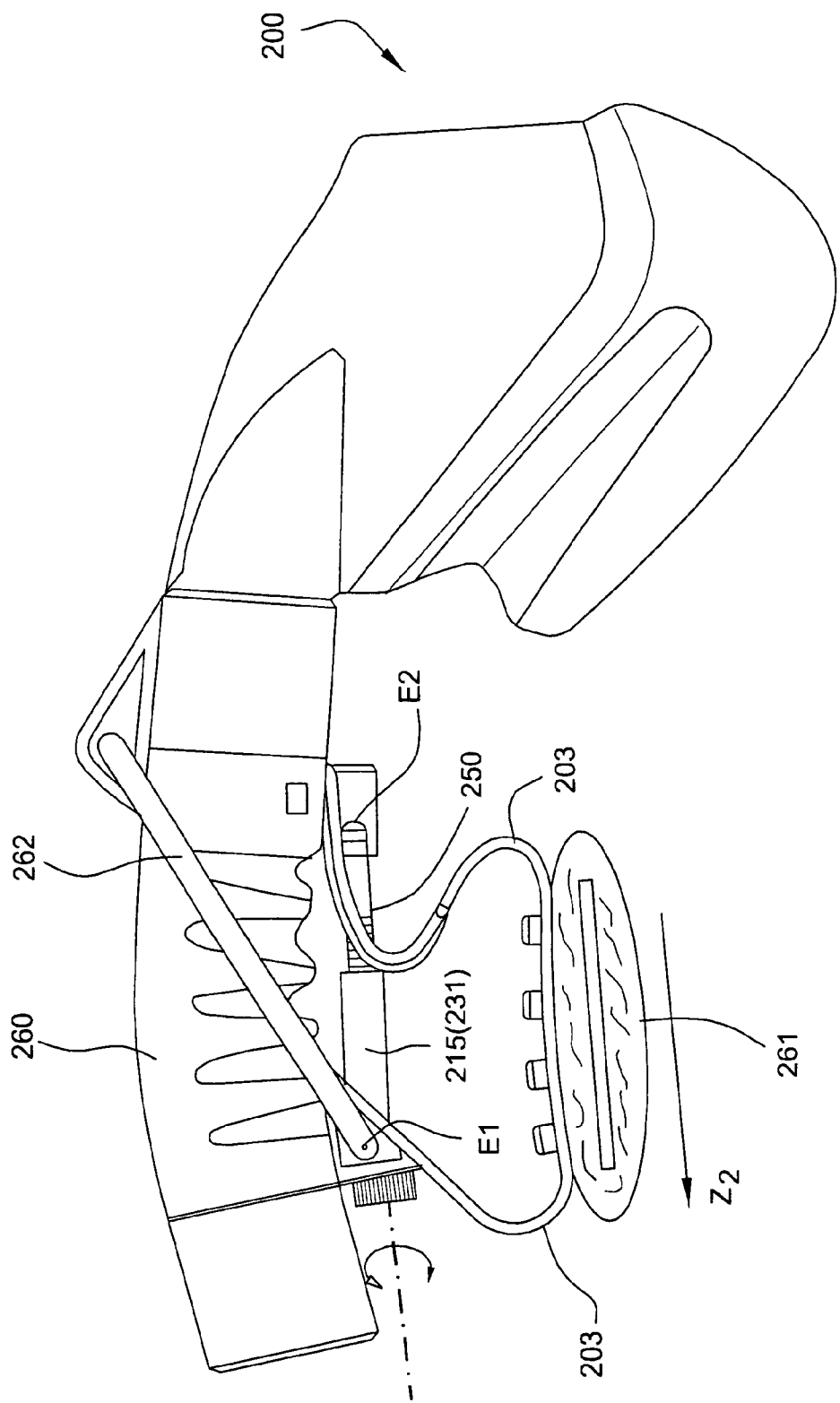
FIG. 35 shows an embodiment of a breathing mask arrangement with a tube portion which is steplessly variable in curvature—and a forehead support device coupled thereto.

FIG. 23 shows a forehead support device which can be used for example in conjunction with the breathing mask 200 shown in FIG. 35. This forehead support device includes a forehead support portion 201 which is made from a soft material, in particular elastomer material, and which can be applied in the forehead region of a mask connector by way of an upper headband portion of a headband arrangement (see in that respect FIG. 37). In this embodiment the forehead support portion 201 includes two tongue portions 202 through which a fixing band portion of the headband arrangement can be passed. Mounted on the forehead support portion 201 is a coupling structure 203 by way of which a conduit connecting element 204 is supported at a spacing determined by the geometry of the coupling structure in front of the lower support surface 205 of the forehead support portion. In this embodiment the conduit connecting element is also formed from an elastomer material and includes two joining openings 206, 207 by way of which the conduit connecting element 204 can be sufficiently firmly fitted on to two limb portions 208, 209 of the coupling structure 203.

The conduit connecting element 204 and the coupling structure 203 can be of such a configuration that the conduit connecting element 204 can be steplessly positioned relative to the forehead support portion 201 in the direction of the axis X1 indicated here. Further adjustment options in respect of the position of the conduit connecting element 204 relative to the forehead support portion 201 can be embodied also by the provision of different possible ways of coupling the coupling structure 203 to the forehead support portion 201. In the embodiment illustrated here it is possible for the longitudinal limbs 208, 210 which here pass in pairs through the forehead support portion 201 to be supported displaceably in the forehead support portion 201. The dimensions of the longitudinal limbs 209, 210 and the through passages provided in the forehead support portion for passing the longitudinal limbs therethrough are preferably established in such a way as to ensure adequately frictional fixing of the coupling structure 203 in the desired relative position.

The coupling structure 203 forms a through passage 212 which is of such a size that a connecting tube portion of a breathing mask (see in that respect FIG. 35) can be fitted thereinto. The through passage 212 is further of such a dimension that a breathing gas hose can be fitted therein, on a side remote from the breathing mask, by way of a washing-out valve arrangement.

The spacing between the support surface 205 of the forehead support portion 201 and the coupling structure 203, which is required according to the individual facial structure of the user of the mask, can be adjusted by the provision of various coupling structures 203 or by plastic deformation, for example bending of the coupling structure 203.

Figure 24:
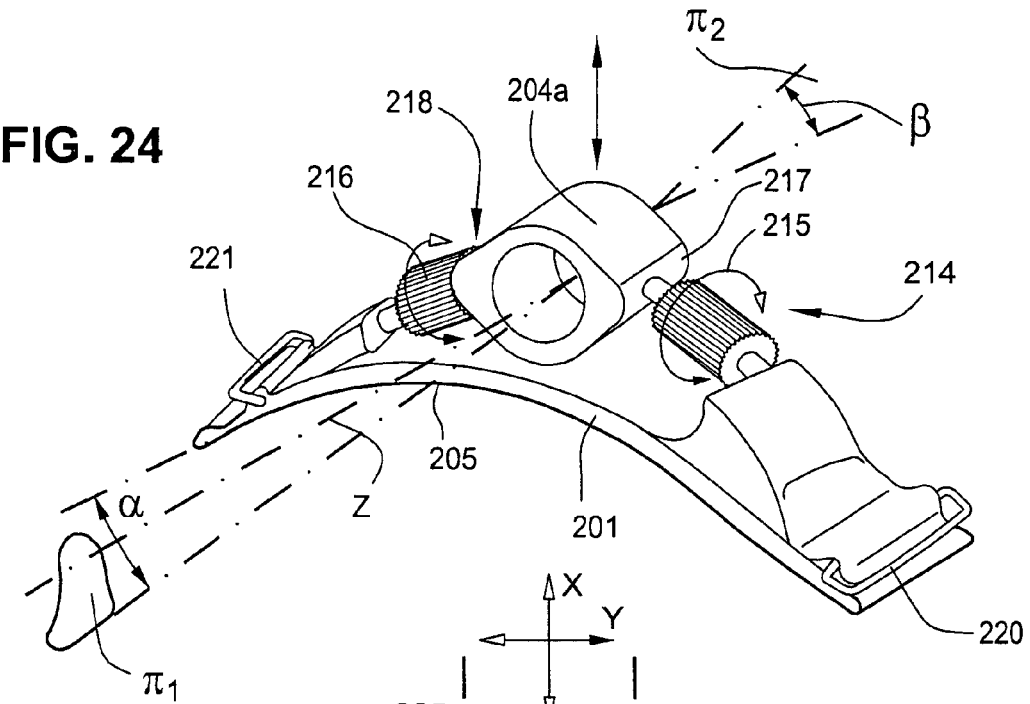
FIG. 24 shows a perspective view of a further embodiment of a forehead support device with an adjusting mechanism for adjusting the forehead spacing and the lateral position of a conduit portion.

FIG. 24 shows a further embodiment of a forehead support device. This forehead support device also includes a forehead support portion 201 which is made from a sufficiently elastically deformable material, preferably silicone rubber. A conduit passage element 204a is supported displaceably by way of an adjusting device 214 on the forehead support portion 201. The conduit passage element 204a can be of a configuration similar to that described hereinbefore with reference to FIG. 23 as a connecting element by way of which coupling of a connecting portion on the mask side to a respiratory gas conduit is permitted. As an alternative thereto it is also possible for the conduit passage element 204a to be of such a design configuration that it merely embraces a respiratory gas conduit portion and in so doing couples it adjustably in respect of height to the forehead support portion 201.

In this embodiment the adjusting device 214 includes two adjusting drive devices 215 by way of which the spacing of the central axis Z of the conduit passage element 204a with respect to the support surface 205 of the forehead support portion 201 is steplessly adjustable. In this embodiment the adjusting drive devices 215, 216 are provided with internally threaded sleeves which are manually rotatable by way of a knurling provided on the external periphery thereof. The internally threaded sleeves are in engagement with screwthread portions (not shown) of adjusting screws 217, 218 so that manual rotation of the respective internally threaded sleeve causes the effective length of a strut formed by the internally threaded sleeve and the adjusting screw in engagement therewith to be steplessly adjustable. The spacing of the conduit connecting element 204a can also be individually adjusted by the user of the mask by varying the effective length of those struts.

Coupling means for coupling the forehead support portion to a headband arrangement are also provided on the forehead support portion 201. In this embodiment those coupling means are afforded by loop elements 220, 221.

Figure 25:
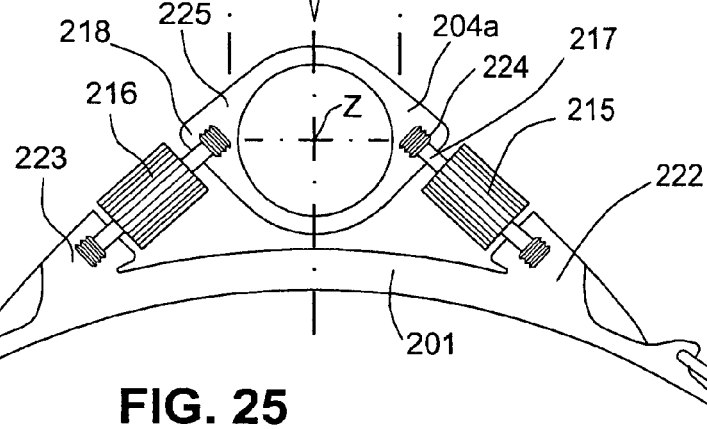

As can be seen from FIG. 25 the forehead support portion 201 is provided with support locations 222, 223 in which the two adjusting drive devices 215, 216 are respectively anchored on one side. Also provided on the conduit passage element 204a are support locations 224 in which the end portions of the adjusting screws 217, 218 are sufficiently non-rotatably anchored.

The arrangement is here such that the operative length of the structure coupling the conduit passage element 204a to the respective support locations 222, 223 is steplessly variable by actuation of the two adjusting drive devices 215, 216. By rotation of the internally threaded sleeves which are indicated here and which are knurled on the outside periphery (see the arrow symbols in FIG. 24), it is possible to adjust the position of the conduit passage element 204a relative to the forehead support portion 201 both in the direction of the axes X, Y indicated here. It is further possible for the conduit passage element 204a also to be pivoted slightly in respect of the longitudinal axis Z thereof.

Figure 26:
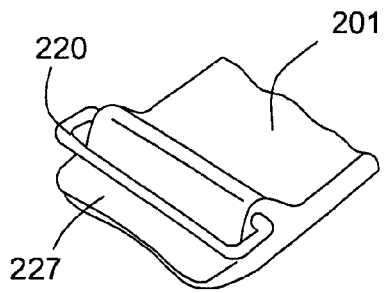
FIG. 26 shows a detail view of an end region of a forehead contact portion with a loop support which terminates flat.

FIG. 26 is in the form of a detail view showing the coupling structure implemented in the embodiment of FIGS. 24 and 25 for coupling the forehead support portion 201 to an upper headband. The loop element 220 is anchored in the forehead support portion 201 in the region of that headband coupling structure. The forehead support portion 201 is provided with a tongue 227 which is thin at its end and which in the application position of the forehead support portion extends between the loop element 220 and the forehead of the user of the mask and in that situation cushions a region of the headband which passes around the loop element 220 and promotes a gentle progressive reduction in the pressure in relation to surface area, caused by the forehead support portion 201.

Figure 27:
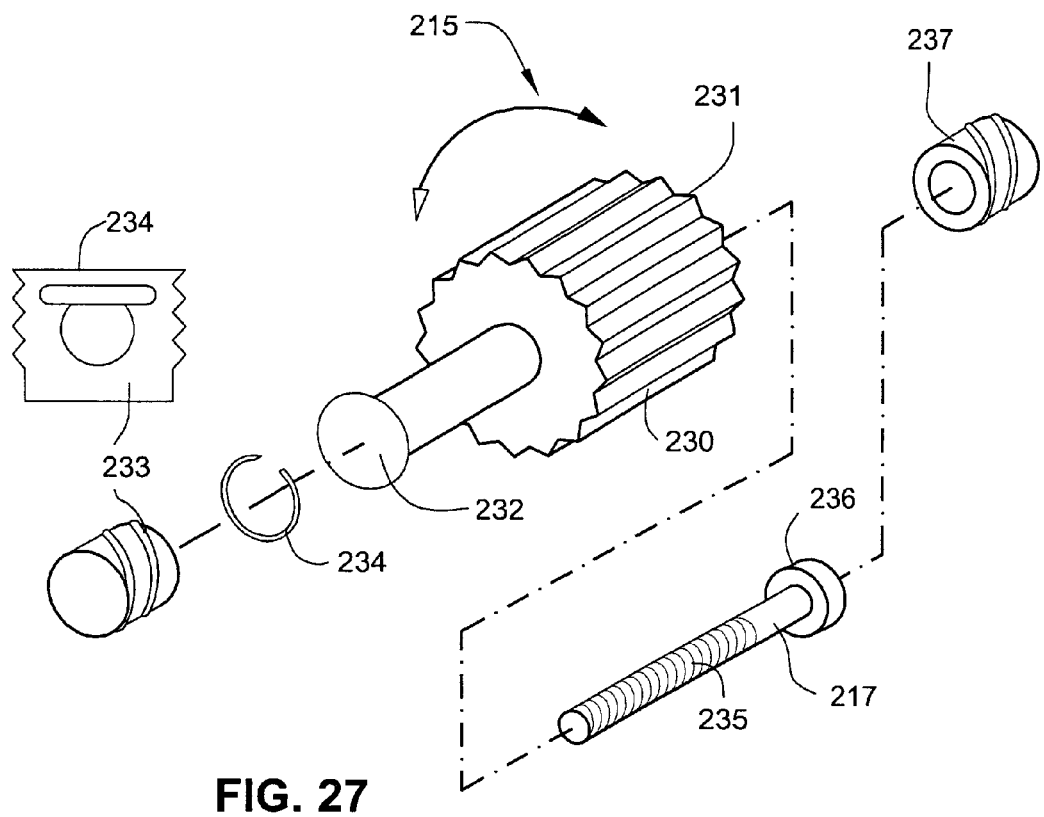
FIG. 27 shows a partial diagrammatic view to illustrate a screw spindle variant of an adjusting drive as can be used for example in the embodiment shown in FIGS. 24 and 25.

FIG. 27 shows a preferred embodiment of an adjusting drive device 215 as can be used in the embodiment of FIGS. 24 and 25. The adjusting drive device 215 includes the sleeve 231 which is provided with external peripheral knurling 230 and which has an internal bore with an internal thread structure. The sleeve 231 includes a pivot portion 232 which is here of a spherical configuration and can be fitted rotatably into a seat element. The pivot portion 232 can be secured in the seat element 233 by way of a spring ring 234 in such a fashion that the pivot portion 232 is admittedly rotatable and tiltable through a sufficient angular region, but it is anchored in the seat element 233 in such a way as to be secured in the axial direction. A thread portion 235 of the adjusting screw 217 is in screwthreaded engagement with the sleeve 230 in the assembled condition. Provided on the adjusting screw 217 is a fixing head 236 which can also be fitted into a seat element 237. The coupling of the fixing head 236 to the seat element 237 is implemented, as a departure from the manner of coupling the seat element 233 to the pivot portion 232 provided at the sleeve side, in such a way that the adjusting screw 217 is anchored substantially non-rotatably in the seat element 237.

The adjusting drive device 215 illustrated here makes it possible for the spacing of the two seat elements 233, 237 to be steplessly adjusted by individual rotation of the sleeve 231.

Figure 28:
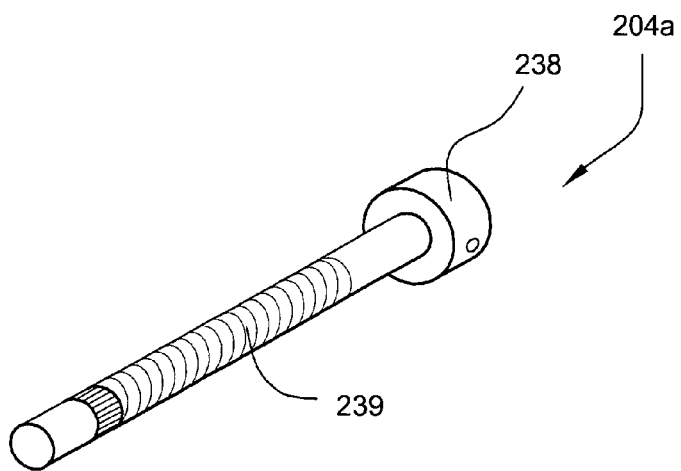
FIG. 28 is a diagrammatic view to illustrate a conduit portion made from elastomer material with an integral mask connecting socket which can be supported in a forehead support device.

The conduit passage element 204a provided in the embodiment of FIGS. 24 and 25 can also be of such a configuration that it forms part of the respiratory gas conduit itself. Such a configuration for the conduit passage element 204a is shown in FIG. 28. The conduit passage element 204a includes the support portion 238 co-operating with the adjusting drive devices and a flexible hose conduit portion 239 which is provided in this embodiment. Provided on the hose conduit portion 239 is a push-in sleeve, by way of which a further hose conduit can be rotatably connected.

Figure 29:
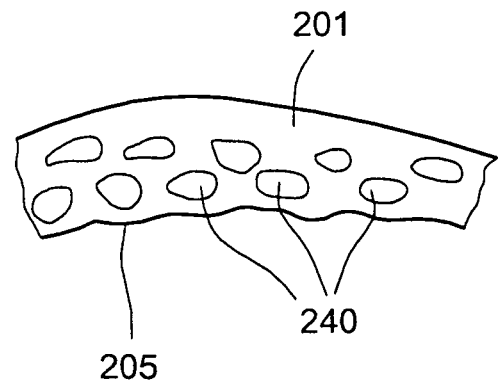
FIG. 29 shows a sectional view to illustrate a variant of the forehead support portion, which is of a cushioned configuration by virtue of pores or caverns.

FIG. 29 shows a detail view of a preferred embodiment of the forehead support portion 201 in the region of the forehead support surface 205 which bears against the forehead of the user of the mask. Provided in the forehead support potion 201 are caverns 240 which can provide for a particularly uniform distribution of surface pressure in the region of the contact surface 205.

Figure 30:
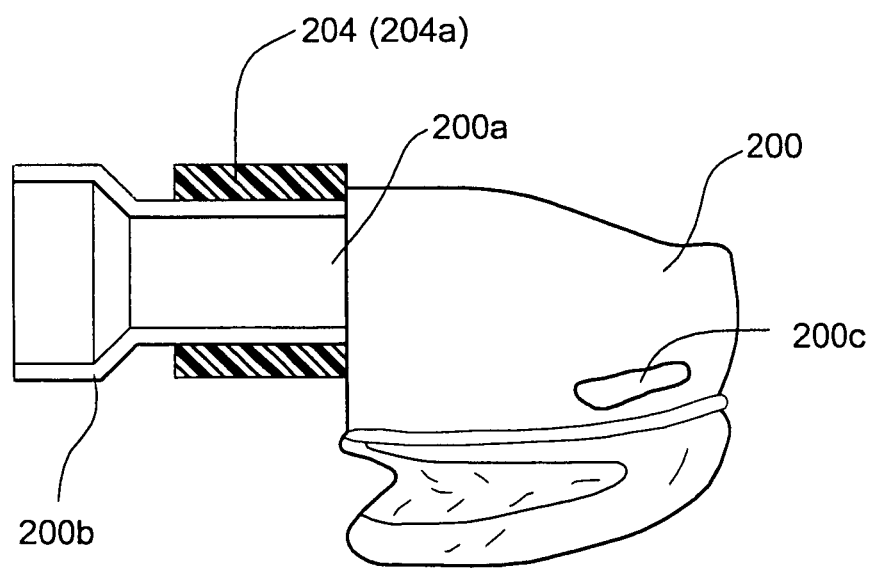
FIG. 30 is a sectional view through a connecting region formed in the region of the forehead support, between the connecting portion of a breathing mask and a conduit portion (here the mask-side socket of a washing-out adaptor—AEROCLICK (registered trade mark of MAP Medizin-Technologie GmbH); Wisper-Swivel (Respironics))

FIG. 30 is a view in the form of a simplified section showing how the conduit connecting element 204 or also the conduit passage element 204a can be used for coupling a connecting portion 200a provided on the breathing mask 200 to a further respiratory gas conduit member 200b. In this embodiment the respiratory gas conduit member 200b forms part of a washing-out valve as is described in particular in German patent application DE 198 . . . . Provided on the breathing mask 200 are loop portions 200c, by way of which the breathing mask 200 can be fixed by means of a lower headband arrangement in the region of the nose of the mask user.

Figure 31:
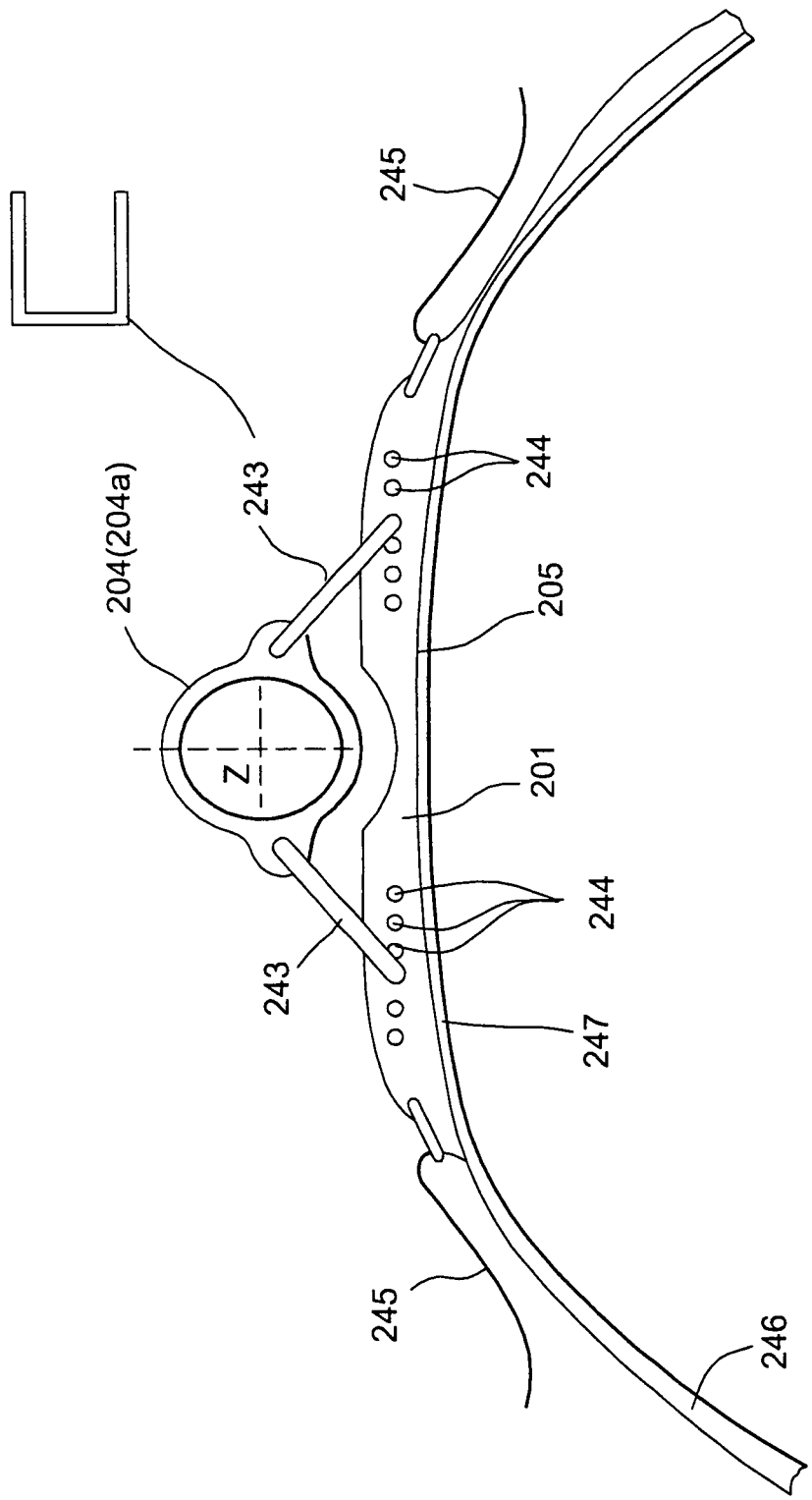
FIG. 31 is a diagrammatic view to illustrate a further variant according to the invention of a forehead support device.

FIG. 31 shows a forehead support device which has substantial points in common with the embodiment already described hereinbefore with reference to FIG. 23. The conduit connecting element 204 (also 204a) is coupled by way of loop elements 243 to the forehead support portion 201. Adjustment of the spacing of the central axis Z of the conduit connecting element 204 relative to the underside (contact surface 205) of the forehead support portion is achieved in this case in that the loop elements 243 can be fitted into suitably selected bores 244. Depending on which bores 244 are selected for anchoring the loop elements 243 at the forehead support portion, that affords different spacings of the central axis Z relative to the contact surface 205. The forehead support portion 201 can be fixed by way of fixing straps 245 to an upper headband arrangement 246. In this embodiment the upper headband arrangement 246 includes a band portion 247 which extends between the two fixing straps 245 under the forehead support portion 201 and in that case additionally cushions the forehead support portion against the forehead of the mask user.

Figure 32:
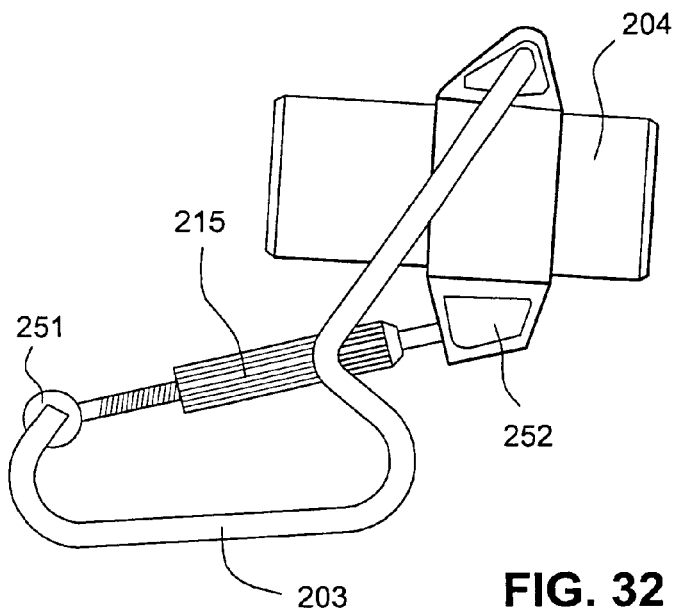
FIG. 32 shows an embodiment of a connecting adaptor with forehead support adjustably pivoted thereto.
Figure 33:
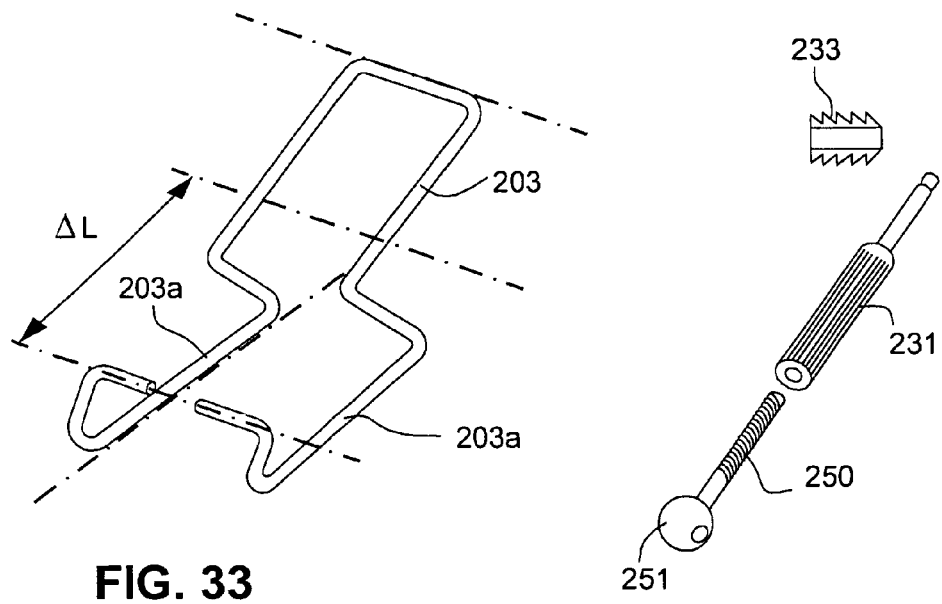
FIG. 33 shows a bent wire variant of the forehead support of FIG. 32.
Figure 34:
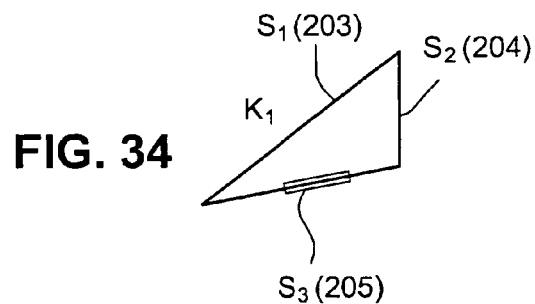
FIG. 34 shows a screwthread sleeve/spindle variant of the adjusting device of FIG. 32.

FIG. 32 shows a forehead support device for supporting a breathing mask arrangement against the forehead, which also permits stepless adjustment of the support height. In this embodiment a conduit connecting element 204 which can be fitted on to a connecting portion of a breathing mask is pivotably coupled to the coupling structure 203. In this embodiment the coupling structure 203 is in the form of a bent wire member as is shown by way of example in FIG. 33. The coupling structure 203 in conjunction with an adjusting drive device 215 forms the strut triangle indicated in the diagrammatic view at K1. The strut S1 is in this case formed by the coupling structure 203, the strut S2 is formed by the conduit connecting element 204 and the strut S3 by the adjusting drive 215. A preferred structure of the adjusting drive 215 is illustrated in FIG. 34. The adjusting drive in FIG. 34 includes a screwthreaded spindle 250 which is pivotably but non-rotatably coupled to the coupling structure 203 by way of a pivot head 251 as can be seen in FIG. 32. The screwthreaded spindle 250 is in engagement with an internally threaded sleeve 231 which in turn is anchored rotatably by way of a seat element 233 in a radially projecting portion 252 of the conduit connecting element 204. Rotation of the sleeve 231 makes it possible to alter the effective spacing between the pivot head 251 and the seat element 233 and thus to pivot the coupling structure 203 relative to the conduit connecting element 204. In that way it is possible to implement different relative positions of the lower limbs 203a relative to a breathing mask connected to the conduit connecting element 204, and thus different forehead spacings.

FIG. 35 shows a breathing mask arrangement comprising a breathing mask 200 and a forehead support device coupled thereto. The forehead support device includes an elastically deformable conduit portion 260 which is here made from an elastomer material. The respiratory gas conduit portion 260 can be adjustably curved by way of an adjusting drive device 215. In this embodiment the adjusting drive device includes a screwthread device having an internally threaded sleeve 231 which is in engagement with a screwthreaded spindle 250. Rotation of the sleeve 230 makes it possible to alter the spacing between the points E1 and E2. Upon a change in that spacing the coupling structure 203 which can be seen here is elastically deformed. The deformation characteristic of the coupling structure 203 is so selected that the cushioning 261 on the coupling structure 203 always assumes a favourable orientation relative to the breathing mask 200. The adjusting drive device 215, the respiratory gas conduit portion 260 and a pivotal loop element 262 form a strut triangle which in its basic structure substantially corresponds to the strut triangle described hereinbefore with reference to FIGS. 32-34 and the sketch K1 contained therein.

The cushioning 261 is releasably coupled to the coupling structure 203 so that the position of the cushioning is adjustably variable in the direction of the axis Z2 indicated here.

Figure 36:
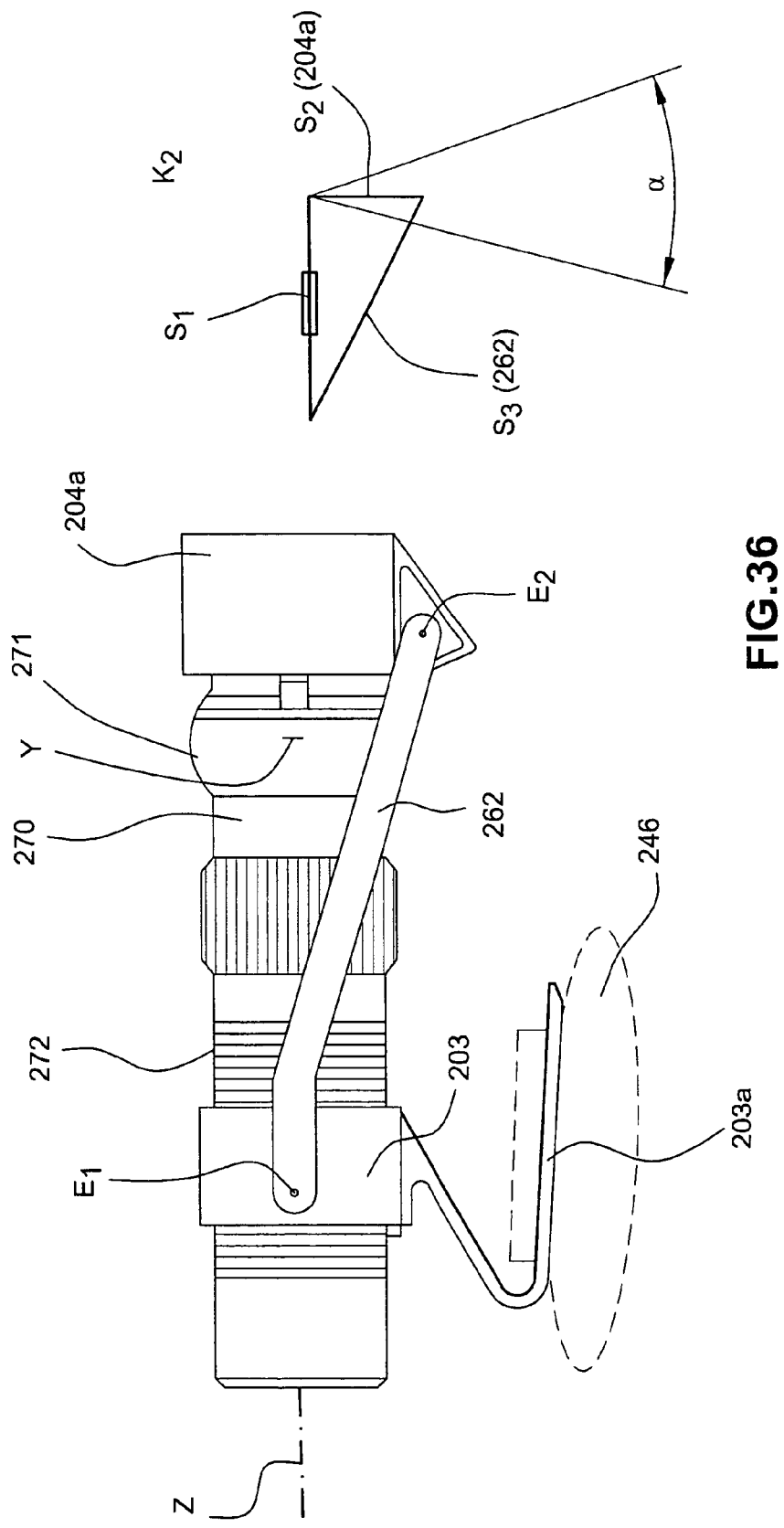
FIG. 36 shows a side view of a further variant of a variable-curvature conduit portion.

FIG. 36 shows a forehead support device having a conduit passage element 204a which can be fitted on to a breathing mask 200. Provided on that conduit passage element 204a is a ball joint trunnion which permits rotatable and pivotable mounting of a tube sleeve element 270. The tube sleeve element 270 here includes a spherical portion 271 which is of such a configuration that it is carried on the trunnion portion of the conduit passage element 204a in substantially sealing relationship but sufficiently easily movably thereon. Provided on the tube sleeve element 270 is a male screwthread portion 272 which is in threaded engagement with a coupling structure 203. The coupling structure 203 includes limb portions 203a which can be coupled to a preferably cushioned upper headband arrangement 246. By rotation of the tube sleeve element 270 about the central axis Z, it is possible, by virtue of the screwthread engagement between the male threaded portion 272 and the coupling structure 203, to steplessly vary the spacing between the points E1 and E2. In the region of the points E1, E2 an adjusting loop element 262 is pivotably coupled to the coupling structure 203 and the conduit passage element 204 respectively. In this embodiment the tube sleeve element 270 jointly with the coupling structure 203 forms a strut S1 in the sketch K2 illustrated here. The conduit passage element 204a, with its portion which can be fitted directly on to the breathing mask, forms the strut S2, while in this triangle the pivotal loop element 262 forms the strut S3. By altering the operative length of the strut S1 it is then possible for the tube sleeve element 270 and jointly therewith the coupling structure 203 to be steplessly pivoted about the axis Y indicated here.

The forehead support devices described hereinbefore with reference to FIGS. 35 and 36 make it possible for the support of a breathing mask to be steplessly matched to the individual facial structure in the region in which the mask rests on the bridge of the nose of the user. The contact pressure in the region of the bridge of the nose can be altered in particular in the two embodiments described hereinbefore, without in that respect involving particular changes in the connecting portion at the respiratory gas conduit side, afforded by the forehead support device.

Figure 37:
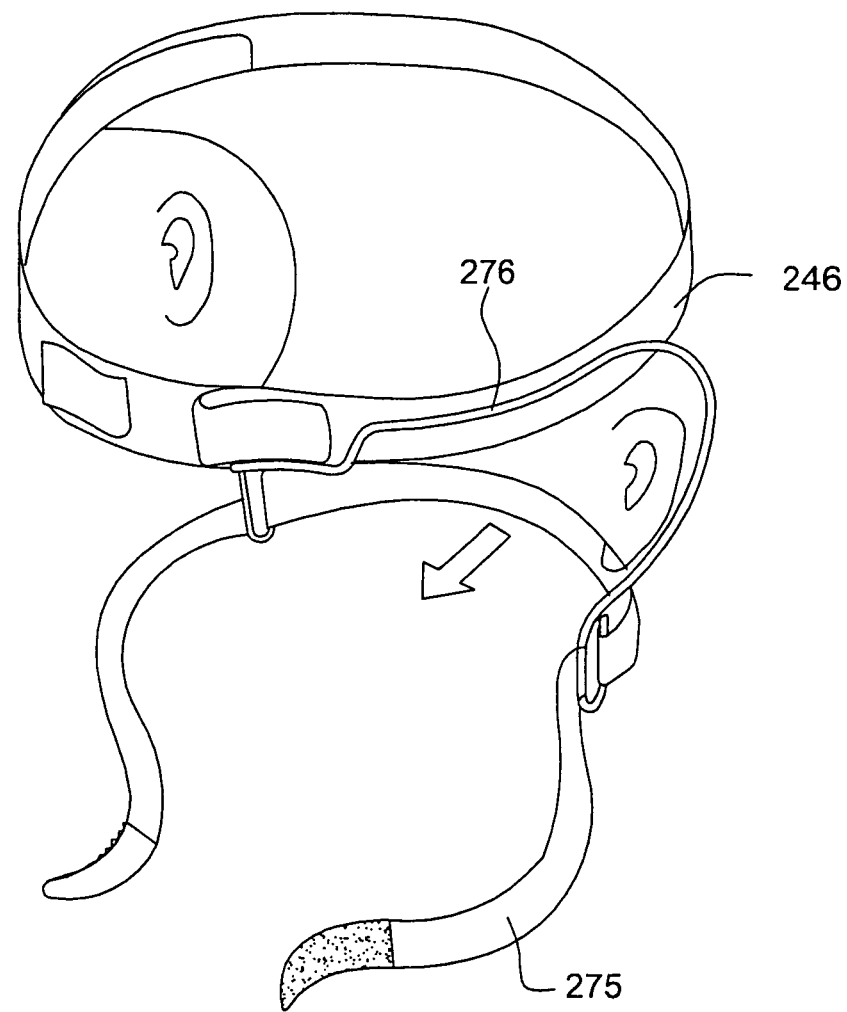
FIG. 37 shows a perspective view of a headband arrangement in particular for use with the forehead support devices described hereinbefore.

FIG. 37 shows a headband arrangement which can be used in conjunction with the above-described forehead support devices and breathing mask arrangements for the comfortable application of a breathing mask.

The pressure of the breathing mask against the face of the user can be afforded either by applying suitable holding forces by means of the upper headband arrangement 246 and a lower headband arrangement 275 and in particular to transmit the torque required for generating the contact pressure forces in the region of the top lip by way of the loop elements 246 illustrated here.

What is claimed is:

1. A breathing mask arrangement for delivering breathable gas to a patient, comprising:
    a frame;
    a mask having a body portion that defines a mask interior breathing chamber and a sealing portion structured to engage a patient's face;
    the frame has a front side and a rear side, and the frame defines an opening through which at least a portion of the body portion is exposed towards the front side of the frame;
    a respiratory gas conduit member provided to the frame, the respiratory gas conduit member including a rotatably fitted hose connecting sleeve adapted to couple to a respiratory gas hose; and
    a forehead support provided to the frame, the forehead support including a forehead cushion element including a contact portion having a contact surface adapted to contact a patient's forehead and a connecting structure structured to couple the forehead cushion element to the forehead support and allow pivoting and/or tilting movement of the contact portion relative to the forehead support, the connecting structure including a portion adapted to be received within a respective opening provided in the forehead support to couple the forehead cushion element to the forehead support.

2. The breathing mask arrangement according to claim 1, wherein the forehead support is movably mounted to the frame.

3. The breathing mask arrangement according to claim 2, further comprising a fixing mechanism by which the forehead support and the frame can be fixed in a selected relative position.

4. A breathing mask arrangement according to claim 3, wherein the fixing mechanism includes a tooth arrangement structured to positively lock the forehead support relative to the frame.

5. A breathing mask arrangement according to claim 3, wherein the fixing mechanism includes a manually engageable actuator that is manually movable between locked and unlocked positions.

6. A breathing mask arrangement according to claim 1, wherein the forehead support includes arm elements adapted to support the forehead cushion element, each arm element including an end portion that provides an opening through which a portion of an upper headband arrangement may pass.

7. A breathing mask arrangement according to claim 1, wherein the mask is in communication with the nose and/or mouth opening of the patient.

8. A breathing mask arrangement according to claim 1, wherein the frame engages the body portion of the mask.

9. A breathing mask arrangement, comprising:
    a holding portion including a frame-like configuration;
    a mask provided to the holding portion, the mask including a mask base body and a sealing lip device coupled thereto, the sealing lip device adapted to sealingly contact a mask user and the mask base body defining an interior of the mask adapted to receive respiratory gas;
    a forehead support device provided to the holding portion and adapted to extend to the mask user's forehead; and
    a forehead pad directly and tiltably mounted to the forehead support device, the forehead pad adapted to bear against the mask user's forehead.

10. A breathing mask arrangement according to claim 9, wherein the forehead support device includes arm elements adapted to support the forehead pad, each arm element including an eye portion through which a portion of an upper headband arrangement is structured to pass.

11. A breathing mask arrangement according to claim 9, wherein the sealing lip device is made from an elastomeric material.

12. A breathing mask arrangement according to claim 9, wherein the holding portion is structured to embrace the mask base body at least in a side region thereof.

13. A breathing mask arrangement according to claim 9, further comprising coupling structures to couple the holding portion to a lower headband arrangement.

14. A breathing mask arrangement according to claim 9, wherein the forehead support device is movably coupled to the holding portion.

15. A breathing mask arrangement according to claim 14, further comprising an adjusting device to selectively adjust a position of the forehead support device relative to the holding portion.

16. A breathing mask arrangement according to claim 9, wherein the mask base body and the sealing lip device are provided as a one-piece structure.

* * * * *